US010752954B2

(12) United States Patent
Raj et al.

(10) Patent No.: US 10,752,954 B2
(45) Date of Patent: Aug. 25, 2020

(54) METHOD FOR DETECTING MUTATIONS IN SINGLE CELLS OR SINGLE MOLECULES

(71) Applicant: THE TRUSTEES OF THE UNIVERSITY OF PENNSYLVANIA, Philadelphia, PA (US)

(72) Inventors: Arjun Raj, Wynnewood, PA (US); Marshall Levesque, Rahway, NJ (US)

(73) Assignee: The Trustees Of The University Of Pennsylvania, Philadelphia, PA (US)

(*) Notice: Subject to any disclaimer, the term of this patent is extended or adjusted under 35 U.S.C. 154(b) by 99 days.

(21) Appl. No.: 14/774,543

(22) PCT Filed: Mar. 13, 2014

(86) PCT No.: PCT/US2014/025703
§ 371 (c)(1),
(2) Date: Sep. 10, 2015

(87) PCT Pub. No.: WO2014/160046
PCT Pub. Date: Oct. 2, 2014

(65) Prior Publication Data
US 2016/0046999 A1    Feb. 18, 2016

Related U.S. Application Data

(60) Provisional application No. 61/785,498, filed on Mar. 14, 2013.

(51) Int. Cl.
*C12Q 1/68* (2018.01)
*C07H 21/00* (2006.01)
(Continued)

(52) U.S. Cl.
CPC ......... *C12Q 1/6886* (2013.01); *C12Q 1/6827* (2013.01); *C12Q 1/6841* (2013.01); *C12Q 2600/156* (2013.01)

(58) Field of Classification Search
CPC ............ C07H 21/00; C12P 19/34; C12Q 1/68
See application file for complete search history.

(56) References Cited

U.S. PATENT DOCUMENTS 5,234,810 A * 8/1993 Kehrli, Jr. ............ C12O 1/6883
435/6.16
6,090,606 A * 7/2000 Kaiser ..................... C12N 9/22
435/199

(Continued)

FOREIGN PATENT DOCUMENTS

WO    2011038403 A1    3/2011
WO    2012058488 A1    5/2012

OTHER PUBLICATIONS

Levsky et al., The Spatial Order of Transcription in Mammalian Cells. J. of Cellular Biochemistry 102 :609 (2007).*

(Continued)

*Primary Examiner* — Ethan C Whisenant
(74) *Attorney, Agent, or Firm* — Saul Ewing Arnstein & Legr LLP; Kathryn Doyle; Justin Crotty

(57) ABSTRACT

The invention provides a high efficiency fluorescence in situ hybridization (FISH) method for detecting mutations on individual RNA transcripts, including both exonic and intronic RNA transcripts. In certain embodiments, the method is used to quantify allelic expression at the population and single cell level, and also to distinguish maternal chromosomes from paternal chromosomes in single cells.

13 Claims, 8 Drawing Sheets

Specification includes a Sequence Listing.

(51) Int. Cl.
*C12Q 1/6886* (2018.01)
*C12Q 1/6841* (2018.01)
*C12Q 1/6827* (2018.01)

(56) References Cited

U.S. PATENT DOCUMENTS

| | | | | |
|---|---|---|---|---|
| 7,348,146 | B2* | 3/2008 | Belousov | C12Q 1/6827 435/6.14 |
| 8,244,021 | B2* | 8/2012 | Lett | G01N 21/6428 382/128 |
| 2002/0026651 | A1* | 2/2002 | Hutton | C07K 14/4711 800/18 |
| 2002/0048763 | A1* | 4/2002 | Penn | G16B 30/00 435/6.11 |
| 2004/0009512 | A1* | 1/2004 | Ares | C07H 21/04 435/6.1 |
| 2004/0053254 | A1* | 3/2004 | Wangh | C07H 21/00 435/6.1 |
| 2005/0287548 | A1* | 12/2005 | Bao | B82Y 5/00 435/6.11 |
| 2007/0269866 | A1* | 11/2007 | Stafford | C12N 9/0006 435/69.1 |
| 2007/0298425 | A1* | 12/2007 | Hogan | C12Q 1/6837 435/6.11 |
| 2009/0170719 | A1* | 7/2009 | Kazakov | C12Q 1/6832 506/9 |
| 2013/0023433 | A1* | 1/2013 | Luo | C12Q 1/6841 506/9 |
| 2013/0274135 | A1* | 10/2013 | Zhang | C12Q 1/6832 506/9 |
| 2016/0046999 | A1* | 2/2016 | Raj | C12Q 1/6827 435/6.11 |

OTHER PUBLICATIONS

Zhang et al., Control of DNA Strand Displacement Kinetics Using Toehold Exchang JACS131: 17303 (2009).*
Saiki et al., Nature 324: 163 (Year: 1986).*
Ried et al., Simultaneous visualization of seven different DNA probes by in situ hybridization using combinatorial fluorescence and digital imaging microscopy. PNAS 89 : 1388 (Year: 1992).*
Li et al..,A new class of homogeneous nucleic acid probes based on specific displacement hybridization. Nucleic Acids Research 30(2) : e5 . (Year: 2002).*
Maruyama et al.,Masking oligonucleotides improve sensitivity of mutation detection based on guanine quenching. Analytical Biochemistry 354 :8-14. (Year: 2006).*
Vary, C.P.H., Nucleic Acids Research 15(17) : 6883. (Year: 1987).*
Zhang et al.JACS 131 :17303 (Year: 2009).*
International Search Report and Written Opinion for PCT International Application No. PCT/US2014/025703 dated Jul. 3, 2014.
Levesque, et al., "Visualizing SNVs to quantify allele-specific expression in single cells", Nat Methods. 10(9), Sep. 2013, 865-867.

* cited by examiner

FIGs. 1B-1D
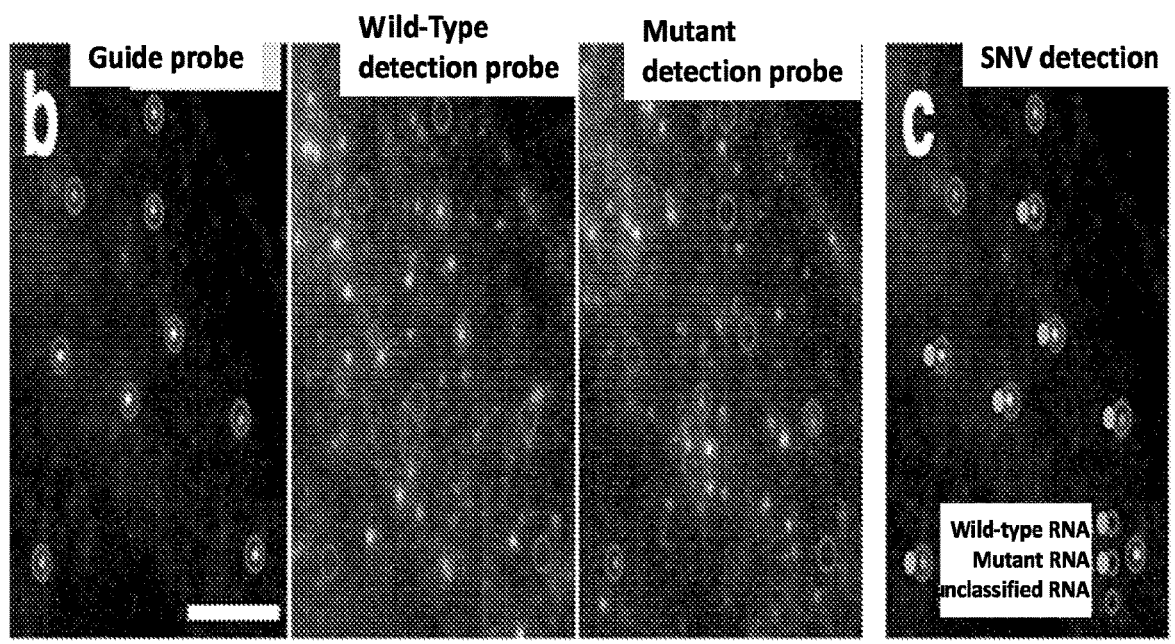
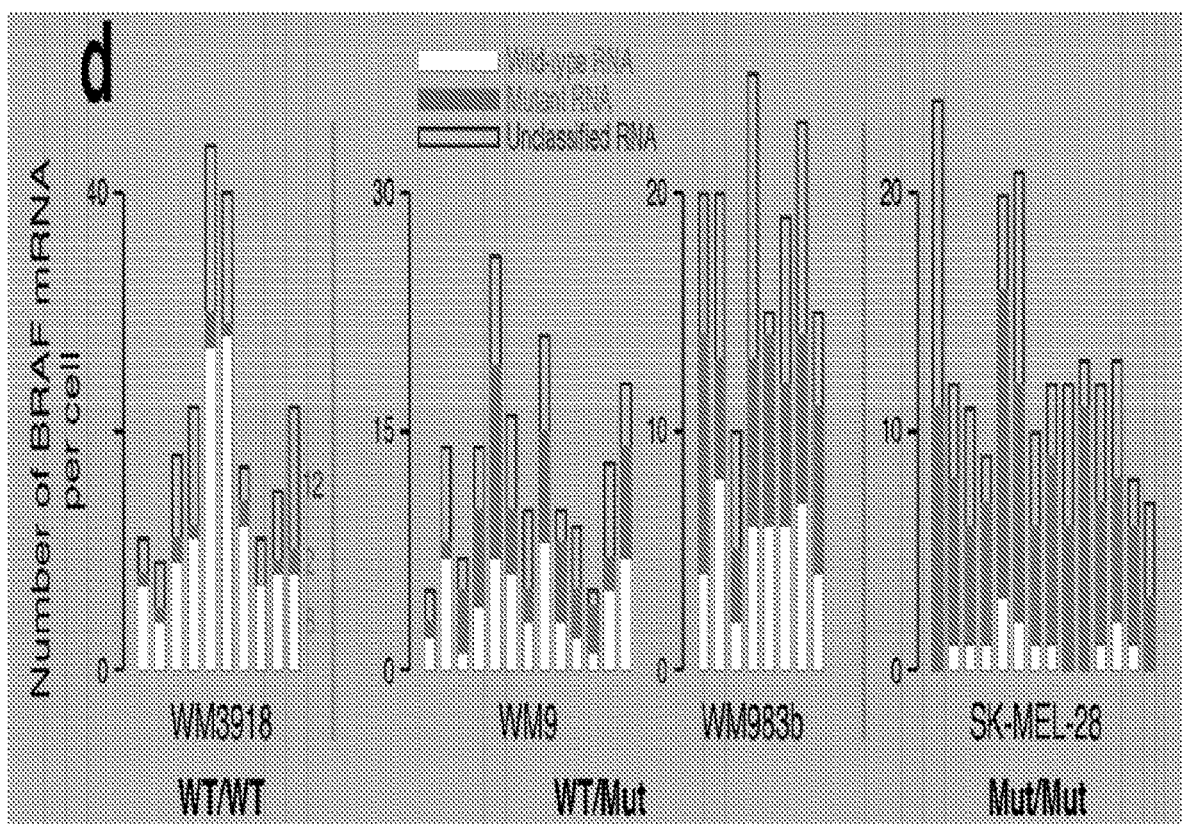

SEQUENCE LISTING

<160> NUMBER OF SEQ ID NOS: 767

<210> SEQ ID NO 1
<211> LENGTH: 20
<212> TYPE: DNA
<213> ORGANISM: Artificial Sequence
<220> FEATURE:
<223> OTHER INFORMATION: Synthetic Probe

<400> SEQUENCE: 1
gaggaaaagc tcgtggtcag                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic Probe

<400> SEQUENCE: 2
gatctgtgtt ggcttctcaa                                          20

<210> SEQ ID NO 3
<211> LENGTH: 20
<212> TYPE: DNA
<213> ORGANISM: Artificial Sequence
<220> FEATURE:
<223> OTHER INFORMATION: Synthetic Probe

<400> SEQUENCE: 3
gagattccga gttcgaagaa                                          20

<210> SEQ ID NO 4
<211> LENGTH: 20
<212> TYPE: DNA
<213> ORGANISM: Artificial Sequence
<220> FEATURE:
<223> OTHER INFORMATION: Synthetic Probe

<400> SEQUENCE: 4
tgtgcaaaaa tattggtgct                                          20

<210> SEQ ID NO 5
<211> LENGTH: 20
<212> TYPE: DNA
<213> ORGANISM: Artificial Sequence
<220> FEATURE:
<223> OTHER INFORMATION: Synthetic Probe

<400> SEQUENCE: 5
tctggagttt cgatgagaca                                          20

```
<210> SEQ ID NO 6
<211> LENGTH: 20
<212> TYPE: DNA
<213> ORGANISM: Artificial Sequence
<220> FEATURE:
<223> OTHER INFORMATION: Synthetic Probe

<400> SEQUENCE: 6
tgagattctt gctctccttt                                                  20

<210> SEQ ID NO 7
<211> LENGTH: 20
<212> TYPE: DNA
<213> ORGANISM: Artificial Sequence
<220> FEATURE:
<223> OTHER INFORMATION: Synthetic Probe

<400> SEQUENCE: 7
ctgcaaatga gctgacaagc                                                  20

<210> SEQ ID NO 8
<211> LENGTH: 20
<212> TYPE: DNA
<213> ORGANISM: Artificial Sequence
<220> FEATURE:
<223> OTHER INFORMATION: Synthetic Probe

<400> SEQUENCE: 8
tggaagaaac cagtaaacgt                                                  20

<210> SEQ ID NO 9
<211> LENGTH: 20
<212> TYPE: DNA
<213> ORGANISM: Artificial Sequence
<220> FEATURE:
<223> OTHER INFORMATION: Synthetic Probe

<400> SEQUENCE: 9
aagagtgaac tgcaacgtag                                                  20

<210> SEQ ID NO 10
<211> LENGTH: 20
<212> TYPE: DNA
<213> ORGANISM: Artificial Sequence
<220> FEATURE:
<223> OTHER INFORMATION: Synthetic Probe

<400> SEQUENCE: 10
gcaataggag ccgtagattt                                                  20

<210> SEQ ID NO 11
<211> LENGTH: 20
<212> TYPE: DNA
<213> ORGANISM: Artificial Sequence
<220> FEATURE:
<223> OTHER INFORMATION: Synthetic Probe

<400> SEQUENCE: 11
atttctagtg gcaagaggtt                                                  20

<210> SEQ ID NO 12
<211> LENGTH: 20
<212> TYPE: DNA
<213> ORGANISM: Artificial Sequence
<220> FEATURE:
<223> OTHER INFORMATION: Synthetic Probe
```

<400> SEQUENCE: 12
taactgaacc aggcttgttt                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic Probe

<400> SEQUENCE: 13
acagcaatag tttgagtagg                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic Probe

<400> SEQUENCE: 14
tgttgccttg tattgttgtt                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Probe

<400> SEQUENCE: 15
caggtcatct cttgcttcag                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Probe

<400> SEQUENCE: 16
tcagagtaca ccaagggcaa                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic Probe

<400> SEQUENCE: 17
aaactataaa gtttgcggca                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic Probe

<400> SEQUENCE: 18
tggcagagtt taagatgctt                                              20

<210> SEQ ID NO 19
<211> LENGTH: 20

```
<212> TYPE: DNA
<213> ORGANISM: Artificial Sequence
<220> FEATURE:
<223> OTHER INFORMATION: Synthetic Probe

<400> SEQUENCE: 19
cctagcacct tttggatgat                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Probe

<400> SEQUENCE: 20
ggagccatca taacactcat                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Probe

<400> SEQUENCE: 21
tatcctgagg atttcctgca                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Probe

<400> SEQUENCE: 22
tgcgactaaa agcaaatcca                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic Probe

<400> SEQUENCE: 23
ggtgttctct taactggtcc                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic Probe

<400> SEQUENCE: 24
gcctgcacac aagaatatgt                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic Probe

<400> SEQUENCE: 25
```
catgcttgct tttgttcgtt                                         20

<210> SEQ ID NO 26
<211> LENGTH: 20
<212> TYPE: DNA
<213> ORGANISM: Artificial Sequence
<220> FEATURE:
<223> OTHER INFORMATION: Synthetic Probe

<400> SEQUENCE: 26
ctttgctgtt ctacttcccc                                         20

<210> SEQ ID NO 27
<211> LENGTH: 20
<212> TYPE: DNA
<213> ORGANISM: Artificial Sequence
<220> FEATURE:
<223> OTHER INFORMATION: Synthetic Probe

<400> SEQUENCE: 27
aaatacagac gattgtggcc                                         20

<210> SEQ ID NO 28
<211> LENGTH: 20
<212> TYPE: DNA
<213> ORGANISM: Artificial Sequence
<220> FEATURE:
<223> OTHER INFORMATION: Synthetic Probe

<400> SEQUENCE: 28
agaggtaagc aggtatcact                                         20

<210> SEQ ID NO 29
<211> LENGTH: 20
<212> TYPE: DNA
<213> ORGANISM: Artificial Sequence
<220> FEATURE:
<223> OTHER INFORMATION: Synthetic Probe

<400> SEQUENCE: 29
gacatggaga ttccagagtt                                         20

<210> SEQ ID NO 30
<211> LENGTH: 20
<212> TYPE: DNA
<213> ORGANISM: Artificial Sequence
<220> FEATURE:
<223> OTHER INFORMATION: Synthetic Probe

<400> SEQUENCE: 30
cagcaataaa cccatgcttc                                         20

<210> SEQ ID NO 31
<211> LENGTH: 20
<212> TYPE: DNA
<213> ORGANISM: Artificial Sequence
<220> FEATURE:
<223> OTHER INFORMATION: Synthetic Probe

<400> SEQUENCE: 31
caggcatgat tcatttgatt                                         20

<210> SEQ ID NO 32
<211> LENGTH: 20
<212> TYPE: DNA
<213> ORGANISM: Artificial Sequence

```
<220> FEATURE:
<223> OTHER INFORMATION: Synthetic Probe

<400> SEQUENCE: 32
tgaagcatga agtttcgaca                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic Probe

<400> SEQUENCE: 33
aaagtcatgc atgctgacta                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic Probe

<400> SEQUENCE: 34
catttcacgg agcttggtaa                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic Probe

<400> SEQUENCE: 35
tatttcttcg tttgcagggg                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic Probe

<400> SEQUENCE: 36
ccatttgctg tcccattttg                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic Probe

<400> SEQUENCE: 37
ctgttttgaa acccctgaga                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic Probe

<400> SEQUENCE: 38
acatggggtt agagcttttc                                               20
```

```
<210> SEQ ID NO 39
<211> LENGTH: 20
<212> TYPE: DNA
<213> ORGANISM: Artificial Sequence
<220> FEATURE:
<223> OTHER INFORMATION: Synthetic Probe

<400> SEQUENCE: 39
agaggatgaa ttccctaaaa                                          20

<210> SEQ ID NO 40
<211> LENGTH: 20
<212> TYPE: DNA
<213> ORGANISM: Artificial Sequence
<220> FEATURE:
<223> OTHER INFORMATION: Synthetic Probe

<400> SEQUENCE: 40
tgaagtagaa ccctgataca                                          20

<210> SEQ ID NO 41
<211> LENGTH: 20
<212> TYPE: DNA
<213> ORGANISM: Artificial Sequence
<220> FEATURE:
<223> OTHER INFORMATION: Synthetic Probe

<400> SEQUENCE: 41
cctccccaag aaaatgtctc                                          20

<210> SEQ ID NO 42
<211> LENGTH: 20
<212> TYPE: DNA
<213> ORGANISM: Artificial Sequence
<220> FEATURE:
<223> OTHER INFORMATION: Synthetic Probe

<400> SEQUENCE: 42
aggatcaaag tttgactgca                                          20

<210> SEQ ID NO 43
<211> LENGTH: 20
<212> TYPE: DNA
<213> ORGANISM: Artificial Sequence
<220> FEATURE:
<223> OTHER INFORMATION: Synthetic Probe

<400> SEQUENCE: 43
gggtgagcaa tgcactaaaa                                          20

<210> SEQ ID NO 44
<211> LENGTH: 20
<212> TYPE: DNA
<213> ORGANISM: Artificial Sequence
<220> FEATURE:
<223> OTHER INFORMATION: Synthetic Probe

<400> SEQUENCE: 44
caaatgcgtt ctttccttgg                                          20

<210> SEQ ID NO 45
<211> LENGTH: 20
<212> TYPE: DNA
<213> ORGANISM: Artificial Sequence
<220> FEATURE:
<223> OTHER INFORMATION: Synthetic Probe
```

<400> SEQUENCE: 45
ttctcccctt ataagtgaca                                          20

<210> SEQ ID NO 46
<211> LENGTH: 20
<212> TYPE: DNA
<213> ORGANISM: Artificial Sequence
<220> FEATURE:
<223> OTHER INFORMATION: Synthetic Probe

<400> SEQUENCE: 46
acacatataa cacagggcaa                                          20

<210> SEQ ID NO 47
<211> LENGTH: 20
<212> TYPE: DNA
<213> ORGANISM: Artificial Sequence
<220> FEATURE:
<223> OTHER INFORMATION: Synthetic Probe

<400> SEQUENCE: 47
caactgcaaa tatgtgcgtg                                          20

<210> SEQ ID NO 48
<211> LENGTH: 20
<212> TYPE: DNA
<213> ORGANISM: Artificial Sequence
<220> FEATURE:
<223> OTHER INFORMATION: Synthetic Probe

<400> SEQUENCE: 48
tgcttgttaa tgtgccagta                                          20

<210> SEQ ID NO 49
<211> LENGTH: 20
<212> TYPE: DNA
<213> ORGANISM: Artificial Sequence
<220> FEATURE:
<223> OTHER INFORMATION: Synthetic Probe

<400> SEQUENCE: 49
cggagttgga ataaaaacct                                          20

<210> SEQ ID NO 50
<211> LENGTH: 20
<212> TYPE: DNA
<213> ORGANISM: Artificial Sequence
<220> FEATURE:
<223> OTHER INFORMATION: Synthetic Probe

<400> SEQUENCE: 50
gatgttactc aaccacagtg                                          20

<210> SEQ ID NO 51
<211> LENGTH: 20
<212> TYPE: DNA
<213> ORGANISM: Artificial Sequence
<220> FEATURE:
<223> OTHER INFORMATION: Synthetic Probe

<400> SEQUENCE: 51
acacatctta aagaccagtc                                          20

<210> SEQ ID NO 52

```
<211> LENGTH: 20
<212> TYPE: DNA
<213> ORGANISM: Artificial Sequence
<220> FEATURE:
<223> OTHER INFORMATION: Synthetic Probe

<400> SEQUENCE: 52
tcgttaaata gcctcacagt                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic Probe

<400> SEQUENCE: 53
tgacaaatca catccacact                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic Probe

<400> SEQUENCE: 54
aatgaaagct gcagtttccc                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic Probe

<400> SEQUENCE: 55
gcttaccaat caaggaatct                                              20

<210> SEQ ID NO 56
<211> LENGTH: 20
<212> TYPE: DNA
<213> ORGANISM: Artificial Sequence
<220> FEATURE:
<223> OTHER INFORMATION: Synthetic Probe

<400> SEQUENCE: 56
ccagaggcaa aaatcagagt                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic Probe

<400> SEQUENCE: 57
cgagataaac gctcgagatc                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic Probe

<400> SEQUENCE: 58
```
tatgtgcaca gctttagcaa                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic Probe

<400> SEQUENCE: 59
ttctacacct acatctcccc                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic Probe

<400> SEQUENCE: 60
agcattaaga gcataactgc                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic Probe

<400> SEQUENCE: 61
gcaaacaatg ctagccttct                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic Probe

<400> SEQUENCE: 62
ggtgggaatc accaactttt                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic Probe

<400> SEQUENCE: 63
gataccctgt gcagaaggat                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic Probe

<400> SEQUENCE: 64
gatgtaccaa acggagagag                                              20

<210> SEQ ID NO 65
<211> LENGTH: 20
<212> TYPE: DNA

```
<213> ORGANISM: Artificial Sequence
<220> FEATURE:
<223> OTHER INFORMATION: Synthetic Probe

<400> SEQUENCE: 65
cattcacttc ccggttgtaa                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic Probe

<400> SEQUENCE: 66
ttggttcccg ttttctagac                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic Probe

<400> SEQUENCE: 67
ctctacgggc ttcacttctt                                              20

<210> SEQ ID NO 68
<211> LENGTH: 20
<212> TYPE: DNA
<213> ORGANISM: Artificial Sequence
<220> FEATURE:
<223> OTHER INFORMATION: Synthetic Probe

<400> SEQUENCE: 68
gaggtttgga aagggtttg                                               20

<210> SEQ ID NO 69
<211> LENGTH: 20
<212> TYPE: DNA
<213> ORGANISM: Artificial Sequence
<220> FEATURE:
<223> OTHER INFORMATION: Synthetic Probe

<400> SEQUENCE: 69
ctggtctttg tcttcttcct                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic Probe

<400> SEQUENCE: 70
cgttctctgg atgtaactct                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic Probe

<400> SEQUENCE: 71
tttctcgtct ccatcttcgt                                              20
```

<210> SEQ ID NO 72
<211> LENGTH: 20
<212> TYPE: DNA
<213> ORGANISM: Artificial Sequence
<220> FEATURE:
<223> OTHER INFORMATION: Synthetic Probe

<400> SEQUENCE: 72
gttttgcgtc tcttctcctc                                           20

<210> SEQ ID NO 73
<211> LENGTH: 20
<212> TYPE: DNA
<213> ORGANISM: Artificial Sequence
<220> FEATURE:
<223> OTHER INFORMATION: Synthetic Probe

<400> SEQUENCE: 73
agttcatgac tgttttggcg                                           20

<210> SEQ ID NO 74
<211> LENGTH: 20
<212> TYPE: DNA
<213> ORGANISM: Artificial Sequence
<220> FEATURE:
<223> OTHER INFORMATION: Synthetic Probe

<400> SEQUENCE: 74
agcttctcat ttgtcagcat                                           20

<210> SEQ ID NO 75
<211> LENGTH: 20
<212> TYPE: DNA
<213> ORGANISM: Artificial Sequence
<220> FEATURE:
<223> OTHER INFORMATION: Synthetic Probe

<400> SEQUENCE: 75
gactcgttgg catcaaagat                                           20

<210> SEQ ID NO 76
<211> LENGTH: 20
<212> TYPE: DNA
<213> ORGANISM: Artificial Sequence
<220> FEATURE:
<223> OTHER INFORMATION: Synthetic Probe

<400> SEQUENCE: 76
ctgaagcagg tcagtttgtg                                           20

<210> SEQ ID NO 77
<211> LENGTH: 20
<212> TYPE: DNA
<213> ORGANISM: Artificial Sequence
<220> FEATURE:
<223> OTHER INFORMATION: Synthetic Probe

<400> SEQUENCE: 77
gtgaccgtgc ttacagtaca                                           20

<210> SEQ ID NO 78
<211> LENGTH: 20
<212> TYPE: DNA
<213> ORGANISM: Artificial Sequence
<220> FEATURE:

<223> OTHER INFORMATION: Synthetic Probe

<400> SEQUENCE: 78
tattcttctc gatgaggccg                                        20

<210> SEQ ID NO 79
<211> LENGTH: 20
<212> TYPE: DNA
<213> ORGANISM: Artificial Sequence
<220> FEATURE:
<223> OTHER INFORMATION: Synthetic Probe

<400> SEQUENCE: 79
ctccatcaaa gccagtgatc                                        20

<210> SEQ ID NO 80
<211> LENGTH: 20
<212> TYPE: DNA
<213> ORGANISM: Artificial Sequence
<220> FEATURE:
<223> OTHER INFORMATION: Synthetic Probe

<400> SEQUENCE: 80
ccatcagaat gtattcggca                                        20

<210> SEQ ID NO 81
<211> LENGTH: 20
<212> TYPE: DNA
<213> ORGANISM: Artificial Sequence
<220> FEATURE:
<223> OTHER INFORMATION: Synthetic Probe

<400> SEQUENCE: 81
caaatatggg cgcatactcg                                        20

<210> SEQ ID NO 82
<211> LENGTH: 20
<212> TYPE: DNA
<213> ORGANISM: Artificial Sequence
<220> FEATURE:
<223> OTHER INFORMATION: Synthetic Probe

<400> SEQUENCE: 82
tcataggtcg agtcggaatt                                        20

<210> SEQ ID NO 83
<211> LENGTH: 20
<212> TYPE: DNA
<213> ORGANISM: Artificial Sequence
<220> FEATURE:
<223> OTHER INFORMATION: Synthetic Probe

<400> SEQUENCE: 83
ctcgatcttg ttgatcaggt                                        20

<210> SEQ ID NO 84
<211> LENGTH: 20
<212> TYPE: DNA
<213> ORGANISM: Artificial Sequence
<220> FEATURE:
<223> OTHER INFORMATION: Synthetic Probe

<400> SEQUENCE: 84
gttcaagttg aggccagaag                                        20

```
<210> SEQ ID NO 85
<211> LENGTH: 20
<212> TYPE: DNA
<213> ORGANISM: Artificial Sequence
<220> FEATURE:
<223> OTHER INFORMATION: Synthetic Probe

<400> SEQUENCE: 85
ctcgtcataa ctctccacct                                            20

<210> SEQ ID NO 86
<211> LENGTH: 20
<212> TYPE: DNA
<213> ORGANISM: Artificial Sequence
<220> FEATURE:
<223> OTHER INFORMATION: Synthetic Probe

<400> SEQUENCE: 86
gtagaatgcc tgatggtctg                                            20

<210> SEQ ID NO 87
<211> LENGTH: 20
<212> TYPE: DNA
<213> ORGANISM: Artificial Sequence
<220> FEATURE:
<223> OTHER INFORMATION: Synthetic Probe

<400> SEQUENCE: 87 cctttcaat ttgctctgcg                                             20

<210> SEQ ID NO 88
<211> LENGTH: 20
<212> TYPE: DNA
<213> ORGANISM: Artificial Sequence
<220> FEATURE:
<223> OTHER INFORMATION: Synthetic Probe

<400> SEQUENCE: 88
cttaaaggcg ttctccttgt                                            20

<210> SEQ ID NO 89
<211> LENGTH: 20
<212> TYPE: DNA
<213> ORGANISM: Artificial Sequence
<220> FEATURE:
<223> OTHER INFORMATION: Synthetic Probe

<400> SEQUENCE: 89
tccactgcca ccaaatttaa                                            20

<210> SEQ ID NO 90
<211> LENGTH: 20
<212> TYPE: DNA
<213> ORGANISM: Artificial Sequence
<220> FEATURE:
<223> OTHER INFORMATION: Synthetic Probe

<400> SEQUENCE: 90
cttcatggcc atattgggac                                            20

<210> SEQ ID NO 91
<211> LENGTH: 20
<212> TYPE: DNA
<213> ORGANISM: Artificial Sequence
<220> FEATURE:
<223> OTHER INFORMATION: Synthetic Probe
```

```
<400> SEQUENCE: 91
gacttcctca tcgtcatctg                                               20

<210> SEQ ID NO 92
<211> LENGTH: 20
<212> TYPE: DNA
<213> ORGANISM: Artificial Sequence
<220> FEATURE:
<223> OTHER INFORMATION: Synthetic Probe

<400> SEQUENCE: 92
ggcatctctg ggatgttatc                                               20

<210> SEQ ID NO 93
<211> LENGTH: 20
<212> TYPE: DNA
<213> ORGANISM: Artificial Sequence
<220> FEATURE:
<223> OTHER INFORMATION: Synthetic Probe

<400> SEQUENCE: 93
cttctccgac ccaagagatg                                               20

<210> SEQ ID NO 94
<211> LENGTH: 20
<212> TYPE: DNA
<213> ORGANISM: Artificial Sequence
<220> FEATURE:
<223> OTHER INFORMATION: Synthetic Probe

<400> SEQUENCE: 94
ttgatattcc acacctcctc                                               20

<210> SEQ ID NO 95
<211> LENGTH: 20
<212> TYPE: DNA
<213> ORGANISM: Artificial Sequence
<220> FEATURE:
<223> OTHER INFORMATION: Synthetic Probe

<400> SEQUENCE: 95
tgtccaatag ggcctctata                                               20

<210> SEQ ID NO 96
<211> LENGTH: 20
<212> TYPE: DNA
<213> ORGANISM: Artificial Sequence
<220> FEATURE:
<223> OTHER INFORMATION: Synthetic Probe

<400> SEQUENCE: 96
gctggtgtat tcttcatagg                                               20

<210> SEQ ID NO 97
<211> LENGTH: 20
<212> TYPE: DNA
<213> ORGANISM: Artificial Sequence
<220> FEATURE:
<223> OTHER INFORMATION: Synthetic Probe

<400> SEQUENCE: 97
tctttgttgg agtgcatcta                                               20

<210> SEQ ID NO 98
<211> LENGTH: 20
```

```
<212> TYPE: DNA
<213> ORGANISM: Artificial Sequence
<220> FEATURE:
<223> OTHER INFORMATION: Synthetic Probe

<400> SEQUENCE: 98
gttccccaga gattccaata                                                 20

<210> SEQ ID NO 99
<211> LENGTH: 20
<212> TYPE: DNA
<213> ORGANISM: Artificial Sequence
<220> FEATURE:
<223> OTHER INFORMATION: Synthetic Probe

<400> SEQUENCE: 99
gtatccattg atgcagagct                                                 20

<210> SEQ ID NO 100
<211> LENGTH: 20
<212> TYPE: DNA
<213> ORGANISM: Artificial Sequence
<220> FEATURE:
<223> OTHER INFORMATION: Synthetic Probe

<400> SEQUENCE: 100
ttgttgggca ggaagactct                                                 20

<210> SEQ ID NO 101
<211> LENGTH: 20
<212> TYPE: DNA
<213> ORGANISM: Artificial Sequence
<220> FEATURE:
<223> OTHER INFORMATION: Synthetic Probe

<400> SEQUENCE: 101
actgtaactc cacaccttgc                                                 20

<210> SEQ ID NO 102
<211> LENGTH: 20
<212> TYPE: DNA
<213> ORGANISM: Artificial Sequence
<220> FEATURE:
<223> OTHER INFORMATION: Synthetic Probe

<400> SEQUENCE: 102
agtgctttct ttagactgtc                                                 20

<210> SEQ ID NO 103
<211> LENGTH: 20
<212> TYPE: DNA
<213> ORGANISM: Artificial Sequence
<220> FEATURE:
<223> OTHER INFORMATION: Synthetic Probe

<400> SEQUENCE: 103
ttctctccat cctgaattct                                                 20

<210> SEQ ID NO 104
<211> LENGTH: 20
<212> TYPE: DNA
<213> ORGANISM: Artificial Sequence
<220> FEATURE:
<223> OTHER INFORMATION: Synthetic Probe

<400> SEQUENCE: 104
```
agtgtcccaa ccaattggtt                                                    20

<210> SEQ ID NO 105
<211> LENGTH: 20
<212> TYPE: DNA
<213> ORGANISM: Artificial Sequence
<220> FEATURE:
<223> OTHER INFORMATION: Synthetic Probe

<400> SEQUENCE: 105
tccacatgca attcttctcc                                                    20

<210> SEQ ID NO 106
<211> LENGTH: 20
<212> TYPE: DNA
<213> ORGANISM: Artificial Sequence
<220> FEATURE:
<223> OTHER INFORMATION: Synthetic Probe

<400> SEQUENCE: 106
tggtattggg tggtgttcaa                                                    20

<210> SEQ ID NO 107
<211> LENGTH: 20
<212> TYPE: DNA
<213> ORGANISM: Artificial Sequence
<220> FEATURE:
<223> OTHER INFORMATION: Synthetic Probe

<400> SEQUENCE: 107
cttcatctgc tggtcggaag                                                    20

<210> SEQ ID NO 108
<211> LENGTH: 20
<212> TYPE: DNA
<213> ORGANISM: Artificial Sequence
<220> FEATURE:
<223> OTHER INFORMATION: Synthetic Probe

<400> SEQUENCE: 108
ggggtagcag acaaacctgt                                                    20

<210> SEQ ID NO 109
<211> LENGTH: 20
<212> TYPE: DNA
<213> ORGANISM: Artificial Sequence
<220> FEATURE:
<223> OTHER INFORMATION: Synthetic Probe

<400> SEQUENCE: 109
tcacgttagt tagtgagcca                                                    20

<210> SEQ ID NO 110
<211> LENGTH: 20
<212> TYPE: DNA
<213> ORGANISM: Artificial Sequence
<220> FEATURE:
<223> OTHER INFORMATION: Synthetic Probe

<400> SEQUENCE: 110
tgaggtcctg gagatttctg                                                    20

<210> SEQ ID NO 111
<211> LENGTH: 20
<212> TYPE: DNA
<213> ORGANISM: Artificial Sequence
<220> FEATURE:
<223> OTHER INFORMATION: Synthetic Probe

<400> SEQUENCE: 111
attcctgtct tctgaggatg                                            20

<210> SEQ ID NO 112
<211> LENGTH: 20
<212> TYPE: DNA
<213> ORGANISM: Artificial Sequence
<220> FEATURE:
<223> OTHER INFORMATION: Synthetic Probe

<400> SEQUENCE: 112
ctcccaatca tcactcgagt                                            20

<210> SEQ ID NO 113
<211> LENGTH: 20
<212> TYPE: DNA
<213> ORGANISM: Artificial Sequence
<220> FEATURE:
<223> OTHER INFORMATION: Synthetic Probe

<400> SEQUENCE: 113
tctttgtccc actgtaatct                                            20

<210> SEQ ID NO 114
<211> LENGTH: 20
<212> TYPE: DNA
<213> ORGANISM: Artificial Sequence
<220> FEATURE:
<223> OTHER INFORMATION: Synthetic Probe

<400> SEQUENCE: 114
ttcactgcca catcaccatg                                            20

<210> SEQ ID NO 115
<211> LENGTH: 20
<212> TYPE: DNA
<213> ORGANISM: Artificial Sequence
<220> FEATURE:
<223> OTHER INFORMATION: Synthetic Probe

<400> SEQUENCE: 115
gtaggtgctg tcacattcaa                                            20

<210> SEQ ID NO 116
<211> LENGTH: 20
<212> TYPE: DNA
<213> ORGANISM: Artificial Sequence
<220> FEATURE:
<223> OTHER INFORMATION: Synthetic Probe

<400> SEQUENCE: 116
tcacatgtcg tgttttcctg                                            20

<210> SEQ ID NO 117
<211> LENGTH: 20
<212> TYPE: DNA
<213> ORGANISM: Artificial Sequence
<220> FEATURE:
<223> OTHER INFORMATION: Synthetic Probe

<400> SEQUENCE: 117
caatagccag ttgtggcttt                                            20

```
<210> SEQ ID NO 118
<211> LENGTH: 20
<212> TYPE: DNA
<213> ORGANISM: Artificial Sequence
<220> FEATURE:
<223> OTHER INFORMATION: Synthetic Probe

<400> SEQUENCE: 118
tggtgataca agctggagcc                                                 20

<210> SEQ ID NO 119
<211> LENGTH: 20
<212> TYPE: DNA
<213> ORGANISM: Artificial Sequence
<220> FEATURE:
<223> OTHER INFORMATION: Synthetic Probe

<400> SEQUENCE: 119
gcattctgat gacttctggt                                                 20

<210> SEQ ID NO 120
<211> LENGTH: 20
<212> TYPE: DNA
<213> ORGANISM: Artificial Sequence
<220> FEATURE:
<223> OTHER INFORMATION: Synthetic Probe

<400> SEQUENCE: 120
tccctgttgt tgatgtttga                                                 20

<210> SEQ ID NO 121
<211> LENGTH: 20
<212> TYPE: DNA
<213> ORGANISM: Artificial Sequence
<220> FEATURE:
<223> OTHER INFORMATION: Synthetic Probe

<400> SEQUENCE: 121
gcttttggac agttactccg                                                 20

<210> SEQ ID NO 122
<211> LENGTH: 20
<212> TYPE: DNA
<213> ORGANISM: Artificial Sequence
<220> FEATURE:
<223> OTHER INFORMATION: Synthetic Probe

<400> SEQUENCE: 122
tcaaggaggg ttctgatgca                                                 20

<210> SEQ ID NO 123
<211> LENGTH: 20
<212> TYPE: DNA
<213> ORGANISM: Artificial Sequence
<220> FEATURE:
<223> OTHER INFORMATION: Synthetic Probe

<400> SEQUENCE: 123
tcctctgttt ggaaaccagc                                                 20

<210> SEQ ID NO 124
<211> LENGTH: 20
<212> TYPE: DNA
<213> ORGANISM: Artificial Sequence
<220> FEATURE:
<223> OTHER INFORMATION: Synthetic Probe
```

```
<400> SEQUENCE: 124
tcctgaactc tctcactcat                                           20

<210> SEQ ID NO 125
<211> LENGTH: 20
<212> TYPE: DNA
<213> ORGANISM: Artificial Sequence
<220> FEATURE:
<223> OTHER INFORMATION: Synthetic Probe

<400> SEQUENCE: 125
aagcctctag aagaggctct                                           20

<210> SEQ ID NO 126
<211> LENGTH: 20
<212> TYPE: DNA
<213> ORGANISM: Artificial Sequence
<220> FEATURE:
<223> OTHER INFORMATION: Synthetic Probe

<400> SEQUENCE: 126
atctgttcag tttgccttat                                           20

<210> SEQ ID NO 127
<211> LENGTH: 20
<212> TYPE: DNA
<213> ORGANISM: Artificial Sequence
<220> FEATURE:
<223> OTHER INFORMATION: Synthetic Probe

<400> SEQUENCE: 127
atcttcaaag tcgctttcct                                           20

<210> SEQ ID NO 128
<211> LENGTH: 20
<212> TYPE: DNA
<213> ORGANISM: Artificial Sequence
<220> FEATURE:
<223> OTHER INFORMATION: Synthetic Probe

<400> SEQUENCE: 128
catcatcctt tagagtctga                                           20

<210> SEQ ID NO 129
<211> LENGTH: 20
<212> TYPE: DNA
<213> ORGANISM: Artificial Sequence
<220> FEATURE:
<223> OTHER INFORMATION: Synthetic Probe

<400> SEQUENCE: 129
ccttcttgat tttccaatct                                           20

<210> SEQ ID NO 130
<211> LENGTH: 20
<212> TYPE: DNA
<213> ORGANISM: Artificial Sequence
<220> FEATURE:
<223> OTHER INFORMATION: Synthetic Probe

<400> SEQUENCE: 130
gtacttttgt tgcctttatg                                           20

<210> SEQ ID NO 131
```

```
<211> LENGTH: 20
<212> TYPE: DNA
<213> ORGANISM: Artificial Sequence
<220> FEATURE:
<223> OTHER INFORMATION: Synthetic Probe

<400> SEQUENCE: 131
gacacgtgga ctatatccat                                                    20

<210> SEQ ID NO 132
<211> LENGTH: 20
<212> TYPE: DNA
<213> ORGANISM: Artificial Sequence
<220> FEATURE:
<223> OTHER INFORMATION: Synthetic Probe

<400> SEQUENCE: 132
tcttgctcgt gtactgaatt                                                    20

<210> SEQ ID NO 133
<211> LENGTH: 20
<212> TYPE: DNA
<213> ORGANISM: Artificial Sequence
<220> FEATURE:
<223> OTHER INFORMATION: Synthetic Probe

<400> SEQUENCE: 133
ctctgggtca gagttaatgg                                                    20

<210> SEQ ID NO 134
<211> LENGTH: 20
<212> TYPE: DNA
<213> ORGANISM: Artificial Sequence
<220> FEATURE:
<223> OTHER INFORMATION: Synthetic Probe

<400> SEQUENCE: 134
atctttcaca tcagtcttct                                                    20

<210> SEQ ID NO 135
<211> LENGTH: 20
<212> TYPE: DNA
<213> ORGANISM: Artificial Sequence
<220> FEATURE:
<223> OTHER INFORMATION: Synthetic Probe

<400> SEQUENCE: 135
cttgcaacag gaggatcaga                                                    20

<210> SEQ ID NO 136
<211> LENGTH: 20
<212> TYPE: DNA
<213> ORGANISM: Artificial Sequence
<220> FEATURE:
<223> OTHER INFORMATION: Synthetic Probe

<400> SEQUENCE: 136
actacgtgga gacttctcag                                                    20

<210> SEQ ID NO 137
<211> LENGTH: 20
<212> TYPE: DNA
<213> ORGANISM: Artificial Sequence
<220> FEATURE:
<223> OTHER INFORMATION: Synthetic Probe

<400> SEQUENCE: 137
```
tgtggagggt ttggtagaac                                              20

<210> SEQ ID NO 138
<211> LENGTH: 20
<212> TYPE: DNA
<213> ORGANISM: Artificial Sequence
<220> FEATURE:
<223> OTHER INFORMATION: Synthetic Probe

<400> SEQUENCE: 138
ctcttcctta tagttgttca                                              20

<210> SEQ ID NO 139
<211> LENGTH: 20
<212> TYPE: DNA
<213> ORGANISM: Artificial Sequence
<220> FEATURE:
<223> OTHER INFORMATION: Synthetic Probe

<400> SEQUENCE: 139
agtgattgtt tggtaggtgg                                              20

<210> SEQ ID NO 140
<211> LENGTH: 20
<212> TYPE: DNA
<213> ORGANISM: Artificial Sequence
<220> FEATURE:
<223> OTHER INFORMATION: Synthetic Probe

<400> SEQUENCE: 140
gtgcacattt tggagttttt                                              20

<210> SEQ ID NO 141
<211> LENGTH: 20
<212> TYPE: DNA
<213> ORGANISM: Artificial Sequence
<220> FEATURE:
<223> OTHER INFORMATION: Synthetic Probe

<400> SEQUENCE: 141
tcccattgtg taatcttcat                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic Probe

<400> SEQUENCE: 142
cctcactttt attattcctc                                              20

<210> SEQ ID NO 143
<211> LENGTH: 20
<212> TYPE: DNA
<213> ORGANISM: Artificial Sequence
<220> FEATURE:
<223> OTHER INFORMATION: Synthetic Probe

<400> SEQUENCE: 143
ctggattctg tatctatggc                                              20

<210> SEQ ID NO 144
<211> LENGTH: 20
<212> TYPE: DNA

```
<213> ORGANISM: Artificial Sequence
<220> FEATURE:
<223> OTHER INFORMATION: Synthetic Probe

<400> SEQUENCE: 144
gctgggagtg gcaaaaacat                                                 20

<210> SEQ ID NO 145
<211> LENGTH: 20
<212> TYPE: DNA
<213> ORGANISM: Artificial Sequence
<220> FEATURE:
<223> OTHER INFORMATION: Synthetic Probe

<400> SEQUENCE: 145
ccaggagtac agaatgtagg                                                 20

<210> SEQ ID NO 146
<211> LENGTH: 20
<212> TYPE: DNA
<213> ORGANISM: Artificial Sequence
<220> FEATURE:
<223> OTHER INFORMATION: Synthetic Probe

<400> SEQUENCE: 146
gtggatacca aagctatgct                                                 20

<210> SEQ ID NO 147
<211> LENGTH: 20
<212> TYPE: DNA
<213> ORGANISM: Artificial Sequence
<220> FEATURE:
<223> OTHER INFORMATION: Synthetic Probe

<400> SEQUENCE: 147
agtacgatct tcaacttcca                                                 20

<210> SEQ ID NO 148
<211> LENGTH: 20
<212> TYPE: DNA
<213> ORGANISM: Artificial Sequence
<220> FEATURE:
<223> OTHER INFORMATION: Synthetic Probe

<400> SEQUENCE: 148
cgtaggtgaa gagggatctg                                                 20

<210> SEQ ID NO 149
<211> LENGTH: 20
<212> TYPE: DNA
<213> ORGANISM: Artificial Sequence
<220> FEATURE:
<223> OTHER INFORMATION: Synthetic Probe

<400> SEQUENCE: 149
gcagggcaat gtgaatgtta                                                 20

<210> SEQ ID NO 150
<211> LENGTH: 20
<212> TYPE: DNA
<213> ORGANISM: Artificial Sequence
<220> FEATURE:
<223> OTHER INFORMATION: Synthetic Probe

<400> SEQUENCE: 150
ggtcaacgtt taaaggggga                                                 20
```

```
<210> SEQ ID NO 151
<211> LENGTH: 20
<212> TYPE: DNA
<213> ORGANISM: Artificial Sequence
<220> FEATURE:
<223> OTHER INFORMATION: Synthetic Probe

<400> SEQUENCE: 151
atgactgggc tacatgtcaa                                              20

<210> SEQ ID NO 152
<211> LENGTH: 20
<212> TYPE: DNA
<213> ORGANISM: Artificial Sequence
<220> FEATURE:
<223> OTHER INFORMATION: Synthetic Probe

<400> SEQUENCE: 152
ctacttcctg gtactactta                                              20

<210> SEQ ID NO 153
<211> LENGTH: 20
<212> TYPE: DNA
<213> ORGANISM: Artificial Sequence
<220> FEATURE:
<223> OTHER INFORMATION: Synthetic Probe

<400> SEQUENCE: 153
cagacagcac tgagcaagta                                              20

<210> SEQ ID NO 154
<211> LENGTH: 20
<212> TYPE: DNA
<213> ORGANISM: Artificial Sequence
<220> FEATURE:
<223> OTHER INFORMATION: Synthetic Probe

<400> SEQUENCE: 154
ctccaatggt cacagtatat                                              20

<210> SEQ ID NO 155
<211> LENGTH: 20
<212> TYPE: DNA
<213> ORGANISM: Artificial Sequence
<220> FEATURE:
<223> OTHER INFORMATION: Synthetic Probe

<400> SEQUENCE: 155
aactctcaac ctgacagcag                                              20

<210> SEQ ID NO 156
<211> LENGTH: 20
<212> TYPE: DNA
<213> ORGANISM: Artificial Sequence
<220> FEATURE:
<223> OTHER INFORMATION: Synthetic Probe

<400> SEQUENCE: 156
aagagaaaag accccacac                                               20

<210> SEQ ID NO 157
<211> LENGTH: 20
<212> TYPE: DNA
<213> ORGANISM: Artificial Sequence
<220> FEATURE:
```

<223> OTHER INFORMATION: Synthetic Probe

<400> SEQUENCE: 157
cagctgccat gtgatagaaa                                       20

<210> SEQ ID NO 158
<211> LENGTH: 20
<212> TYPE: DNA
<213> ORGANISM: Artificial Sequence
<220> FEATURE:
<223> OTHER INFORMATION: Synthetic Probe

<400> SEQUENCE: 158
aaattcaggg tctactgggt                                       20

<210> SEQ ID NO 159
<211> LENGTH: 20
<212> TYPE: DNA
<213> ORGANISM: Artificial Sequence
<220> FEATURE:
<223> OTHER INFORMATION: Synthetic Probe

<400> SEQUENCE: 159
catagctaac agtgcacagg                                       20

<210> SEQ ID NO 160
<211> LENGTH: 20
<212> TYPE: DNA
<213> ORGANISM: Artificial Sequence
<220> FEATURE:
<223> OTHER INFORMATION: Synthetic Probe

<400> SEQUENCE: 160
taagcaggtc aacctgaagc                                       20

<210> SEQ ID NO 161
<211> LENGTH: 20
<212> TYPE: DNA
<213> ORGANISM: Artificial Sequence
<220> FEATURE:
<223> OTHER INFORMATION: Synthetic Probe

<400> SEQUENCE: 161
aatcagaagg atcgtaggcc                                       20

<210> SEQ ID NO 162
<211> LENGTH: 20
<212> TYPE: DNA
<213> ORGANISM: Artificial Sequence
<220> FEATURE:
<223> OTHER INFORMATION: Synthetic Probe

<400> SEQUENCE: 162
cggtacacag tgaaaggctg                                       20

<210> SEQ ID NO 163
<211> LENGTH: 20
<212> TYPE: DNA
<213> ORGANISM: Artificial Sequence
<220> FEATURE:
<223> OTHER INFORMATION: Synthetic Probe

<400> SEQUENCE: 163
ctctgctcaa aactgagcga                                       20

```
<210> SEQ ID NO 164
<211> LENGTH: 20
<212> TYPE: DNA
<213> ORGANISM: Artificial Sequence
<220> FEATURE:
<223> OTHER INFORMATION: Synthetic Probe

<400> SEQUENCE: 164
aagttggatt tccgcagatt                                                   20

<210> SEQ ID NO 165
<211> LENGTH: 20
<212> TYPE: DNA
<213> ORGANISM: Artificial Sequence
<220> FEATURE:
<223> OTHER INFORMATION: Synthetic Probe

<400> SEQUENCE: 165
tattggtctt ttcgctgttg                                                   20

<210> SEQ ID NO 166
<211> LENGTH: 20
<212> TYPE: DNA
<213> ORGANISM: Artificial Sequence
<220> FEATURE:
<223> OTHER INFORMATION: Synthetic Probe

<400> SEQUENCE: 166
tatcccattg ctgtagagaa                                                   20

<210> SEQ ID NO 167
<211> LENGTH: 20
<212> TYPE: DNA
<213> ORGANISM: Artificial Sequence
<220> FEATURE:
<223> OTHER INFORMATION: Synthetic Probe

<400> SEQUENCE: 167
tcaatgaggc gcacgtagaa                                                   20

<210> SEQ ID NO 168
<211> LENGTH: 20
<212> TYPE: DNA
<213> ORGANISM: Artificial Sequence
<220> FEATURE:
<223> OTHER INFORMATION: Synthetic Probe

<400> SEQUENCE: 168
acactatggc ttgttttgtc                                                   20

<210> SEQ ID NO 169
<211> LENGTH: 20
<212> TYPE: DNA
<213> ORGANISM: Artificial Sequence
<220> FEATURE:
<223> OTHER INFORMATION: Synthetic Probe

<400> SEQUENCE: 169
caagactcgg cacatttctg                                                   20

<210> SEQ ID NO 170
<211> LENGTH: 20
<212> TYPE: DNA
<213> ORGANISM: Artificial Sequence
<220> FEATURE:
<223> OTHER INFORMATION: Synthetic Probe
```

```
<400> SEQUENCE: 170
ttttcttgtc acaacagcgg                                                  20

<210> SEQ ID NO 171
<211> LENGTH: 20
<212> TYPE: DNA
<213> ORGANISM: Artificial Sequence
<220> FEATURE:
<223> OTHER INFORMATION: Synthetic Probe

<400> SEQUENCE: 171
atctgaggga gtctcatttc                                                  20

<210> SEQ ID NO 172
<211> LENGTH: 20
<212> TYPE: DNA
<213> ORGANISM: Artificial Sequence
<220> FEATURE:
<223> OTHER INFORMATION: Synthetic Probe

<400> SEQUENCE: 172
tgatggcttt gatacaggga                                                  20

<210> SEQ ID NO 173
<211> LENGTH: 20
<212> TYPE: DNA
<213> ORGANISM: Artificial Sequence
<220> FEATURE:
<223> OTHER INFORMATION: Synthetic Probe

<400> SEQUENCE: 173
aatgaccttc tgtaacctct                                                  20

<210> SEQ ID NO 174
<211> LENGTH: 20
<212> TYPE: DNA
<213> ORGANISM: Artificial Sequence
<220> FEATURE:
<223> OTHER INFORMATION: Synthetic Probe

<400> SEQUENCE: 174
tgagtattac ttcctttggc                                                  20

<210> SEQ ID NO 175
<211> LENGTH: 20
<212> TYPE: DNA
<213> ORGANISM: Artificial Sequence
<220> FEATURE:
<223> OTHER INFORMATION: Synthetic Probe

<400> SEQUENCE: 175
atacagtgct tctaccagat                                                  20

<210> SEQ ID NO 176
<211> LENGTH: 20
<212> TYPE: DNA
<213> ORGANISM: Artificial Sequence
<220> FEATURE:
<223> OTHER INFORMATION: Synthetic Probe

<400> SEQUENCE: 176
tccactgaac gaattcacgc                                                  20

<210> SEQ ID NO 177
<211> LENGTH: 20
```

```
<212> TYPE: DNA
<213> ORGANISM: Artificial Sequence
<220> FEATURE:
<223> OTHER INFORMATION: Synthetic Probe

<400> SEQUENCE: 177
gagttatagt tggtctgctg                                              20

<210> SEQ ID NO 178
<211> LENGTH: 20
<212> TYPE: DNA
<213> ORGANISM: Artificial Sequence
<220> FEATURE:
<223> OTHER INFORMATION: Synthetic Probe

<400> SEQUENCE: 178
aattggacat tgcggcagag                                              20

<210> SEQ ID NO 179
<211> LENGTH: 20
<212> TYPE: DNA
<213> ORGANISM: Artificial Sequence
<220> FEATURE:
<223> OTHER INFORMATION: Synthetic Probe

<400> SEQUENCE: 179
ggtgagaagg agaagatgcc                                              20

<210> SEQ ID NO 180
<211> LENGTH: 20
<212> TYPE: DNA
<213> ORGANISM: Artificial Sequence
<220> FEATURE:
<223> OTHER INFORMATION: Synthetic Probe

<400> SEQUENCE: 180
tctgacgact ggtgcgaaag                                              20

<210> SEQ ID NO 181
<211> LENGTH: 20
<212> TYPE: DNA
<213> ORGANISM: Artificial Sequence
<220> FEATURE:
<223> OTHER INFORMATION: Synthetic Probe

<400> SEQUENCE: 181
acaatcatgc cagatatcgc                                              20

<210> SEQ ID NO 182
<211> LENGTH: 20
<212> TYPE: DNA
<213> ORGANISM: Artificial Sequence
<220> FEATURE:
<223> OTHER INFORMATION: Synthetic Probe

<400> SEQUENCE: 182
ctctgggact tgtatcagat                                              20

<210> SEQ ID NO 183
<211> LENGTH: 20
<212> TYPE: DNA
<213> ORGANISM: Artificial Sequence
<220> FEATURE:
<223> OTHER INFORMATION: Synthetic Probe

<400> SEQUENCE: 183
```
cctcttaaaa aggcctgagt                                            20

<210> SEQ ID NO 184
<211> LENGTH: 20
<212> TYPE: DNA
<213> ORGANISM: Artificial Sequence
<220> FEATURE:
<223> OTHER INFORMATION: Synthetic Probe

<400> SEQUENCE: 184
ccttgtatag agctttacgg                                            20

<210> SEQ ID NO 185
<211> LENGTH: 20
<212> TYPE: DNA
<213> ORGANISM: Artificial Sequence
<220> FEATURE:
<223> OTHER INFORMATION: Synthetic Probe

<400> SEQUENCE: 185 tcttcctttta cacagcttta                                           20

<210> SEQ ID NO 186
<211> LENGTH: 20
<212> TYPE: DNA
<213> ORGANISM: Artificial Sequence
<220> FEATURE:
<223> OTHER INFORMATION: Synthetic Probe

<400> SEQUENCE: 186
tttaaggcgc aaaagccgac                                            20

<210> SEQ ID NO 187
<211> LENGTH: 20
<212> TYPE: DNA
<213> ORGANISM: Artificial Sequence
<220> FEATURE:
<223> OTHER INFORMATION: Synthetic Probe

<400> SEQUENCE: 187 taagggtgg catgttaagt                                             20

<210> SEQ ID NO 188
<211> LENGTH: 20
<212> TYPE: DNA
<213> ORGANISM: Artificial Sequence
<220> FEATURE:
<223> OTHER INFORMATION: Synthetic Probe

<400> SEQUENCE: 188
acatcgcgtt ttaactttcc                                            20

<210> SEQ ID NO 189
<211> LENGTH: 20
<212> TYPE: DNA
<213> ORGANISM: Artificial Sequence
<220> FEATURE:
<223> OTHER INFORMATION: Synthetic Probe

<400> SEQUENCE: 189
tagaggcact ggattttcga                                            20

<210> SEQ ID NO 190
<211> LENGTH: 20
<212> TYPE: DNA
<213> ORGANISM: Artificial Sequence

```
<220> FEATURE:
<223> OTHER INFORMATION: Synthetic Probe

<400> SEQUENCE: 190
cagagtgtgg aattctgtgc                                                 20

<210> SEQ ID NO 191
<211> LENGTH: 20
<212> TYPE: DNA
<213> ORGANISM: Artificial Sequence
<220> FEATURE:
<223> OTHER INFORMATION: Synthetic Probe

<400> SEQUENCE: 191
gtgaggtttt ggcttgttaa                                                 20

<210> SEQ ID NO 192
<211> LENGTH: 20
<212> TYPE: DNA
<213> ORGANISM: Artificial Sequence
<220> FEATURE:
<223> OTHER INFORMATION: Synthetic Probe

<400> SEQUENCE: 192
gtctgcattt aggacgagta                                                 20

<210> SEQ ID NO 193
<211> LENGTH: 20
<212> TYPE: DNA
<213> ORGANISM: Artificial Sequence
<220> FEATURE:
<223> OTHER INFORMATION: Synthetic Probe

<400> SEQUENCE: 193
cgaaaatacc tgccacgttg                                                 20

<210> SEQ ID NO 194
<211> LENGTH: 20
<212> TYPE: DNA
<213> ORGANISM: Artificial Sequence
<220> FEATURE:
<223> OTHER INFORMATION: Synthetic Probe

<400> SEQUENCE: 194
ctgatagagg cagtatctgg                                                 20

<210> SEQ ID NO 195
<211> LENGTH: 20
<212> TYPE: DNA
<213> ORGANISM: Artificial Sequence
<220> FEATURE:
<223> OTHER INFORMATION: Synthetic Probe

<400> SEQUENCE: 195
ccctttaact cttaattcca                                                 20

<210> SEQ ID NO 196
<211> LENGTH: 20
<212> TYPE: DNA
<213> ORGANISM: Artificial Sequence
<220> FEATURE:
<223> OTHER INFORMATION: Synthetic Probe

<400> SEQUENCE: 196
aaatgcatcc tcagagcttt                                                 20
```

<210> SEQ ID NO 197
<211> LENGTH: 20
<212> TYPE: DNA
<213> ORGANISM: Artificial Sequence
<220> FEATURE:
<223> OTHER INFORMATION: Synthetic Probe

<400> SEQUENCE: 197 cgcactttc acgtagcaaa                                                    20

<210> SEQ ID NO 198
<211> LENGTH: 20
<212> TYPE: DNA
<213> ORGANISM: Artificial Sequence
<220> FEATURE:
<223> OTHER INFORMATION: Synthetic Probe

<400> SEQUENCE: 198
tccaaaggga gagattccat                                                   20

<210> SEQ ID NO 199
<211> LENGTH: 20
<212> TYPE: DNA
<213> ORGANISM: Artificial Sequence
<220> FEATURE:
<223> OTHER INFORMATION: Synthetic Probe

<400> SEQUENCE: 199
ctatgaagtt tctccctaga                                                   20

<210> SEQ ID NO 200
<211> LENGTH: 20
<212> TYPE: DNA
<213> ORGANISM: Artificial Sequence
<220> FEATURE:
<223> OTHER INFORMATION: Synthetic Probe

<400> SEQUENCE: 200
tgcattgtta aggcatccaa                                                   20

<210> SEQ ID NO 201
<211> LENGTH: 20
<212> TYPE: DNA
<213> ORGANISM: Artificial Sequence
<220> FEATURE:
<223> OTHER INFORMATION: Synthetic Probe

<400> SEQUENCE: 201
ctggtgcaca gttacaatgt                                                   20

<210> SEQ ID NO 202
<211> LENGTH: 20
<212> TYPE: DNA
<213> ORGANISM: Artificial Sequence
<220> FEATURE:
<223> OTHER INFORMATION: Synthetic Probe

<400> SEQUENCE: 202
agcctagtga aaaccattgc                                                   20

<210> SEQ ID NO 203
<211> LENGTH: 20
<212> TYPE: DNA
<213> ORGANISM: Artificial Sequence
<220> FEATURE:
<223> OTHER INFORMATION: Synthetic Probe

```
<400> SEQUENCE: 203
tttctgagta ccgagaagca                                               20

<210> SEQ ID NO 204
<211> LENGTH: 20
<212> TYPE: DNA
<213> ORGANISM: Artificial Sequence
<220> FEATURE:
<223> OTHER INFORMATION: Synthetic Probe

<400> SEQUENCE: 204
tgacagatgg gtagtgtctg                                               20

<210> SEQ ID NO 205
<211> LENGTH: 20
<212> TYPE: DNA
<213> ORGANISM: Artificial Sequence
<220> FEATURE:
<223> OTHER INFORMATION: Synthetic Probe

<400> SEQUENCE: 205
agttctaacc actgcacatg                                               20

<210> SEQ ID NO 206
<211> LENGTH: 20
<212> TYPE: DNA
<213> ORGANISM: Artificial Sequence
<220> FEATURE:
<223> OTHER INFORMATION: Synthetic Probe

<400> SEQUENCE: 206
aggctctttg gactttcaag                                               20

<210> SEQ ID NO 207
<211> LENGTH: 20
<212> TYPE: DNA
<213> ORGANISM: Artificial Sequence
<220> FEATURE:
<223> OTHER INFORMATION: Synthetic Probe

<400> SEQUENCE: 207
agtcatccag aagctgtatt                                               20

<210> SEQ ID NO 208
<211> LENGTH: 20
<212> TYPE: DNA
<213> ORGANISM: Artificial Sequence
<220> FEATURE:
<223> OTHER INFORMATION: Synthetic Probe

<400> SEQUENCE: 208
ttaagctgca tcctagtaca                                               20

<210> SEQ ID NO 209
<211> LENGTH: 20
<212> TYPE: DNA
<213> ORGANISM: Artificial Sequence
<220> FEATURE:
<223> OTHER INFORMATION: Synthetic Probe

<400> SEQUENCE: 209
gaactgtaca gtgtgtgtct                                               20

<210> SEQ ID NO 210
```

```
<211> LENGTH: 20
<212> TYPE: DNA
<213> ORGANISM: Artificial Sequence
<220> FEATURE:
<223> OTHER INFORMATION: Synthetic Probe

<400> SEQUENCE: 210
ctagtaccgc gttggttcta                                            20

<210> SEQ ID NO 211
<211> LENGTH: 20
<212> TYPE: DNA
<213> ORGANISM: Artificial Sequence
<220> FEATURE:
<223> OTHER INFORMATION: Synthetic Probe

<400> SEQUENCE: 211
cagagtgcaa atccccttc                                             20

<210> SEQ ID NO 212
<211> LENGTH: 20
<212> TYPE: DNA
<213> ORGANISM: Artificial Sequence
<220> FEATURE:
<223> OTHER INFORMATION: Synthetic Probe

<400> SEQUENCE: 212
taccgtacca gcatgtaact                                            20

<210> SEQ ID NO 213
<211> LENGTH: 20
<212> TYPE: DNA
<213> ORGANISM: Artificial Sequence
<220> FEATURE:
<223> OTHER INFORMATION: Synthetic Probe

<400> SEQUENCE: 213
cacaccaaga atcagtcctc                                            20

<210> SEQ ID NO 214
<211> LENGTH: 20
<212> TYPE: DNA
<213> ORGANISM: Artificial Sequence
<220> FEATURE:
<223> OTHER INFORMATION: Synthetic Probe

<400> SEQUENCE: 214
gcccattcca gaaagcttta                                            20

<210> SEQ ID NO 215
<211> LENGTH: 20
<212> TYPE: DNA
<213> ORGANISM: Artificial Sequence
<220> FEATURE:
<223> OTHER INFORMATION: Synthetic Probe

<400> SEQUENCE: 215
cctcccatat cctcccttaa                                            20

<210> SEQ ID NO 216
<211> LENGTH: 20
<212> TYPE: DNA
<213> ORGANISM: Artificial Sequence
<220> FEATURE:
<223> OTHER INFORMATION: Synthetic Probe

<400> SEQUENCE: 216
```

```
tctaaattca agaaccgccc                                              20

<210> SEQ ID NO 217
<211> LENGTH: 20
<212> TYPE: DNA
<213> ORGANISM: Artificial Sequence
<220> FEATURE:
<223> OTHER INFORMATION: Synthetic Probe

<400> SEQUENCE: 217
atctcctttc agatccggtc                                              20

<210> SEQ ID NO 218
<211> LENGTH: 20
<212> TYPE: DNA
<213> ORGANISM: Artificial Sequence
<220> FEATURE:
<223> OTHER INFORMATION: Synthetic Probe

<400> SEQUENCE: 218
ggctccagaa acagatttca                                              20

<210> SEQ ID NO 219
<211> LENGTH: 20
<212> TYPE: DNA
<213> ORGANISM: Artificial Sequence
<220> FEATURE:
<223> OTHER INFORMATION: Synthetic Probe

<400> SEQUENCE: 219
taaatcccag actcaggact                                              20

<210> SEQ ID NO 220
<211> LENGTH: 20
<212> TYPE: DNA
<213> ORGANISM: Artificial Sequence
<220> FEATURE:
<223> OTHER INFORMATION: Synthetic Probe

<400> SEQUENCE: 220
aagggccaag tcaagttaag                                              20

<210> SEQ ID NO 221
<211> LENGTH: 20
<212> TYPE: DNA
<213> ORGANISM: Artificial Sequence
<220> FEATURE:
<223> OTHER INFORMATION: Synthetic Probe

<400> SEQUENCE: 221
ataactgcat tgcccattga                                              20

<210> SEQ ID NO 222
<211> LENGTH: 20
<212> TYPE: DNA
<213> ORGANISM: Artificial Sequence
<220> FEATURE:
<223> OTHER INFORMATION: Synthetic Probe

<400> SEQUENCE: 222
tgactcttat gagggagctc                                              20

<210> SEQ ID NO 223
<211> LENGTH: 20
<212> TYPE: DNA
```

```
<213> ORGANISM: Artificial Sequence
<220> FEATURE:
<223> OTHER INFORMATION: Synthetic Probe

<400> SEQUENCE: 223
agtgaatttg gcccaagaag                                              20

<210> SEQ ID NO 224
<211> LENGTH: 20
<212> TYPE: DNA
<213> ORGANISM: Artificial Sequence
<220> FEATURE:
<223> OTHER INFORMATION: Synthetic Probe

<400> SEQUENCE: 224
cagagatagt ctgggaggag                                              20

<210> SEQ ID NO 225
<211> LENGTH: 20
<212> TYPE: DNA
<213> ORGANISM: Artificial Sequence
<220> FEATURE:
<223> OTHER INFORMATION: Synthetic Probe

<400> SEQUENCE: 225
gctaagtgtt gcctctactg                                              20

<210> SEQ ID NO 226
<211> LENGTH: 20
<212> TYPE: DNA
<213> ORGANISM: Artificial Sequence
<220> FEATURE:
<223> OTHER INFORMATION: Synthetic Probe

<400> SEQUENCE: 226
gaatccacgg tccattttgg                                              20

<210> SEQ ID NO 227
<211> LENGTH: 20
<212> TYPE: DNA
<213> ORGANISM: Artificial Sequence
<220> FEATURE:
<223> OTHER INFORMATION: Synthetic Probe

<400> SEQUENCE: 227
cttgctgtat ttggggatca                                              20

<210> SEQ ID NO 228
<211> LENGTH: 20
<212> TYPE: DNA
<213> ORGANISM: Artificial Sequence
<220> FEATURE:
<223> OTHER INFORMATION: Synthetic Probe

<400> SEQUENCE: 228
catcgagatg cacagctttg                                              20

<210> SEQ ID NO 229
<211> LENGTH: 20
<212> TYPE: DNA
<213> ORGANISM: Artificial Sequence
<220> FEATURE:
<223> OTHER INFORMATION: Synthetic Probe

<400> SEQUENCE: 229
gtgacatccg tctctggagg                                              20
```

```
<210> SEQ ID NO 230
<211> LENGTH: 20
<212> TYPE: DNA
<213> ORGANISM: Artificial Sequence
<220> FEATURE:
<223> OTHER INFORMATION: Synthetic Probe

<400> SEQUENCE: 230
aaggagcaag aaccacacag                                              20

<210> SEQ ID NO 231
<211> LENGTH: 20
<212> TYPE: DNA
<213> ORGANISM: Artificial Sequence
<220> FEATURE:
<223> OTHER INFORMATION: Synthetic Probe

<400> SEQUENCE: 231
aatgcacggt taaagttcct                                              20

<210> SEQ ID NO 232
<211> LENGTH: 20
<212> TYPE: DNA
<213> ORGANISM: Artificial Sequence
<220> FEATURE:
<223> OTHER INFORMATION: Synthetic Probe

<400> SEQUENCE: 232
caggcacaga tttacaggaa                                              20

<210> SEQ ID NO 233
<211> LENGTH: 20
<212> TYPE: DNA
<213> ORGANISM: Artificial Sequence
<220> FEATURE:
<223> OTHER INFORMATION: Synthetic Probe

<400> SEQUENCE: 233
agccagttct cattagcaag                                              20

<210> SEQ ID NO 234
<211> LENGTH: 20
<212> TYPE: DNA
<213> ORGANISM: Artificial Sequence
<220> FEATURE:
<223> OTHER INFORMATION: Synthetic Probe

<400> SEQUENCE: 234
acacactaaa gaacacaccc                                              20

<210> SEQ ID NO 235
<211> LENGTH: 20
<212> TYPE: DNA
<213> ORGANISM: Artificial Sequence
<220> FEATURE:
<223> OTHER INFORMATION: Synthetic Probe

<400> SEQUENCE: 235
gatccttgtg cacggaagtt                                              20

<210> SEQ ID NO 236
<211> LENGTH: 20
<212> TYPE: DNA
<213> ORGANISM: Artificial Sequence
<220> FEATURE:
```

<223> OTHER INFORMATION: Synthetic Probe

<400> SEQUENCE: 236
aatgaactga tggcgttcat                                         20

<210> SEQ ID NO 237
<211> LENGTH: 20
<212> TYPE: DNA
<213> ORGANISM: Artificial Sequence
<220> FEATURE:
<223> OTHER INFORMATION: Synthetic Probe

<400> SEQUENCE: 237
cacacctcac ttgaacaagt                                         20

<210> SEQ ID NO 238
<211> LENGTH: 20
<212> TYPE: DNA
<213> ORGANISM: Artificial Sequence
<220> FEATURE:
<223> OTHER INFORMATION: Synthetic Probe

<400> SEQUENCE: 238
gtgagggttc ctctgactca                                         20

<210> SEQ ID NO 239
<211> LENGTH: 20
<212> TYPE: DNA
<213> ORGANISM: Artificial Sequence
<220> FEATURE:
<223> OTHER INFORMATION: Synthetic Probe

<400> SEQUENCE: 239
tttcacaaat ccagctggaa                                         20

<210> SEQ ID NO 240
<211> LENGTH: 20
<212> TYPE: DNA
<213> ORGANISM: Artificial Sequence
<220> FEATURE:
<223> OTHER INFORMATION: Synthetic Probe

<400> SEQUENCE: 240
cccaaagacc caaatcagaa                                         20

<210> SEQ ID NO 241
<211> LENGTH: 20
<212> TYPE: DNA
<213> ORGANISM: Artificial Sequence
<220> FEATURE:
<223> OTHER INFORMATION: Synthetic Probe

<400> SEQUENCE: 241
ggggttgaac caaatatcca                                         20

<210> SEQ ID NO 242
<211> LENGTH: 20
<212> TYPE: DNA
<213> ORGANISM: Artificial Sequence
<220> FEATURE:
<223> OTHER INFORMATION: Synthetic Probe

<400> SEQUENCE: 242
aactgcctaa accttctgtg                                         20

```
<210> SEQ ID NO 243
<211> LENGTH: 20
<212> TYPE: DNA
<213> ORGANISM: Artificial Sequence
<220> FEATURE:
<223> OTHER INFORMATION: Synthetic Probe

<400> SEQUENCE: 243
gtccccacaa gtaagcatac                                               20

<210> SEQ ID NO 244
<211> LENGTH: 20
<212> TYPE: DNA
<213> ORGANISM: Artificial Sequence
<220> FEATURE:
<223> OTHER INFORMATION: Synthetic Probe

<400> SEQUENCE: 244
atcaggtgca cacattaagg                                               20

<210> SEQ ID NO 245
<211> LENGTH: 20
<212> TYPE: DNA
<213> ORGANISM: Artificial Sequence
<220> FEATURE:
<223> OTHER INFORMATION: Synthetic Probe

<400> SEQUENCE: 245
gaatgtcagc agctctcatg                                               20

<210> SEQ ID NO 246
<211> LENGTH: 20
<212> TYPE: DNA
<213> ORGANISM: Artificial Sequence
<220> FEATURE:
<223> OTHER INFORMATION: Synthetic Probe

<400> SEQUENCE: 246
gatggactag aaacatgggc                                               20

<210> SEQ ID NO 247
<211> LENGTH: 20
<212> TYPE: DNA
<213> ORGANISM: Artificial Sequence
<220> FEATURE:
<223> OTHER INFORMATION: Synthetic Probe

<400> SEQUENCE: 247
ccacccatga agacaatgat                                               20

<210> SEQ ID NO 248
<211> LENGTH: 20
<212> TYPE: DNA
<213> ORGANISM: Artificial Sequence
<220> FEATURE:
<223> OTHER INFORMATION: Synthetic Probe

<400> SEQUENCE: 248
cagaagcaga acccaagatg                                               20

<210> SEQ ID NO 249
<211> LENGTH: 20
<212> TYPE: DNA
<213> ORGANISM: Artificial Sequence
<220> FEATURE:
<223> OTHER INFORMATION: Synthetic Probe
```

<400> SEQUENCE: 249
gctcagctat caagtaacgg                                               20

<210> SEQ ID NO 250
<211> LENGTH: 20
<212> TYPE: DNA
<213> ORGANISM: Artificial Sequence
<220> FEATURE:
<223> OTHER INFORMATION: Synthetic Probe

<400> SEQUENCE: 250
gtattccgtg gatcagcaaa                                               20

<210> SEQ ID NO 251
<211> LENGTH: 20
<212> TYPE: DNA
<213> ORGANISM: Artificial Sequence
<220> FEATURE:
<223> OTHER INFORMATION: Synthetic Probe

<400> SEQUENCE: 251
gtccccaacc acatagaaag                                               20

<210> SEQ ID NO 252
<211> LENGTH: 20
<212> TYPE: DNA
<213> ORGANISM: Artificial Sequence
<220> FEATURE:
<223> OTHER INFORMATION: Synthetic Probe

<400> SEQUENCE: 252
tccttacttc cctaggacaa                                               20

<210> SEQ ID NO 253
<211> LENGTH: 20
<212> TYPE: DNA
<213> ORGANISM: Artificial Sequence
<220> FEATURE:
<223> OTHER INFORMATION: Synthetic Probe

<400> SEQUENCE: 253
cccatctaaa agcgggaaag                                               20

<210> SEQ ID NO 254
<211> LENGTH: 20
<212> TYPE: DNA
<213> ORGANISM: Artificial Sequence
<220> FEATURE:
<223> OTHER INFORMATION: Synthetic Probe

<400> SEQUENCE: 254
gagtacagga gagagtccag                                               20

<210> SEQ ID NO 255
<211> LENGTH: 20
<212> TYPE: DNA
<213> ORGANISM: Artificial Sequence
<220> FEATURE:
<223> OTHER INFORMATION: Synthetic Probe

<400> SEQUENCE: 255
cagaacgact aagaagcacg                                               20

<210> SEQ ID NO 256
<211> LENGTH: 20

```
<212> TYPE: DNA
<213> ORGANISM: Artificial Sequence
<220> FEATURE:
<223> OTHER INFORMATION: Synthetic Probe

<400> SEQUENCE: 256
gattctctcg cttctaggcc                                               20

<210> SEQ ID NO 257
<211> LENGTH: 20
<212> TYPE: DNA
<213> ORGANISM: Artificial Sequence
<220> FEATURE:
<223> OTHER INFORMATION: Synthetic Probe

<400> SEQUENCE: 257
cgaagagact gagtggtacc                                               20

<210> SEQ ID NO 258
<211> LENGTH: 20
<212> TYPE: DNA
<213> ORGANISM: Artificial Sequence
<220> FEATURE:
<223> OTHER INFORMATION: Synthetic Probe

<400> SEQUENCE: 258
aaggaaacct taaggcaatt                                               20

<210> SEQ ID NO 259
<211> LENGTH: 20
<212> TYPE: DNA
<213> ORGANISM: Artificial Sequence
<220> FEATURE:
<223> OTHER INFORMATION: Synthetic Probe

<400> SEQUENCE: 259
atgtccacct gaacactctg                                               20

<210> SEQ ID NO 260
<211> LENGTH: 20
<212> TYPE: DNA
<213> ORGANISM: Artificial Sequence
<220> FEATURE:
<223> OTHER INFORMATION: Synthetic Probe

<400> SEQUENCE: 260
tcctgaatgt ctctgctact                                               20

<210> SEQ ID NO 261
<211> LENGTH: 20
<212> TYPE: DNA
<213> ORGANISM: Artificial Sequence
<220> FEATURE:
<223> OTHER INFORMATION: Synthetic Probe

<400> SEQUENCE: 261
tcagtcactg cagcttgtac                                               20

<210> SEQ ID NO 262
<211> LENGTH: 20
<212> TYPE: DNA
<213> ORGANISM: Artificial Sequence
<220> FEATURE:
<223> OTHER INFORMATION: Synthetic Probe

<400> SEQUENCE: 262
```
taggatgcct cctcaacctc                                                   20

<210> SEQ ID NO 263
<211> LENGTH: 20
<212> TYPE: DNA
<213> ORGANISM: Artificial Sequence
<220> FEATURE:
<223> OTHER INFORMATION: Synthetic Probe

<400> SEQUENCE: 263
aagctctaaa ctccactgga                                                   20

<210> SEQ ID NO 264
<211> LENGTH: 20
<212> TYPE: DNA
<213> ORGANISM: Artificial Sequence
<220> FEATURE:
<223> OTHER INFORMATION: Synthetic Probe

<400> SEQUENCE: 264
ttcttatccc agacctctcg                                                   20

<210> SEQ ID NO 265
<211> LENGTH: 20
<212> TYPE: DNA
<213> ORGANISM: Artificial Sequence
<220> FEATURE:
<223> OTHER INFORMATION: Synthetic Probe

<400> SEQUENCE: 265
gctctatcca ggtagtgaat                                                   20

<210> SEQ ID NO 266
<211> LENGTH: 20
<212> TYPE: DNA
<213> ORGANISM: Artificial Sequence
<220> FEATURE:
<223> OTHER INFORMATION: Synthetic Probe

<400> SEQUENCE: 266
cagccacctt atggagcaag                                                   20

<210> SEQ ID NO 267
<211> LENGTH: 20
<212> TYPE: DNA
<213> ORGANISM: Artificial Sequence
<220> FEATURE:
<223> OTHER INFORMATION: Synthetic Probe

<400> SEQUENCE: 267
agacagagag ctagacactt                                                   20

<210> SEQ ID NO 268
<211> LENGTH: 20
<212> TYPE: DNA
<213> ORGANISM: Artificial Sequence
<220> FEATURE:
<223> OTHER INFORMATION: Synthetic Probe

<400> SEQUENCE: 268
ctagttgctg caatgggagt                                                   20

<210> SEQ ID NO 269
<211> LENGTH: 20
<212> TYPE: DNA
<213> ORGANISM: Artificial Sequence
<220> FEATURE:
<223> OTHER INFORMATION: Synthetic Probe

<400> SEQUENCE: 269
gctgcattgt tcaggatact          20

<210> SEQ ID NO 270
<211> LENGTH: 20
<212> TYPE: DNA
<213> ORGANISM: Artificial Sequence
<220> FEATURE:
<223> OTHER INFORMATION: Synthetic Probe

<400> SEQUENCE: 270
ctagtcttgc acaccaagag          20

<210> SEQ ID NO 271
<211> LENGTH: 20
<212> TYPE: DNA
<213> ORGANISM: Artificial Sequence
<220> FEATURE:
<223> OTHER INFORMATION: Synthetic Probe

<400> SEQUENCE: 271
gacctgctgg aatcagaatc          20

<210> SEQ ID NO 272
<211> LENGTH: 20
<212> TYPE: DNA
<213> ORGANISM: Artificial Sequence
<220> FEATURE:
<223> OTHER INFORMATION: Synthetic Probe

<400> SEQUENCE: 272
cctattagac ggcctcaatg          20

<210> SEQ ID NO 273
<211> LENGTH: 20
<212> TYPE: DNA
<213> ORGANISM: Artificial Sequence
<220> FEATURE:
<223> OTHER INFORMATION: Synthetic Probe

<400> SEQUENCE: 273
ctcctgccca atatccaaaa          20

<210> SEQ ID NO 274
<211> LENGTH: 20
<212> TYPE: DNA
<213> ORGANISM: Artificial Sequence
<220> FEATURE:
<223> OTHER INFORMATION: Synthetic Probe

<400> SEQUENCE: 274
cagatgcctg aatccaaact          20

<210> SEQ ID NO 275
<211> LENGTH: 20
<212> TYPE: DNA
<213> ORGANISM: Artificial Sequence
<220> FEATURE:
<223> OTHER INFORMATION: Synthetic Probe

<400> SEQUENCE: 275
caagcctgat tcccaaaaca          20

```
<210> SEQ ID NO 276
<211> LENGTH: 20
<212> TYPE: DNA
<213> ORGANISM: Artificial Sequence
<220> FEATURE:
<223> OTHER INFORMATION: Synthetic Probe

<400> SEQUENCE: 276
ggtggaaatc ttaatcccca                                               20

<210> SEQ ID NO 277
<211> LENGTH: 20
<212> TYPE: DNA
<213> ORGANISM: Artificial Sequence
<220> FEATURE:
<223> OTHER INFORMATION: Synthetic Probe

<400> SEQUENCE: 277
cgagcttgtt aagtctcgtc                                               20

<210> SEQ ID NO 278
<211> LENGTH: 20
<212> TYPE: DNA
<213> ORGANISM: Artificial Sequence
<220> FEATURE:
<223> OTHER INFORMATION: Synthetic Probe

<400> SEQUENCE: 278
gagtggtttc agcagaatct                                               20

<210> SEQ ID NO 279
<211> LENGTH: 20
<212> TYPE: DNA
<213> ORGANISM: Artificial Sequence
<220> FEATURE:
<223> OTHER INFORMATION: Synthetic Probe

<400> SEQUENCE: 279
accaccgaga aggattctaa                                               20

<210> SEQ ID NO 280
<211> LENGTH: 20
<212> TYPE: DNA
<213> ORGANISM: Artificial Sequence
<220> FEATURE:
<223> OTHER INFORMATION: Synthetic Probe

<400> SEQUENCE: 280
ttctcacaca gatgagtgcg                                               20

<210> SEQ ID NO 281
<211> LENGTH: 20
<212> TYPE: DNA
<213> ORGANISM: Artificial Sequence
<220> FEATURE:
<223> OTHER INFORMATION: Synthetic Probe

<400> SEQUENCE: 281
taggaaaaca gaccctttgg                                               20

<210> SEQ ID NO 282
<211> LENGTH: 20
<212> TYPE: DNA
<213> ORGANISM: Artificial Sequence
<220> FEATURE:
<223> OTHER INFORMATION: Synthetic Probe
```

```
<400> SEQUENCE: 282
tcaagagatc cccaaacacg                                              20

<210> SEQ ID NO 283
<211> LENGTH: 20
<212> TYPE: DNA
<213> ORGANISM: Artificial Sequence
<220> FEATURE:
<223> OTHER INFORMATION: Synthetic Probe

<400> SEQUENCE: 283
atcacagacc agaatgcctg                                              20

<210> SEQ ID NO 284
<211> LENGTH: 20
<212> TYPE: DNA
<213> ORGANISM: Artificial Sequence
<220> FEATURE:
<223> OTHER INFORMATION: Synthetic Probe

<400> SEQUENCE: 284
cattctacca cacatggagg                                              20

<210> SEQ ID NO 285
<211> LENGTH: 20
<212> TYPE: DNA
<213> ORGANISM: Artificial Sequence
<220> FEATURE:
<223> OTHER INFORMATION: Synthetic Probe

<400> SEQUENCE: 285
gagctaacac ctgacaactt                                              20

<210> SEQ ID NO 286
<211> LENGTH: 20
<212> TYPE: DNA
<213> ORGANISM: Artificial Sequence
<220> FEATURE:
<223> OTHER INFORMATION: Synthetic Probe

<400> SEQUENCE: 286
ctcactcagg ctaaaatcct                                              20

<210> SEQ ID NO 287
<211> LENGTH: 20
<212> TYPE: DNA
<213> ORGANISM: Artificial Sequence
<220> FEATURE:
<223> OTHER INFORMATION: Synthetic Probe

<400> SEQUENCE: 287
gaccttgaag aagccagaaa                                              20

<210> SEQ ID NO 288
<211> LENGTH: 20
<212> TYPE: DNA
<213> ORGANISM: Artificial Sequence
<220> FEATURE:
<223> OTHER INFORMATION: Synthetic Probe

<400> SEQUENCE: 288
cctgaagctg agaagttgat                                              20

<210> SEQ ID NO 289
```

```
<211> LENGTH: 20
<212> TYPE: DNA
<213> ORGANISM: Artificial Sequence
<220> FEATURE:
<223> OTHER INFORMATION: Synthetic Probe

<400> SEQUENCE: 289
caagggaaaa gggcttgaaa                                                   20

<210> SEQ ID NO 290
<211> LENGTH: 20
<212> TYPE: DNA
<213> ORGANISM: Artificial Sequence
<220> FEATURE:
<223> OTHER INFORMATION: Synthetic Probe

<400> SEQUENCE: 290
gagaaagctt ccagcagatt                                                   20

<210> SEQ ID NO 291
<211> LENGTH: 20
<212> TYPE: DNA
<213> ORGANISM: Artificial Sequence
<220> FEATURE:
<223> OTHER INFORMATION: Synthetic Probe

<400> SEQUENCE: 291
aggtcaaggg gtctagaaat                                                   20

<210> SEQ ID NO 292
<211> LENGTH: 20
<212> TYPE: DNA
<213> ORGANISM: Artificial Sequence
<220> FEATURE:
<223> OTHER INFORMATION: Synthetic Probe

<400> SEQUENCE: 292
agatgaataa aggctgagcc                                                   20

<210> SEQ ID NO 293
<211> LENGTH: 20
<212> TYPE: DNA
<213> ORGANISM: Artificial Sequence
<220> FEATURE:
<223> OTHER INFORMATION: Synthetic Probe

<400> SEQUENCE: 293
ctggaagtat ggggtaggaa                                                   20

<210> SEQ ID NO 294
<211> LENGTH: 20
<212> TYPE: DNA
<213> ORGANISM: Artificial Sequence
<220> FEATURE:
<223> OTHER INFORMATION: Synthetic Probe

<400> SEQUENCE: 294
tcctaggaat cagagaaggg                                                   20

<210> SEQ ID NO 295
<211> LENGTH: 20
<212> TYPE: DNA
<213> ORGANISM: Artificial Sequence
<220> FEATURE:
<223> OTHER INFORMATION: Synthetic Probe

<400> SEQUENCE: 295
```
ggaatggtgg aaagtgacaa                                                    20

<210> SEQ ID NO 296
<211> LENGTH: 20
<212> TYPE: DNA
<213> ORGANISM: Artificial Sequence
<220> FEATURE:
<223> OTHER INFORMATION: Synthetic Probe

<400> SEQUENCE: 296
tgatcagaga cacaggagat                                                    20

<210> SEQ ID NO 297
<211> LENGTH: 20
<212> TYPE: DNA
<213> ORGANISM: Artificial Sequence
<220> FEATURE:
<223> OTHER INFORMATION: Synthetic Probe

<400> SEQUENCE: 297
gcaggtcttt ggaagtgatc                                                    20

<210> SEQ ID NO 298
<211> LENGTH: 20
<212> TYPE: DNA
<213> ORGANISM: Artificial Sequence
<220> FEATURE:
<223> OTHER INFORMATION: Synthetic Probe

<400> SEQUENCE: 298
tggggagaag tctaggattg                                                    20

<210> SEQ ID NO 299
<211> LENGTH: 20
<212> TYPE: DNA
<213> ORGANISM: Artificial Sequence
<220> FEATURE:
<223> OTHER INFORMATION: Synthetic Probe

<400> SEQUENCE: 299
gatctgcaag atgaggaagg                                                    20

<210> SEQ ID NO 300
<211> LENGTH: 20
<212> TYPE: DNA
<213> ORGANISM: Artificial Sequence
<220> FEATURE:
<223> OTHER INFORMATION: Synthetic Probe

<400> SEQUENCE: 300
actccaaatt ggagttctgg                                                    20

<210> SEQ ID NO 301
<211> LENGTH: 20
<212> TYPE: DNA
<213> ORGANISM: Artificial Sequence
<220> FEATURE:
<223> OTHER INFORMATION: Synthetic Probe

<400> SEQUENCE: 301
attgtagtga ccaaggaaca                                                    20

<210> SEQ ID NO 302
<211> LENGTH: 20
<212> TYPE: DNA

```
<213> ORGANISM: Artificial Sequence
<220> FEATURE:
<223> OTHER INFORMATION: Synthetic Probe

<400> SEQUENCE: 302
ctgaatcgag taagccttgg                                              20

<210> SEQ ID NO 303
<211> LENGTH: 20
<212> TYPE: DNA
<213> ORGANISM: Artificial Sequence
<220> FEATURE:
<223> OTHER INFORMATION: Synthetic Probe

<400> SEQUENCE: 303
caaccgggga gataagagac                                              20

<210> SEQ ID NO 304
<211> LENGTH: 20
<212> TYPE: DNA
<213> ORGANISM: Artificial Sequence
<220> FEATURE:
<223> OTHER INFORMATION: Synthetic Probe

<400> SEQUENCE: 304
cctacttgga gcaagtcatg                                              20

<210> SEQ ID NO 305
<211> LENGTH: 20
<212> TYPE: DNA
<213> ORGANISM: Artificial Sequence
<220> FEATURE:
<223> OTHER INFORMATION: Synthetic Probe

<400> SEQUENCE: 305
aattaggatg gcaggccttc                                              20

<210> SEQ ID NO 306
<211> LENGTH: 20
<212> TYPE: DNA
<213> ORGANISM: Artificial Sequence
<220> FEATURE:
<223> OTHER INFORMATION: Synthetic Probe

<400> SEQUENCE: 306
aaaatgagag gcggaggaag                                              20

<210> SEQ ID NO 307
<211> LENGTH: 20
<212> TYPE: DNA
<213> ORGANISM: Artificial Sequence
<220> FEATURE:
<223> OTHER INFORMATION: Synthetic Probe

<400> SEQUENCE: 307
cgtcctctta ggacacctaa                                              20

<210> SEQ ID NO 308
<211> LENGTH: 20
<212> TYPE: DNA
<213> ORGANISM: Artificial Sequence
<220> FEATURE:
<223> OTHER INFORMATION: Synthetic Probe

<400> SEQUENCE: 308
gctcctaaac ttggctagtc                                              20
```

```
<210> SEQ ID NO 309
<211> LENGTH: 20
<212> TYPE: DNA
<213> ORGANISM: Artificial Sequence
<220> FEATURE:
<223> OTHER INFORMATION: Synthetic Probe

<400> SEQUENCE: 309
tatcctggtc aatgggagga                                            20

<210> SEQ ID NO 310
<211> LENGTH: 20
<212> TYPE: DNA
<213> ORGANISM: Artificial Sequence
<220> FEATURE:
<223> OTHER INFORMATION: Synthetic Probe

<400> SEQUENCE: 310
gcttagcaaa tccctcaacc                                            20

<210> SEQ ID NO 311
<211> LENGTH: 20
<212> TYPE: DNA
<213> ORGANISM: Artificial Sequence
<220> FEATURE:
<223> OTHER INFORMATION: Synthetic Probe

<400> SEQUENCE: 311
catcccataa ccaggaatgt                                            20

<210> SEQ ID NO 312
<211> LENGTH: 20
<212> TYPE: DNA
<213> ORGANISM: Artificial Sequence
<220> FEATURE:
<223> OTHER INFORMATION: Synthetic Probe

<400> SEQUENCE: 312
cctctttaat caccactccc                                            20

<210> SEQ ID NO 313
<211> LENGTH: 20
<212> TYPE: DNA
<213> ORGANISM: Artificial Sequence
<220> FEATURE:
<223> OTHER INFORMATION: Synthetic Probe

<400> SEQUENCE: 313
aacagaccta aagggaggat                                            20

<210> SEQ ID NO 314
<211> LENGTH: 20
<212> TYPE: DNA
<213> ORGANISM: Artificial Sequence
<220> FEATURE:
<223> OTHER INFORMATION: Synthetic Probe

<400> SEQUENCE: 314
gtttggcagg ttacccagtg                                            20

<210> SEQ ID NO 315
<211> LENGTH: 20
<212> TYPE: DNA
<213> ORGANISM: Artificial Sequence
<220> FEATURE:
```

<223> OTHER INFORMATION: Synthetic Probe

<400> SEQUENCE: 315
tataccagga acctaggagg                                        20

<210> SEQ ID NO 316
<211> LENGTH: 20
<212> TYPE: DNA
<213> ORGANISM: Artificial Sequence
<220> FEATURE:
<223> OTHER INFORMATION: Synthetic Probe

<400> SEQUENCE: 316
tccccagcat catatctcat                                        20

<210> SEQ ID NO 317
<211> LENGTH: 20
<212> TYPE: DNA
<213> ORGANISM: Artificial Sequence
<220> FEATURE:
<223> OTHER INFORMATION: Synthetic Probe

<400> SEQUENCE: 317
tatagcaact ggtgtctcca                                        20

<210> SEQ ID NO 318
<211> LENGTH: 20
<212> TYPE: DNA
<213> ORGANISM: Artificial Sequence
<220> FEATURE:
<223> OTHER INFORMATION: Synthetic Probe

<400> SEQUENCE: 318
cctgtttcac atctggatcc                                        20

<210> SEQ ID NO 319
<211> LENGTH: 20
<212> TYPE: DNA
<213> ORGANISM: Artificial Sequence
<220> FEATURE:
<223> OTHER INFORMATION: Synthetic Probe

<400> SEQUENCE: 319
gaatgcgaaa catctccagc                                        20

<210> SEQ ID NO 320
<211> LENGTH: 20
<212> TYPE: DNA
<213> ORGANISM: Artificial Sequence
<220> FEATURE:
<223> OTHER INFORMATION: Synthetic Probe

<400> SEQUENCE: 320
aaacttctca ggaaaacgga                                        20

<210> SEQ ID NO 321
<211> LENGTH: 20
<212> TYPE: DNA
<213> ORGANISM: Artificial Sequence
<220> FEATURE:
<223> OTHER INFORMATION: Synthetic Probe

<400> SEQUENCE: 321
ctcttctgac accacagact                                        20

```
<210> SEQ ID NO 322
<211> LENGTH: 20
<212> TYPE: DNA
<213> ORGANISM: Artificial Sequence
<220> FEATURE:
<223> OTHER INFORMATION: Synthetic Probe

<400> SEQUENCE: 322
gaacacagcc tcagttactg                                            20

<210> SEQ ID NO 323
<211> LENGTH: 20
<212> TYPE: DNA
<213> ORGANISM: Artificial Sequence
<220> FEATURE:
<223> OTHER INFORMATION: Synthetic Probe

<400> SEQUENCE: 323
ctgaaactgg caaactcaca                                            20

<210> SEQ ID NO 324
<211> LENGTH: 20
<212> TYPE: DNA
<213> ORGANISM: Artificial Sequence
<220> FEATURE:
<223> OTHER INFORMATION: Synthetic Probe

<400> SEQUENCE: 324
gtgctttcca gtaagttgga                                            20

<210> SEQ ID NO 325
<211> LENGTH: 20
<212> TYPE: DNA
<213> ORGANISM: Artificial Sequence
<220> FEATURE:
<223> OTHER INFORMATION: Synthetic Probe

<400> SEQUENCE: 325
cacgttccaa gacaaagaca                                            20

<210> SEQ ID NO 326
<211> LENGTH: 20
<212> TYPE: DNA
<213> ORGANISM: Artificial Sequence
<220> FEATURE:
<223> OTHER INFORMATION: Synthetic Probe

<400> SEQUENCE: 326
ccacttgact gcaacttgaa                                            20

<210> SEQ ID NO 327
<211> LENGTH: 20
<212> TYPE: DNA
<213> ORGANISM: Artificial Sequence
<220> FEATURE:
<223> OTHER INFORMATION: Synthetic Probe

<400> SEQUENCE: 327
cgctagagaa agctcagaag                                            20

<210> SEQ ID NO 328
<211> LENGTH: 20
<212> TYPE: DNA
<213> ORGANISM: Artificial Sequence
<220> FEATURE:
<223> OTHER INFORMATION: Synthetic Probe
```

```
<400> SEQUENCE: 328
cggagaagca aagtgagaag                                                 20

<210> SEQ ID NO 329
<211> LENGTH: 20
<212> TYPE: DNA
<213> ORGANISM: Artificial Sequence
<220> FEATURE:
<223> OTHER INFORMATION: Synthetic Probe

<400> SEQUENCE: 329
aactccagat tccagaccaa                                                 20

<210> SEQ ID NO 330
<211> LENGTH: 20
<212> TYPE: DNA
<213> ORGANISM: Artificial Sequence
<220> FEATURE:
<223> OTHER INFORMATION: Synthetic Probe

<400> SEQUENCE: 330
tgacagcaag aaccgaagag                                                 20

<210> SEQ ID NO 331
<211> LENGTH: 20
<212> TYPE: DNA
<213> ORGANISM: Artificial Sequence
<220> FEATURE:
<223> OTHER INFORMATION: Synthetic Probe

<400> SEQUENCE: 331
taggctggat tctatccagg                                                 20

<210> SEQ ID NO 332
<211> LENGTH: 20
<212> TYPE: DNA
<213> ORGANISM: Artificial Sequence
<220> FEATURE:
<223> OTHER INFORMATION: Synthetic Probe

<400> SEQUENCE: 332
tcaaccagta aatgcccatc                                                 20

<210> SEQ ID NO 333
<211> LENGTH: 20
<212> TYPE: DNA
<213> ORGANISM: Artificial Sequence
<220> FEATURE:
<223> OTHER INFORMATION: Synthetic Probe

<400> SEQUENCE: 333
ccctttcctc acatgctgag                                                 20

<210> SEQ ID NO 334
<211> LENGTH: 20
<212> TYPE: DNA
<213> ORGANISM: Artificial Sequence
<220> FEATURE:
<223> OTHER INFORMATION: Synthetic Probe

<400> SEQUENCE: 334
gttgggtgca acaagagaag                                                 20

<210> SEQ ID NO 335
<211> LENGTH: 20
```

```
<212> TYPE: DNA
<213> ORGANISM: Artificial Sequence
<220> FEATURE:
<223> OTHER INFORMATION: Synthetic Probe

<400> SEQUENCE: 335
ctatgctgcg cgacttattc                                                    20

<210> SEQ ID NO 336
<211> LENGTH: 20
<212> TYPE: DNA
<213> ORGANISM: Artificial Sequence
<220> FEATURE:
<223> OTHER INFORMATION: Synthetic Probe

<400> SEQUENCE: 336
tttcatctgc ttctcacagc                                                    20

<210> SEQ ID NO 337
<211> LENGTH: 20
<212> TYPE: DNA
<213> ORGANISM: Artificial Sequence
<220> FEATURE:
<223> OTHER INFORMATION: Synthetic Probe

<400> SEQUENCE: 337
tatgtaccac agcgttaagc                                                    20

<210> SEQ ID NO 338
<211> LENGTH: 20
<212> TYPE: DNA
<213> ORGANISM: Artificial Sequence
<220> FEATURE:
<223> OTHER INFORMATION: Synthetic Probe

<400> SEQUENCE: 338
ccatagagcc gtttgattct                                                    20

<210> SEQ ID NO 339
<211> LENGTH: 20
<212> TYPE: DNA
<213> ORGANISM: Artificial Sequence
<220> FEATURE:
<223> OTHER INFORMATION: Synthetic Probe

<400> SEQUENCE: 339
agtccaggtt ctcctatctc                                                    20

<210> SEQ ID NO 340
<211> LENGTH: 20
<212> TYPE: DNA
<213> ORGANISM: Artificial Sequence
<220> FEATURE:
<223> OTHER INFORMATION: Synthetic Probe

<400> SEQUENCE: 340
agctggagat ctggacataa                                                    20

<210> SEQ ID NO 341
<211> LENGTH: 20
<212> TYPE: DNA
<213> ORGANISM: Artificial Sequence
<220> FEATURE:
<223> OTHER INFORMATION: Synthetic Probe

<400> SEQUENCE: 341
```
cctttgacag caaggaaacc                                              20

<210> SEQ ID NO 342
<211> LENGTH: 20
<212> TYPE: DNA
<213> ORGANISM: Artificial Sequence
<220> FEATURE:
<223> OTHER INFORMATION: Synthetic Probe

<400> SEQUENCE: 342
gttcaggaag ggaacaatgg                                              20

<210> SEQ ID NO 343
<211> LENGTH: 20
<212> TYPE: DNA
<213> ORGANISM: Artificial Sequence
<220> FEATURE:
<223> OTHER INFORMATION: Synthetic Probe

<400> SEQUENCE: 343
ttttactgtg aacctgaccc                                              20

<210> SEQ ID NO 344
<211> LENGTH: 20
<212> TYPE: DNA
<213> ORGANISM: Artificial Sequence
<220> FEATURE:
<223> OTHER INFORMATION: Synthetic Probe

<400> SEQUENCE: 344
aaaccacctc tgaaactgac                                              20

<210> SEQ ID NO 345
<211> LENGTH: 20
<212> TYPE: DNA
<213> ORGANISM: Artificial Sequence
<220> FEATURE:
<223> OTHER INFORMATION: Synthetic Probe

<400> SEQUENCE: 345
aatctttggt caagtccagg                                              20

<210> SEQ ID NO 346
<211> LENGTH: 20
<212> TYPE: DNA
<213> ORGANISM: Artificial Sequence
<220> FEATURE:
<223> OTHER INFORMATION: Synthetic Probe

<400> SEQUENCE: 346
ggtttacaga tgcagaggtg                                              20

<210> SEQ ID NO 347
<211> LENGTH: 20
<212> TYPE: DNA
<213> ORGANISM: Artificial Sequence
<220> FEATURE:
<223> OTHER INFORMATION: Synthetic Probe

<400> SEQUENCE: 347
aactgcaatc caaacgtttg                                              20

<210> SEQ ID NO 348
<211> LENGTH: 20
<212> TYPE: DNA
<213> ORGANISM: Artificial Sequence

```
<220> FEATURE:
<223> OTHER INFORMATION: Synthetic Probe

<400> SEQUENCE: 348
agaactagga caagacctca                                              20

<210> SEQ ID NO 349
<211> LENGTH: 20
<212> TYPE: DNA
<213> ORGANISM: Artificial Sequence
<220> FEATURE:
<223> OTHER INFORMATION: Synthetic Probe

<400> SEQUENCE: 349
catcttcttt caccctgagg                                              20

<210> SEQ ID NO 350
<211> LENGTH: 20
<212> TYPE: DNA
<213> ORGANISM: Artificial Sequence
<220> FEATURE:
<223> OTHER INFORMATION: Synthetic Probe

<400> SEQUENCE: 350
tctggatcgc actaacagag                                              20

<210> SEQ ID NO 351
<211> LENGTH: 20
<212> TYPE: DNA
<213> ORGANISM: Artificial Sequence
<220> FEATURE:
<223> OTHER INFORMATION: Synthetic Probe

<400> SEQUENCE: 351
catcctaaac cgtggtaccc                                              20

<210> SEQ ID NO 352
<211> LENGTH: 20
<212> TYPE: DNA
<213> ORGANISM: Artificial Sequence
<220> FEATURE:
<223> OTHER INFORMATION: Synthetic Probe

<400> SEQUENCE: 352
ggagaaagtc aagcatgtga                                              20

<210> SEQ ID NO 353
<211> LENGTH: 20
<212> TYPE: DNA
<213> ORGANISM: Artificial Sequence
<220> FEATURE:
<223> OTHER INFORMATION: Synthetic Probe

<400> SEQUENCE: 353
tttgaacctc agtccccaaa                                              20

<210> SEQ ID NO 354
<211> LENGTH: 20
<212> TYPE: DNA
<213> ORGANISM: Artificial Sequence
<220> FEATURE:
<223> OTHER INFORMATION: Synthetic Probe

<400> SEQUENCE: 354
gtacaaagag aggctggaac                                              20
```

```
<210> SEQ ID NO 355
<211> LENGTH: 20
<212> TYPE: DNA
<213> ORGANISM: Artificial Sequence
<220> FEATURE:
<223> OTHER INFORMATION: Synthetic Probe

<400> SEQUENCE: 355
cctcaacaca actatgctgt                                                    20

<210> SEQ ID NO 356
<211> LENGTH: 20
<212> TYPE: DNA
<213> ORGANISM: Artificial Sequence
<220> FEATURE:
<223> OTHER INFORMATION: Synthetic Probe

<400> SEQUENCE: 356
ctaccccata tcccaaatgc                                                    20

<210> SEQ ID NO 357
<211> LENGTH: 20
<212> TYPE: DNA
<213> ORGANISM: Artificial Sequence
<220> FEATURE:
<223> OTHER INFORMATION: Synthetic Probe

<400> SEQUENCE: 357
cacgattcag tcatctccac                                                    20

<210> SEQ ID NO 358
<211> LENGTH: 20
<212> TYPE: DNA
<213> ORGANISM: Artificial Sequence
<220> FEATURE:
<223> OTHER INFORMATION: Synthetic Probe

<400> SEQUENCE: 358
gaagtatggt ttgtgccagg                                                    20

<210> SEQ ID NO 359
<211> LENGTH: 20
<212> TYPE: DNA
<213> ORGANISM: Artificial Sequence
<220> FEATURE:
<223> OTHER INFORMATION: Synthetic Probe

<400> SEQUENCE: 359
caagtggtga cacaaccaag                                                    20

<210> SEQ ID NO 360
<211> LENGTH: 20
<212> TYPE: DNA
<213> ORGANISM: Artificial Sequence
<220> FEATURE:
<223> OTHER INFORMATION: Synthetic Probe

<400> SEQUENCE: 360
tcgaatgtca catcacacaa                                                    20

<210> SEQ ID NO 361
<211> LENGTH: 20
<212> TYPE: DNA
<213> ORGANISM: Artificial Sequence
<220> FEATURE:
<223> OTHER INFORMATION: Synthetic Probe
```

```
<400> SEQUENCE: 361
aaaaacttgg agtaccaagt                                              20

<210> SEQ ID NO 362
<211> LENGTH: 20
<212> TYPE: DNA
<213> ORGANISM: Artificial Sequence
<220> FEATURE:
<223> OTHER INFORMATION: Synthetic Probe

<400> SEQUENCE: 362
ttcatctgtc tctggtttcc                                              20

<210> SEQ ID NO 363
<211> LENGTH: 20
<212> TYPE: DNA
<213> ORGANISM: Artificial Sequence
<220> FEATURE:
<223> OTHER INFORMATION: Synthetic Probe

<400> SEQUENCE: 363
aaaccacctg taagcaaaat                                              20

<210> SEQ ID NO 364
<211> LENGTH: 20
<212> TYPE: DNA
<213> ORGANISM: Artificial Sequence
<220> FEATURE:
<223> OTHER INFORMATION: Synthetic Probe

<400> SEQUENCE: 364
gcttactcat ggaaactcgg                                              20

<210> SEQ ID NO 365
<211> LENGTH: 20
<212> TYPE: DNA
<213> ORGANISM: Artificial Sequence
<220> FEATURE:
<223> OTHER INFORMATION: Synthetic Probe

<400> SEQUENCE: 365
tcatagtcag tatctgcccc                                              20

<210> SEQ ID NO 366
<211> LENGTH: 20
<212> TYPE: DNA
<213> ORGANISM: Artificial Sequence
<220> FEATURE:
<223> OTHER INFORMATION: Synthetic Probe

<400> SEQUENCE: 366
atccgatctc gcgagaataa                                              20

<210> SEQ ID NO 367
<211> LENGTH: 20
<212> TYPE: DNA
<213> ORGANISM: Artificial Sequence
<220> FEATURE:
<223> OTHER INFORMATION: Synthetic Probe

<400> SEQUENCE: 367
gagagaagtg tgagcgtaag                                              20

<210> SEQ ID NO 368
```

```
<211> LENGTH: 20
<212> TYPE: DNA
<213> ORGANISM: Artificial Sequence
<220> FEATURE:
<223> OTHER INFORMATION: Synthetic Probe

<400> SEQUENCE: 368
atagagtaca tgggcacctt                                              20

<210> SEQ ID NO 369
<211> LENGTH: 20
<212> TYPE: DNA
<213> ORGANISM: Artificial Sequence
<220> FEATURE:
<223> OTHER INFORMATION: Synthetic Probe

<400> SEQUENCE: 369
gtaccaaatt taggggacgg                                              20

<210> SEQ ID NO 370
<211> LENGTH: 20
<212> TYPE: DNA
<213> ORGANISM: Artificial Sequence
<220> FEATURE:
<223> OTHER INFORMATION: Synthetic Probe

<400> SEQUENCE: 370
tggaatcaca aaaccttcct                                              20

<210> SEQ ID NO 371
<211> LENGTH: 20
<212> TYPE: DNA
<213> ORGANISM: Artificial Sequence
<220> FEATURE:
<223> OTHER INFORMATION: Synthetic Probe

<400> SEQUENCE: 371
cgtactggca caacaactag                                              20

<210> SEQ ID NO 372
<211> LENGTH: 20
<212> TYPE: DNA
<213> ORGANISM: Artificial Sequence
<220> FEATURE:
<223> OTHER INFORMATION: Synthetic Probe

<400> SEQUENCE: 372
gggagaatga acctcacaag                                              20

<210> SEQ ID NO 373
<211> LENGTH: 20
<212> TYPE: DNA
<213> ORGANISM: Artificial Sequence
<220> FEATURE:
<223> OTHER INFORMATION: Synthetic Probe

<400> SEQUENCE: 373
gacacaactc tcatcactgg                                              20

<210> SEQ ID NO 374
<211> LENGTH: 20
<212> TYPE: DNA
<213> ORGANISM: Artificial Sequence
<220> FEATURE:
<223> OTHER INFORMATION: Synthetic Probe

<400> SEQUENCE: 374
```
aaggctggtt ccatttatcc                                               20

<210> SEQ ID NO 375
<211> LENGTH: 20
<212> TYPE: DNA
<213> ORGANISM: Artificial Sequence
<220> FEATURE:
<223> OTHER INFORMATION: Synthetic Probe

<400> SEQUENCE: 375
tttcctactt cacaagtgcc                                               20

<210> SEQ ID NO 376
<211> LENGTH: 20
<212> TYPE: DNA
<213> ORGANISM: Artificial Sequence
<220> FEATURE:
<223> OTHER INFORMATION: Synthetic Probe

<400> SEQUENCE: 376
acctaagaaa cagggcaaag                                               20

<210> SEQ ID NO 377
<211> LENGTH: 20
<212> TYPE: DNA
<213> ORGANISM: Artificial Sequence
<220> FEATURE:
<223> OTHER INFORMATION: Synthetic Probe

<400> SEQUENCE: 377
aggcctatct ttagctctgg                                               20

<210> SEQ ID NO 378
<211> LENGTH: 20
<212> TYPE: DNA
<213> ORGANISM: Artificial Sequence
<220> FEATURE:
<223> OTHER INFORMATION: Synthetic Probe

<400> SEQUENCE: 378
gcccagaaat tccacttcat                                               20

<210> SEQ ID NO 379
<211> LENGTH: 20
<212> TYPE: DNA
<213> ORGANISM: Artificial Sequence
<220> FEATURE:
<223> OTHER INFORMATION: Synthetic Probe

<400> SEQUENCE: 379
aaccctgtta tcaccatcac                                               20

<210> SEQ ID NO 380
<211> LENGTH: 20
<212> TYPE: DNA
<213> ORGANISM: Artificial Sequence
<220> FEATURE:
<223> OTHER INFORMATION: Synthetic Probe

<400> SEQUENCE: 380
gaggactcac tgagcgaaag                                               20

<210> SEQ ID NO 381
<211> LENGTH: 20
<212> TYPE: DNA

```
<213> ORGANISM: Artificial Sequence
<220> FEATURE:
<223> OTHER INFORMATION: Synthetic Probe

<400> SEQUENCE: 381
tgcatttttc caggaactaa                                                    20

<210> SEQ ID NO 382
<211> LENGTH: 20
<212> TYPE: DNA
<213> ORGANISM: Artificial Sequence
<220> FEATURE:
<223> OTHER INFORMATION: Synthetic Probe

<400> SEQUENCE: 382
tgagcccgta ttctcattga                                                    20

<210> SEQ ID NO 383
<211> LENGTH: 20
<212> TYPE: DNA
<213> ORGANISM: Artificial Sequence
<220> FEATURE:
<223> OTHER INFORMATION: Synthetic Probe

<400> SEQUENCE: 383
aattaaaact cacaggaggc                                                    20

<210> SEQ ID NO 384
<211> LENGTH: 20
<212> TYPE: DNA
<213> ORGANISM: Artificial Sequence
<220> FEATURE:
<223> OTHER INFORMATION: Synthetic Probe

<400> SEQUENCE: 384
atgccaagct aacaatgctc                                                    20

<210> SEQ ID NO 385
<211> LENGTH: 20
<212> TYPE: DNA
<213> ORGANISM: Artificial Sequence
<220> FEATURE:
<223> OTHER INFORMATION: Synthetic Probe

<400> SEQUENCE: 385
gtgtccatcg ttaccagggc                                                    20

<210> SEQ ID NO 386
<211> LENGTH: 20
<212> TYPE: DNA
<213> ORGANISM: Artificial Sequence
<220> FEATURE:
<223> OTHER INFORMATION: Synthetic Probe

<400> SEQUENCE: 386
taggcaaaga ggtagagccc                                                    20

<210> SEQ ID NO 387
<211> LENGTH: 20
<212> TYPE: DNA
<213> ORGANISM: Artificial Sequence
<220> FEATURE:
<223> OTHER INFORMATION: Synthetic Probe

<400> SEQUENCE: 387
aaggactgca gagtgtcaat                                                    20
```

<210> SEQ ID NO 388
<211> LENGTH: 20
<212> TYPE: DNA
<213> ORGANISM: Artificial Sequence
<220> FEATURE:
<223> OTHER INFORMATION: Synthetic Probe

<400> SEQUENCE: 388
acaaagtaga gacctatcca                                               20

<210> SEQ ID NO 389
<211> LENGTH: 20
<212> TYPE: DNA
<213> ORGANISM: Artificial Sequence
<220> FEATURE:
<223> OTHER INFORMATION: Synthetic Probe

<400> SEQUENCE: 389
cacctggggt gggaaaagag                                               20

<210> SEQ ID NO 390
<211> LENGTH: 20
<212> TYPE: DNA
<213> ORGANISM: Artificial Sequence
<220> FEATURE:
<223> OTHER INFORMATION: Synthetic Probe

<400> SEQUENCE: 390
gagagggcag catggaatgg                                               20

<210> SEQ ID NO 391
<211> LENGTH: 20
<212> TYPE: DNA
<213> ORGANISM: Artificial Sequence
<220> FEATURE:
<223> OTHER INFORMATION: Synthetic Probe

<400> SEQUENCE: 391
cagtttgagc aggttgaggg                                               20

<210> SEQ ID NO 392
<211> LENGTH: 20
<212> TYPE: DNA
<213> ORGANISM: Artificial Sequence
<220> FEATURE:
<223> OTHER INFORMATION: Synthetic Probe

<400> SEQUENCE: 392
aaaggacact cagtctacct                                               20

<210> SEQ ID NO 393
<211> LENGTH: 20
<212> TYPE: DNA
<213> ORGANISM: Artificial Sequence
<220> FEATURE:
<223> OTHER INFORMATION: Synthetic Probe

<400> SEQUENCE: 393
ctgtgggcaa ggaacagatc                                               20

<210> SEQ ID NO 394
<211> LENGTH: 20
<212> TYPE: DNA
<213> ORGANISM: Artificial Sequence
<220> FEATURE:

<223> OTHER INFORMATION: Synthetic Probe

<400> SEQUENCE: 394
caaacagaat gccccgcacc                                               20

<210> SEQ ID NO 395
<211> LENGTH: 20
<212> TYPE: DNA
<213> ORGANISM: Artificial Sequence
<220> FEATURE:
<223> OTHER INFORMATION: Synthetic Probe

<400> SEQUENCE: 395
gtgaatagag ggtgccccat                                               20

<210> SEQ ID NO 396
<211> LENGTH: 20
<212> TYPE: DNA
<213> ORGANISM: Artificial Sequence
<220> FEATURE:
<223> OTHER INFORMATION: Synthetic Probe

<400> SEQUENCE: 396
tctcttgaga caatctggga                                               20

<210> SEQ ID NO 397
<211> LENGTH: 20
<212> TYPE: DNA
<213> ORGANISM: Artificial Sequence
<220> FEATURE:
<223> OTHER INFORMATION: Synthetic Probe

<400> SEQUENCE: 397
cctttgcttg acttcgactt                                               20

<210> SEQ ID NO 398
<211> LENGTH: 20
<212> TYPE: DNA
<213> ORGANISM: Artificial Sequence
<220> FEATURE:
<223> OTHER INFORMATION: Synthetic Probe

<400> SEQUENCE: 398
tgttatctca ctggacctga                                               20

<210> SEQ ID NO 399
<211> LENGTH: 20
<212> TYPE: DNA
<213> ORGANISM: Artificial Sequence
<220> FEATURE:
<223> OTHER INFORMATION: Synthetic Probe

<400> SEQUENCE: 399
ctttttttag ggggtggtgg                                               20

<210> SEQ ID NO 400
<211> LENGTH: 20
<212> TYPE: DNA
<213> ORGANISM: Artificial Sequence
<220> FEATURE:
<223> OTHER INFORMATION: Synthetic Probe

<400> SEQUENCE: 400
ctctgatcca accaaagtgg                                               20

```
<210> SEQ ID NO 401
<211> LENGTH: 20
<212> TYPE: DNA
<213> ORGANISM: Artificial Sequence
<220> FEATURE:
<223> OTHER INFORMATION: Synthetic Probe

<400> SEQUENCE: 401
ggaacacagt agtagatgca                                              20

<210> SEQ ID NO 402
<211> LENGTH: 20
<212> TYPE: DNA
<213> ORGANISM: Artificial Sequence
<220> FEATURE:
<223> OTHER INFORMATION: Synthetic Probe

<400> SEQUENCE: 402
accagacacc tgagaagtaa                                              20

<210> SEQ ID NO 403
<211> LENGTH: 20
<212> TYPE: DNA
<213> ORGANISM: Artificial Sequence
<220> FEATURE:
<223> OTHER INFORMATION: Synthetic Probe

<400> SEQUENCE: 403
ctggtttgtg attgctacct                                              20

<210> SEQ ID NO 404
<211> LENGTH: 20
<212> TYPE: DNA
<213> ORGANISM: Artificial Sequence
<220> FEATURE:
<223> OTHER INFORMATION: Synthetic Probe

<400> SEQUENCE: 404
gtgcatcaaa caagggatct                                              20

<210> SEQ ID NO 405
<211> LENGTH: 20
<212> TYPE: DNA
<213> ORGANISM: Artificial Sequence
<220> FEATURE:
<223> OTHER INFORMATION: Synthetic Probe

<400> SEQUENCE: 405
ggcaactaac atatcctggg                                              20

<210> SEQ ID NO 406
<211> LENGTH: 20
<212> TYPE: DNA
<213> ORGANISM: Artificial Sequence
<220> FEATURE:
<223> OTHER INFORMATION: Synthetic Probe

<400> SEQUENCE: 406
acacagccac atgaaatctt                                              20

<210> SEQ ID NO 407
<211> LENGTH: 20
<212> TYPE: DNA
<213> ORGANISM: Artificial Sequence
<220> FEATURE:
<223> OTHER INFORMATION: Synthetic Probe
```

```
<400> SEQUENCE: 407
gcactctcca tctaccaaac                                              20

<210> SEQ ID NO 408
<211> LENGTH: 20
<212> TYPE: DNA
<213> ORGANISM: Artificial Sequence
<220> FEATURE:
<223> OTHER INFORMATION: Synthetic Probe

<400> SEQUENCE: 408
taagtgactg ggacaagtca                                              20

<210> SEQ ID NO 409
<211> LENGTH: 20
<212> TYPE: DNA
<213> ORGANISM: Artificial Sequence
<220> FEATURE:
<223> OTHER INFORMATION: Synthetic Probe

<400> SEQUENCE: 409
ggcaatcaaa tgtccacaga                                              20

<210> SEQ ID NO 410
<211> LENGTH: 20
<212> TYPE: DNA
<213> ORGANISM: Artificial Sequence
<220> FEATURE:
<223> OTHER INFORMATION: Synthetic Probe

<400> SEQUENCE: 410
cactctccaa aggtcacaat                                              20

<210> SEQ ID NO 411
<211> LENGTH: 20
<212> TYPE: DNA
<213> ORGANISM: Artificial Sequence
<220> FEATURE:
<223> OTHER INFORMATION: Synthetic Probe

<400> SEQUENCE: 411
atccagtgct acagcttaga                                              20

<210> SEQ ID NO 412
<211> LENGTH: 20
<212> TYPE: DNA
<213> ORGANISM: Artificial Sequence
<220> FEATURE:
<223> OTHER INFORMATION: Synthetic Probe

<400> SEQUENCE: 412
atcacctcct agtgctgtta                                              20

<210> SEQ ID NO 413
<211> LENGTH: 20
<212> TYPE: DNA
<213> ORGANISM: Artificial Sequence
<220> FEATURE:
<223> OTHER INFORMATION: Synthetic Probe

<400> SEQUENCE: 413
ccatcattct aagccccaag                                              20

<210> SEQ ID NO 414
<211> LENGTH: 20
```

```
<212> TYPE: DNA
<213> ORGANISM: Artificial Sequence
<220> FEATURE:
<223> OTHER INFORMATION: Synthetic Probe

<400> SEQUENCE: 414
ctgctatgac attccatccc                                           20

<210> SEQ ID NO 415
<211> LENGTH: 20
<212> TYPE: DNA
<213> ORGANISM: Artificial Sequence
<220> FEATURE:
<223> OTHER INFORMATION: Synthetic Probe

<400> SEQUENCE: 415
gatcacaaga gaagtctggc                                           20

<210> SEQ ID NO 416
<211> LENGTH: 20
<212> TYPE: DNA
<213> ORGANISM: Artificial Sequence
<220> FEATURE:
<223> OTHER INFORMATION: Synthetic Probe

<400> SEQUENCE: 416
gaacaccaga acagaactcc                                           20

<210> SEQ ID NO 417
<211> LENGTH: 20
<212> TYPE: DNA
<213> ORGANISM: Artificial Sequence
<220> FEATURE:
<223> OTHER INFORMATION: Synthetic Probe

<400> SEQUENCE: 417
cacagaattg tcccaaggat                                           20

<210> SEQ ID NO 418
<211> LENGTH: 20
<212> TYPE: DNA
<213> ORGANISM: Artificial Sequence
<220> FEATURE:
<223> OTHER INFORMATION: Synthetic Probe

<400> SEQUENCE: 418
aagctgagca actttaggtc                                           20

<210> SEQ ID NO 419
<211> LENGTH: 20
<212> TYPE: DNA
<213> ORGANISM: Artificial Sequence
<220> FEATURE:
<223> OTHER INFORMATION: Synthetic Probe

<400> SEQUENCE: 419
ttgcttgctc aaatctcact                                           20

<210> SEQ ID NO 420
<211> LENGTH: 20
<212> TYPE: DNA
<213> ORGANISM: Artificial Sequence
<220> FEATURE:
<223> OTHER INFORMATION: Synthetic Probe

<400> SEQUENCE: 420
```
tacagcctag ttagacaggg                                               20

<210> SEQ ID NO 421
<211> LENGTH: 20
<212> TYPE: DNA
<213> ORGANISM: Artificial Sequence
<220> FEATURE:
<223> OTHER INFORMATION: Synthetic Probe

<400> SEQUENCE: 421
gattccacct gtaaagaggc                                               20

<210> SEQ ID NO 422
<211> LENGTH: 20
<212> TYPE: DNA
<213> ORGANISM: Artificial Sequence
<220> FEATURE:
<223> OTHER INFORMATION: Synthetic Probe

<400> SEQUENCE: 422
cacagcagaa catctcacaa                                               20

<210> SEQ ID NO 423
<211> LENGTH: 20
<212> TYPE: DNA
<213> ORGANISM: Artificial Sequence
<220> FEATURE:
<223> OTHER INFORMATION: Synthetic Probe

<400> SEQUENCE: 423
gagaagagaa acgctgtcac                                               20

<210> SEQ ID NO 424
<211> LENGTH: 20
<212> TYPE: DNA
<213> ORGANISM: Artificial Sequence
<220> FEATURE:
<223> OTHER INFORMATION: Synthetic Probe

<400> SEQUENCE: 424
tctggcacta tatctccgag                                               20

<210> SEQ ID NO 425
<211> LENGTH: 20
<212> TYPE: DNA
<213> ORGANISM: Artificial Sequence
<220> FEATURE:
<223> OTHER INFORMATION: Synthetic Probe

<400> SEQUENCE: 425
taggtcccca aactgagtag                                               20

<210> SEQ ID NO 426
<211> LENGTH: 20
<212> TYPE: DNA
<213> ORGANISM: Artificial Sequence
<220> FEATURE:
<223> OTHER INFORMATION: Synthetic Probe

<400> SEQUENCE: 426
agagactcag agaaaggagg                                               20

<210> SEQ ID NO 427
<211> LENGTH: 20
<212> TYPE: DNA
<213> ORGANISM: Artificial Sequence
<220> FEATURE:
<223> OTHER INFORMATION: Synthetic Probe

<400> SEQUENCE: 427
tgtgacgata ctggacagat                                                20

<210> SEQ ID NO 428
<211> LENGTH: 20
<212> TYPE: DNA
<213> ORGANISM: Artificial Sequence
<220> FEATURE:
<223> OTHER INFORMATION: Synthetic Probe

<400> SEQUENCE: 428
ctaaagtcag cacaacccac                                                20

<210> SEQ ID NO 429
<211> LENGTH: 20
<212> TYPE: DNA
<213> ORGANISM: Artificial Sequence
<220> FEATURE:
<223> OTHER INFORMATION: Synthetic Probe

<400> SEQUENCE: 429
gagaagcaag ggcaaaacag                                                20

<210> SEQ ID NO 430
<211> LENGTH: 20
<212> TYPE: DNA
<213> ORGANISM: Artificial Sequence
<220> FEATURE:
<223> OTHER INFORMATION: Synthetic Probe

<400> SEQUENCE: 430
caaacgttct tcagatcaca                                                20

<210> SEQ ID NO 431
<211> LENGTH: 20
<212> TYPE: DNA
<213> ORGANISM: Artificial Sequence
<220> FEATURE:
<223> OTHER INFORMATION: Synthetic Probe

<400> SEQUENCE: 431
ggccaactga ggtagaagat                                                20

<210> SEQ ID NO 432
<211> LENGTH: 20
<212> TYPE: DNA
<213> ORGANISM: Artificial Sequence
<220> FEATURE:
<223> OTHER INFORMATION: Synthetic Probe

<400> SEQUENCE: 432 cactacccccc agtttctcaa                                               20

<210> SEQ ID NO 433
<211> LENGTH: 20
<212> TYPE: DNA
<213> ORGANISM: Artificial Sequence
<220> FEATURE:
<223> OTHER INFORMATION: Synthetic Probe

<400> SEQUENCE: 433
tattactggc agtgtcctct                                                20

<210> SEQ ID NO 434
<211> LENGTH: 20
<212> TYPE: DNA
<213> ORGANISM: Artificial Sequence
<220> FEATURE:
<223> OTHER INFORMATION: Synthetic Probe

<400> SEQUENCE: 434
gaggctcagt tagaggctct                                               20

<210> SEQ ID NO 435
<211> LENGTH: 20
<212> TYPE: DNA
<213> ORGANISM: Artificial Sequence
<220> FEATURE:
<223> OTHER INFORMATION: Synthetic Probe

<400> SEQUENCE: 435
caatgctcct ttcctaggac                                               20

<210> SEQ ID NO 436
<211> LENGTH: 20
<212> TYPE: DNA
<213> ORGANISM: Artificial Sequence
<220> FEATURE:
<223> OTHER INFORMATION: Synthetic Probe

<400> SEQUENCE: 436
acactgaatt cttgtcgctc                                               20

<210> SEQ ID NO 437
<211> LENGTH: 20
<212> TYPE: DNA
<213> ORGANISM: Artificial Sequence
<220> FEATURE:
<223> OTHER INFORMATION: Synthetic Probe

<400> SEQUENCE: 437
aaggtcagac actgaagtct                                               20

<210> SEQ ID NO 438
<211> LENGTH: 20
<212> TYPE: DNA
<213> ORGANISM: Artificial Sequence
<220> FEATURE:
<223> OTHER INFORMATION: Synthetic Probe

<400> SEQUENCE: 438
ccgacctcta agtggttcag                                               20

<210> SEQ ID NO 439
<211> LENGTH: 20
<212> TYPE: DNA
<213> ORGANISM: Artificial Sequence
<220> FEATURE:
<223> OTHER INFORMATION: Synthetic Probe

<400> SEQUENCE: 439
gcatccatct gggtttctaa                                               20

<210> SEQ ID NO 440
<211> LENGTH: 20
<212> TYPE: DNA
<213> ORGANISM: Artificial Sequence
<220> FEATURE:
<223> OTHER INFORMATION: Synthetic Probe

<400> SEQUENCE: 440
ggagtctgag actgacacat                                               20

<210> SEQ ID NO 441
<211> LENGTH: 20
<212> TYPE: DNA
<213> ORGANISM: Artificial Sequence
<220> FEATURE:
<223> OTHER INFORMATION: Synthetic Probe

<400> SEQUENCE: 441
cgtgtggaag atacactgtc                                               20

<210> SEQ ID NO 442
<211> LENGTH: 20
<212> TYPE: DNA
<213> ORGANISM: Artificial Sequence
<220> FEATURE:
<223> OTHER INFORMATION: Synthetic Probe

<400> SEQUENCE: 442
gcctatagtc tgctgctttc                                               20

<210> SEQ ID NO 443
<211> LENGTH: 20
<212> TYPE: DNA
<213> ORGANISM: Artificial Sequence
<220> FEATURE:
<223> OTHER INFORMATION: Synthetic Probe

<400> SEQUENCE: 443
caagcatcgg agcacacata                                               20

<210> SEQ ID NO 444
<211> LENGTH: 20
<212> TYPE: DNA
<213> ORGANISM: Artificial Sequence
<220> FEATURE:
<223> OTHER INFORMATION: Synthetic Probe

<400> SEQUENCE: 444
gagtcacact ggttttcagg                                               20

<210> SEQ ID NO 445
<211> LENGTH: 20
<212> TYPE: DNA
<213> ORGANISM: Artificial Sequence
<220> FEATURE:
<223> OTHER INFORMATION: Synthetic Probe

<400> SEQUENCE: 445
cttctctgat aagccgtgac                                               20

<210> SEQ ID NO 446
<211> LENGTH: 20
<212> TYPE: DNA
<213> ORGANISM: Artificial Sequence
<220> FEATURE:
<223> OTHER INFORMATION: Synthetic Probe

<400> SEQUENCE: 446
gagaggacag ctggtaactg                                               20

<210> SEQ ID NO 447

```
<211> LENGTH: 20
<212> TYPE: DNA
<213> ORGANISM: Artificial Sequence
<220> FEATURE:
<223> OTHER INFORMATION: Synthetic Probe

<400> SEQUENCE: 447
ttttgaacac attggggtcc                                              20

<210> SEQ ID NO 448
<211> LENGTH: 20
<212> TYPE: DNA
<213> ORGANISM: Artificial Sequence
<220> FEATURE:
<223> OTHER INFORMATION: Synthetic Probe

<400> SEQUENCE: 448
gtgccactac tgaaaggatg                                              20

<210> SEQ ID NO 449
<211> LENGTH: 20
<212> TYPE: DNA
<213> ORGANISM: Artificial Sequence
<220> FEATURE:
<223> OTHER INFORMATION: Synthetic Probe

<400> SEQUENCE: 449
gactgctctg actcttcacc                                              20

<210> SEQ ID NO 450
<211> LENGTH: 20
<212> TYPE: DNA
<213> ORGANISM: Artificial Sequence
<220> FEATURE:
<223> OTHER INFORMATION: Synthetic Probe

<400> SEQUENCE: 450
ggtacgcact tatgaggaac                                              20

<210> SEQ ID NO 451
<211> LENGTH: 20
<212> TYPE: DNA
<213> ORGANISM: Artificial Sequence
<220> FEATURE:
<223> OTHER INFORMATION: Synthetic Probe

<400> SEQUENCE: 451
tctctgctgc tacatctcag                                              20

<210> SEQ ID NO 452
<211> LENGTH: 20
<212> TYPE: DNA
<213> ORGANISM: Artificial Sequence
<220> FEATURE:
<223> OTHER INFORMATION: Synthetic Probe

<400> SEQUENCE: 452
catgagaagg gagacggatg                                              20

<210> SEQ ID NO 453
<211> LENGTH: 20
<212> TYPE: DNA
<213> ORGANISM: Artificial Sequence
<220> FEATURE:
<223> OTHER INFORMATION: Synthetic Probe

<400> SEQUENCE: 453
```
atcccagaca ataagagggg                                            20

<210> SEQ ID NO 454
<211> LENGTH: 20
<212> TYPE: DNA
<213> ORGANISM: Artificial Sequence
<220> FEATURE:
<223> OTHER INFORMATION: Synthetic Probe

<400> SEQUENCE: 454
cgaggataga gaagccagag                                            20

<210> SEQ ID NO 455
<211> LENGTH: 20
<212> TYPE: DNA
<213> ORGANISM: Artificial Sequence
<220> FEATURE:
<223> OTHER INFORMATION: Synthetic Probe

<400> SEQUENCE: 455 cccactttg ggaacaatga                                             20

<210> SEQ ID NO 456
<211> LENGTH: 20
<212> TYPE: DNA
<213> ORGANISM: Artificial Sequence
<220> FEATURE:
<223> OTHER INFORMATION: Synthetic Probe

<400> SEQUENCE: 456
gctgcgtttg tgatttgtta                                            20

<210> SEQ ID NO 457
<211> LENGTH: 20
<212> TYPE: DNA
<213> ORGANISM: Artificial Sequence
<220> FEATURE:
<223> OTHER INFORMATION: Synthetic Probe

<400> SEQUENCE: 457
ggatgaaagc agaggtcaag                                            20

<210> SEQ ID NO 458
<211> LENGTH: 20
<212> TYPE: DNA
<213> ORGANISM: Artificial Sequence
<220> FEATURE:
<223> OTHER INFORMATION: Synthetic Probe

<400> SEQUENCE: 458
ggatgaaagc agaggtcaag                                            20

<210> SEQ ID NO 459
<211> LENGTH: 20
<212> TYPE: DNA
<213> ORGANISM: Artificial Sequence
<220> FEATURE:
<223> OTHER INFORMATION: Synthetic Probe

<400> SEQUENCE: 459
taagtgggtc aaggtcagag                                            20

<210> SEQ ID NO 460
<211> LENGTH: 20
<212> TYPE: DNA

```
<213> ORGANISM: Artificial Sequence
<220> FEATURE:
<223> OTHER INFORMATION: Synthetic Probe

<400> SEQUENCE: 460
gattgtggag ctgactgaag                                              20

<210> SEQ ID NO 461
<211> LENGTH: 20
<212> TYPE: DNA
<213> ORGANISM: Artificial Sequence
<220> FEATURE:
<223> OTHER INFORMATION: Synthetic Probe

<400> SEQUENCE: 461
catcttatcg ctgaagggga                                              20

<210> SEQ ID NO 462
<211> LENGTH: 20
<212> TYPE: DNA
<213> ORGANISM: Artificial Sequence
<220> FEATURE:
<223> OTHER INFORMATION: Synthetic Probe

<400> SEQUENCE: 462
ctgcacaatc tgggagagac                                              20

<210> SEQ ID NO 463
<211> LENGTH: 20
<212> TYPE: DNA
<213> ORGANISM: Artificial Sequence
<220> FEATURE:
<223> OTHER INFORMATION: Synthetic Probe

<400> SEQUENCE: 463
gagttaggct ggaggaacag                                              20

<210> SEQ ID NO 464
<211> LENGTH: 20
<212> TYPE: DNA
<213> ORGANISM: Artificial Sequence
<220> FEATURE:
<223> OTHER INFORMATION: Synthetic Probe

<400> SEQUENCE: 464
tggtaagata gctgcgtcta                                              20

<210> SEQ ID NO 465
<211> LENGTH: 20
<212> TYPE: DNA
<213> ORGANISM: Artificial Sequence
<220> FEATURE:
<223> OTHER INFORMATION: Synthetic Probe

<400> SEQUENCE: 465
actgaagaca catcaccta                                               20

<210> SEQ ID NO 466
<211> LENGTH: 20
<212> TYPE: DNA
<213> ORGANISM: Artificial Sequence
<220> FEATURE:
<223> OTHER INFORMATION: Synthetic Probe

<400> SEQUENCE: 466
tccaagaaaa aactgaaggg                                              20
```

<210> SEQ ID NO 467
<211> LENGTH: 20
<212> TYPE: DNA
<213> ORGANISM: Artificial Sequence
<220> FEATURE:
<223> OTHER INFORMATION: Synthetic Probe

<400> SEQUENCE: 467
agagaatatg acccagaagc                                              20

<210> SEQ ID NO 468
<211> LENGTH: 20
<212> TYPE: DNA
<213> ORGANISM: Artificial Sequence
<220> FEATURE:
<223> OTHER INFORMATION: Synthetic Probe

<400> SEQUENCE: 468
tcaatacctc aggttgtcct                                              20

<210> SEQ ID NO 469
<211> LENGTH: 20
<212> TYPE: DNA
<213> ORGANISM: Artificial Sequence
<220> FEATURE:
<223> OTHER INFORMATION: Synthetic Probe

<400> SEQUENCE: 469
gtccacactt gagaagctaa                                              20

<210> SEQ ID NO 470
<211> LENGTH: 20
<212> TYPE: DNA
<213> ORGANISM: Artificial Sequence
<220> FEATURE:
<223> OTHER INFORMATION: Synthetic Probe

<400> SEQUENCE: 470
cactattttt ctgcccccta                                              20

<210> SEQ ID NO 471
<211> LENGTH: 20
<212> TYPE: DNA
<213> ORGANISM: Artificial Sequence
<220> FEATURE:
<223> OTHER INFORMATION: Synthetic Probe

<400> SEQUENCE: 471
gcaagttctt acgccatcta                                              20

<210> SEQ ID NO 472
<211> LENGTH: 20
<212> TYPE: DNA
<213> ORGANISM: Artificial Sequence
<220> FEATURE:
<223> OTHER INFORMATION: Synthetic Probe

<400> SEQUENCE: 472
gtgcctcagg cacattatac                                              20

<210> SEQ ID NO 473
<211> LENGTH: 20
<212> TYPE: DNA
<213> ORGANISM: Artificial Sequence
<220> FEATURE:

<223> OTHER INFORMATION: Synthetic Probe

<400> SEQUENCE: 473
aggagactct gaactatgcc                                               20

<210> SEQ ID NO 474
<211> LENGTH: 20
<212> TYPE: DNA
<213> ORGANISM: Artificial Sequence
<220> FEATURE:
<223> OTHER INFORMATION: Synthetic Probe

<400> SEQUENCE: 474
ttaagtgctc aataacccccc                                              20

<210> SEQ ID NO 475
<211> LENGTH: 20
<212> TYPE: DNA
<213> ORGANISM: Artificial Sequence
<220> FEATURE:
<223> OTHER INFORMATION: Synthetic Probe

<400> SEQUENCE: 475
tcaagtcagg ccattcaatt                                               20

<210> SEQ ID NO 476
<211> LENGTH: 20
<212> TYPE: DNA
<213> ORGANISM: Artificial Sequence
<220> FEATURE:
<223> OTHER INFORMATION: Synthetic Probe

<400> SEQUENCE: 476
cacctgaagg aagacggcgg                                               20

<210> SEQ ID NO 477
<211> LENGTH: 20
<212> TYPE: DNA
<213> ORGANISM: Artificial Sequence
<220> FEATURE:
<223> OTHER INFORMATION: Synthetic Probe

<400> SEQUENCE: 477
ctgatcttcc ctaggaggac                                               20

<210> SEQ ID NO 478
<211> LENGTH: 20
<212> TYPE: DNA
<213> ORGANISM: Artificial Sequence
<220> FEATURE:
<223> OTHER INFORMATION: Synthetic Probe

<400> SEQUENCE: 478
tcctaggaac aagaccacag                                               20

<210> SEQ ID NO 479
<211> LENGTH: 20
<212> TYPE: DNA
<213> ORGANISM: Artificial Sequence
<220> FEATURE:
<223> OTHER INFORMATION: Synthetic Probe

<400> SEQUENCE: 479
ttcggggaca ggacagagtg                                               20

```
<210> SEQ ID NO 480
<211> LENGTH: 20
<212> TYPE: DNA
<213> ORGANISM: Artificial Sequence
<220> FEATURE:
<223> OTHER INFORMATION: Synthetic Probe

<400> SEQUENCE: 480
aggggcaagt ctaagagctg                                          20

<210> SEQ ID NO 481
<211> LENGTH: 20
<212> TYPE: DNA
<213> ORGANISM: Artificial Sequence
<220> FEATURE:
<223> OTHER INFORMATION: Synthetic Probe

<400> SEQUENCE: 481
cagggagtat cttaggccag                                          20

<210> SEQ ID NO 482
<211> LENGTH: 20
<212> TYPE: DNA
<213> ORGANISM: Artificial Sequence
<220> FEATURE:
<223> OTHER INFORMATION: Synthetic Probe

<400> SEQUENCE: 482
ccgggaatct ttgggatctg                                          20

<210> SEQ ID NO 483
<211> LENGTH: 20
<212> TYPE: DNA
<213> ORGANISM: Artificial Sequence
<220> FEATURE:
<223> OTHER INFORMATION: Synthetic Probe

<400> SEQUENCE: 483
tgagccattg aaggccacac                                          20

<210> SEQ ID NO 484
<211> LENGTH: 20
<212> TYPE: DNA
<213> ORGANISM: Artificial Sequence
<220> FEATURE:
<223> OTHER INFORMATION: Synthetic Probe

<400> SEQUENCE: 484
gaccctgcaa caaatccatg                                          20

<210> SEQ ID NO 485
<211> LENGTH: 20
<212> TYPE: DNA
<213> ORGANISM: Artificial Sequence
<220> FEATURE:
<223> OTHER INFORMATION: Synthetic Probe

<400> SEQUENCE: 485
ctacgctgtt ctcagtactg                                          20

<210> SEQ ID NO 486
<211> LENGTH: 20
<212> TYPE: DNA
<213> ORGANISM: Artificial Sequence
<220> FEATURE:
<223> OTHER INFORMATION: Synthetic Probe
```

<400> SEQUENCE: 486
tggaacccgc aattggagga                                         20

<210> SEQ ID NO 487
<211> LENGTH: 20
<212> TYPE: DNA
<213> ORGANISM: Artificial Sequence
<220> FEATURE:
<223> OTHER INFORMATION: Synthetic Probe

<400> SEQUENCE: 487
ggagatgaga cagagaggag                                         20

<210> SEQ ID NO 488
<211> LENGTH: 20
<212> TYPE: DNA
<213> ORGANISM: Artificial Sequence
<220> FEATURE:
<223> OTHER INFORMATION: Synthetic Probe

<400> SEQUENCE: 488
agggagaagc cagagaaagg                                         20

<210> SEQ ID NO 489
<211> LENGTH: 20
<212> TYPE: DNA
<213> ORGANISM: Artificial Sequence
<220> FEATURE:
<223> OTHER INFORMATION: Synthetic Probe

<400> SEQUENCE: 489
tctagagact taacaggtcg                                         20

<210> SEQ ID NO 490
<211> LENGTH: 20
<212> TYPE: DNA
<213> ORGANISM: Artificial Sequence
<220> FEATURE:
<223> OTHER INFORMATION: Synthetic Probe

<400> SEQUENCE: 490
cgacatagtt gcagagtgac                                         20

<210> SEQ ID NO 491
<211> LENGTH: 20
<212> TYPE: DNA
<213> ORGANISM: Artificial Sequence
<220> FEATURE:
<223> OTHER INFORMATION: Synthetic Probe

<400> SEQUENCE: 491
ggaagagtta gcttaggaac                                         20

<210> SEQ ID NO 492
<211> LENGTH: 20
<212> TYPE: DNA
<213> ORGANISM: Artificial Sequence
<220> FEATURE:
<223> OTHER INFORMATION: Synthetic Probe

<400> SEQUENCE: 492
tgtatgacgc taggttcatc                                         20

<210> SEQ ID NO 493
<211> LENGTH: 20

<212> TYPE: DNA
<213> ORGANISM: Artificial Sequence
<220> FEATURE:
<223> OTHER INFORMATION: Synthetic Probe

<400> SEQUENCE: 493
acccaaaact ctgacattct                                           20

<210> SEQ ID NO 494
<211> LENGTH: 20
<212> TYPE: DNA
<213> ORGANISM: Artificial Sequence
<220> FEATURE:
<223> OTHER INFORMATION: Synthetic Probe

<400> SEQUENCE: 494
taacttatat ggactcccag                                           20

<210> SEQ ID NO 495
<211> LENGTH: 20
<212> TYPE: DNA
<213> ORGANISM: Artificial Sequence
<220> FEATURE:
<223> OTHER INFORMATION: Synthetic Probe

<400> SEQUENCE: 495
cttttcaccc agaacatata                                           20

<210> SEQ ID NO 496
<211> LENGTH: 20
<212> TYPE: DNA
<213> ORGANISM: Artificial Sequence
<220> FEATURE:
<223> OTHER INFORMATION: Synthetic Probe

<400> SEQUENCE: 496
tgatgcctag gacatccaac                                           20

<210> SEQ ID NO 497
<211> LENGTH: 20
<212> TYPE: DNA
<213> ORGANISM: Artificial Sequence
<220> FEATURE:
<223> OTHER INFORMATION: Synthetic Probe

<400> SEQUENCE: 497
tatctgaaga ccagaatggc                                           20

<210> SEQ ID NO 498
<211> LENGTH: 20
<212> TYPE: DNA
<213> ORGANISM: Artificial Sequence
<220> FEATURE:
<223> OTHER INFORMATION: Synthetic Probe

<400> SEQUENCE: 498
catctcattc tatggatgag                                           20

<210> SEQ ID NO 499
<211> LENGTH: 20
<212> TYPE: DNA
<213> ORGANISM: Artificial Sequence
<220> FEATURE:
<223> OTHER INFORMATION: Synthetic Probe

<400> SEQUENCE: 499
cagaatgtct gacagctcat                                              20

<210> SEQ ID NO 500
<211> LENGTH: 20
<212> TYPE: DNA
<213> ORGANISM: Artificial Sequence
<220> FEATURE:
<223> OTHER INFORMATION: Synthetic Probe

<400> SEQUENCE: 500
atacccaaca cacacgtgac                                              20

<210> SEQ ID NO 501
<211> LENGTH: 20
<212> TYPE: DNA
<213> ORGANISM: Artificial Sequence
<220> FEATURE:
<223> OTHER INFORMATION: Synthetic Probe

<400> SEQUENCE: 501
attgacttgc cttatctgat                                              20

<210> SEQ ID NO 502
<211> LENGTH: 20
<212> TYPE: DNA
<213> ORGANISM: Artificial Sequence
<220> FEATURE:
<223> OTHER INFORMATION: Synthetic Probe

<400> SEQUENCE: 502
caagatgcct gactcaccac                                              20

<210> SEQ ID NO 503
<211> LENGTH: 20
<212> TYPE: DNA
<213> ORGANISM: Artificial Sequence
<220> FEATURE:
<223> OTHER INFORMATION: Synthetic Probe

<400> SEQUENCE: 503
atatctatat ccttggaacc                                              20

<210> SEQ ID NO 504
<211> LENGTH: 20
<212> TYPE: DNA
<213> ORGANISM: Artificial Sequence
<220> FEATURE:
<223> OTHER INFORMATION: Synthetic Probe

<400> SEQUENCE: 504
taagagcttg tactttcttg                                              20

<210> SEQ ID NO 505
<211> LENGTH: 20
<212> TYPE: DNA
<213> ORGANISM: Artificial Sequence
<220> FEATURE:
<223> OTHER INFORMATION: Synthetic Probe

<400> SEQUENCE: 505
tcataacgct acacatctgg                                              20

<210> SEQ ID NO 506
<211> LENGTH: 20
<212> TYPE: DNA
<213> ORGANISM: Artificial Sequence

```
<220> FEATURE:
<223> OTHER INFORMATION: Synthetic Probe

<400> SEQUENCE: 506
atatcaggat acagggaacc                                                  20

<210> SEQ ID NO 507
<211> LENGTH: 20
<212> TYPE: DNA
<213> ORGANISM: Artificial Sequence
<220> FEATURE:
<223> OTHER INFORMATION: Synthetic Probe

<400> SEQUENCE: 507
tgagattgtg acatcctgag                                                  20

<210> SEQ ID NO 508
<211> LENGTH: 20
<212> TYPE: DNA
<213> ORGANISM: Artificial Sequence
<220> FEATURE:
<223> OTHER INFORMATION: Synthetic Probe

<400> SEQUENCE: 508
taactgagta cccagaaacc                                                  20

<210> SEQ ID NO 509
<211> LENGTH: 20
<212> TYPE: DNA
<213> ORGANISM: Artificial Sequence
<220> FEATURE:
<223> OTHER INFORMATION: Synthetic Probe

<400> SEQUENCE: 509
cctgatcttg acctcaaata                                                  20

<210> SEQ ID NO 510
<211> LENGTH: 20
<212> TYPE: DNA
<213> ORGANISM: Artificial Sequence
<220> FEATURE:
<223> OTHER INFORMATION: Synthetic Probe

<400> SEQUENCE: 510
agggtgcaga aactacctaa                                                  20

<210> SEQ ID NO 511
<211> LENGTH: 20
<212> TYPE: DNA
<213> ORGANISM: Artificial Sequence
<220> FEATURE:
<223> OTHER INFORMATION: Synthetic Probe

<400> SEQUENCE: 511
tctcactctt ggataggaa                                                   20

<210> SEQ ID NO 512
<211> LENGTH: 20
<212> TYPE: DNA
<213> ORGANISM: Artificial Sequence
<220> FEATURE:
<223> OTHER INFORMATION: Synthetic Probe

<400> SEQUENCE: 512
actgtttaaa aaggggccac                                                  20
```

<210> SEQ ID NO 513
<211> LENGTH: 20
<212> TYPE: DNA
<213> ORGANISM: Artificial Sequence
<220> FEATURE:
<223> OTHER INFORMATION: Synthetic Probe

<400> SEQUENCE: 513
ttaccagaag cctgttcaaa                                           20

<210> SEQ ID NO 514
<211> LENGTH: 20
<212> TYPE: DNA
<213> ORGANISM: Artificial Sequence
<220> FEATURE:
<223> OTHER INFORMATION: Synthetic Probe

<400> SEQUENCE: 514
gtgggataaa tgtagagtgg                                           20

<210> SEQ ID NO 515
<211> LENGTH: 20
<212> TYPE: DNA
<213> ORGANISM: Artificial Sequence
<220> FEATURE:
<223> OTHER INFORMATION: Synthetic Probe

<400> SEQUENCE: 515
gattttgtgg ctgatgaatt                                           20

<210> SEQ ID NO 516
<211> LENGTH: 20
<212> TYPE: DNA
<213> ORGANISM: Artificial Sequence
<220> FEATURE:
<223> OTHER INFORMATION: Synthetic Probe

<400> SEQUENCE: 516
gacaaagggt cccttaagaa                                           20

<210> SEQ ID NO 517
<211> LENGTH: 20
<212> TYPE: DNA
<213> ORGANISM: Artificial Sequence
<220> FEATURE:
<223> OTHER INFORMATION: Synthetic Probe

<400> SEQUENCE: 517
acttctaaaa ctttgctcct                                           20

<210> SEQ ID NO 518
<211> LENGTH: 20
<212> TYPE: DNA
<213> ORGANISM: Artificial Sequence
<220> FEATURE:
<223> OTHER INFORMATION: Synthetic Probe

<400> SEQUENCE: 518
aatggaggac agagaaggga                                           20

<210> SEQ ID NO 519
<211> LENGTH: 20
<212> TYPE: DNA
<213> ORGANISM: Artificial Sequence
<220> FEATURE:
<223> OTHER INFORMATION: Synthetic Probe

<400> SEQUENCE: 519
gagaagagac tgtgatccga                                              20

<210> SEQ ID NO 520
<211> LENGTH: 20
<212> TYPE: DNA
<213> ORGANISM: Artificial Sequence
<220> FEATURE:
<223> OTHER INFORMATION: Synthetic Probe

<400> SEQUENCE: 520
gctgacaaac atcgagtcta                                              20

<210> SEQ ID NO 521
<211> LENGTH: 20
<212> TYPE: DNA
<213> ORGANISM: Artificial Sequence
<220> FEATURE:
<223> OTHER INFORMATION: Synthetic Probe

<400> SEQUENCE: 521
aacaaccaag cacgaagaat                                              20

<210> SEQ ID NO 522
<211> LENGTH: 20
<212> TYPE: DNA
<213> ORGANISM: Artificial Sequence
<220> FEATURE:
<223> OTHER INFORMATION: Synthetic Probe

<400> SEQUENCE: 522
ggtccaattg cctttacacc                                              20

<210> SEQ ID NO 523
<211> LENGTH: 20
<212> TYPE: DNA
<213> ORGANISM: Artificial Sequence
<220> FEATURE:
<223> OTHER INFORMATION: Synthetic Probe

<400> SEQUENCE: 523
ctgtcaatct aagccagtcc                                              20

<210> SEQ ID NO 524
<211> LENGTH: 20
<212> TYPE: DNA
<213> ORGANISM: Artificial Sequence
<220> FEATURE:
<223> OTHER INFORMATION: Synthetic Probe

<400> SEQUENCE: 524
cacttagagg gttgcctctg                                              20

<210> SEQ ID NO 525
<211> LENGTH: 20
<212> TYPE: DNA
<213> ORGANISM: Artificial Sequence
<220> FEATURE:
<223> OTHER INFORMATION: Synthetic Probe

<400> SEQUENCE: 525
gtgacgacag tggttctatc                                              20

<210> SEQ ID NO 526

```
<211> LENGTH: 20
<212> TYPE: DNA
<213> ORGANISM: Artificial Sequence
<220> FEATURE:
<223> OTHER INFORMATION: Synthetic Probe

<400> SEQUENCE: 526
tcacaatgtg cttccgaaat                                              20

<210> SEQ ID NO 527
<211> LENGTH: 20
<212> TYPE: DNA
<213> ORGANISM: Artificial Sequence
<220> FEATURE:
<223> OTHER INFORMATION: Synthetic Probe

<400> SEQUENCE: 527
cctcaactaa cggttggttt                                              20

<210> SEQ ID NO 528
<211> LENGTH: 20
<212> TYPE: DNA
<213> ORGANISM: Artificial Sequence
<220> FEATURE:
<223> OTHER INFORMATION: Synthetic Probe

<400> SEQUENCE: 528
gcctctttgt cacatcgaaa                                              20

<210> SEQ ID NO 529
<211> LENGTH: 20
<212> TYPE: DNA
<213> ORGANISM: Artificial Sequence
<220> FEATURE:
<223> OTHER INFORMATION: Synthetic Probe

<400> SEQUENCE: 529
agcccttcag caatgttatc                                              20

<210> SEQ ID NO 530
<211> LENGTH: 20
<212> TYPE: DNA
<213> ORGANISM: Artificial Sequence
<220> FEATURE:
<223> OTHER INFORMATION: Synthetic Probe

<400> SEQUENCE: 530
cagaatattt cgcctcaagg                                              20

<210> SEQ ID NO 531
<211> LENGTH: 20
<212> TYPE: DNA
<213> ORGANISM: Artificial Sequence
<220> FEATURE:
<223> OTHER INFORMATION: Synthetic Probe

<400> SEQUENCE: 531
tcccagggga attaccttag                                              20

<210> SEQ ID NO 532
<211> LENGTH: 20
<212> TYPE: DNA
<213> ORGANISM: Artificial Sequence
<220> FEATURE:
<223> OTHER INFORMATION: Synthetic Probe

<400> SEQUENCE: 532
```
gtcctaaagt aggaccgatg                                                    20

<210> SEQ ID NO 533
<211> LENGTH: 20
<212> TYPE: DNA
<213> ORGANISM: Artificial Sequence
<220> FEATURE:
<223> OTHER INFORMATION: Synthetic Probe

<400> SEQUENCE: 533
actcccaagg gaatttcttt                                                    20

<210> SEQ ID NO 534
<211> LENGTH: 20
<212> TYPE: DNA
<213> ORGANISM: Artificial Sequence
<220> FEATURE:
<223> OTHER INFORMATION: Synthetic Probe

<400> SEQUENCE: 534
ctacacgcgt gagacaagag                                                    20

<210> SEQ ID NO 535
<211> LENGTH: 20
<212> TYPE: DNA
<213> ORGANISM: Artificial Sequence
<220> FEATURE:
<223> OTHER INFORMATION: Synthetic Probe

<400> SEQUENCE: 535
acacagccgg aaaaagtaat                                                    20

<210> SEQ ID NO 536
<211> LENGTH: 20
<212> TYPE: DNA
<213> ORGANISM: Artificial Sequence
<220> FEATURE:
<223> OTHER INFORMATION: Synthetic Probe

<400> SEQUENCE: 536
cagctatagg agtcgcaaac                                                    20

<210> SEQ ID NO 537
<211> LENGTH: 20
<212> TYPE: DNA
<213> ORGANISM: Artificial Sequence
<220> FEATURE:
<223> OTHER INFORMATION: Synthetic Probe

<400> SEQUENCE: 537
gaaagaactc aatgtcgcct                                                    20

<210> SEQ ID NO 538
<211> LENGTH: 20
<212> TYPE: DNA
<213> ORGANISM: Artificial Sequence
<220> FEATURE:
<223> OTHER INFORMATION: Synthetic Probe

<400> SEQUENCE: 538
agcacgaaaa tggaaacact                                                    20

<210> SEQ ID NO 539
<211> LENGTH: 20
<212> TYPE: DNA

```
<213> ORGANISM: Artificial Sequence
<220> FEATURE:
<223> OTHER INFORMATION: Synthetic Probe

<400> SEQUENCE: 539
ttcctaagga agcacctgta                                                    20

<210> SEQ ID NO 540
<211> LENGTH: 20
<212> TYPE: DNA
<213> ORGANISM: Artificial Sequence
<220> FEATURE:
<223> OTHER INFORMATION: Synthetic Probe

<400> SEQUENCE: 540
ctaggttgca caaaaatgcc                                                    20

<210> SEQ ID NO 541
<211> LENGTH: 20
<212> TYPE: DNA
<213> ORGANISM: Artificial Sequence
<220> FEATURE:
<223> OTHER INFORMATION: Synthetic Probe

<400> SEQUENCE: 541
actcgatacc ctatctgtgc                                                    20

<210> SEQ ID NO 542
<211> LENGTH: 20
<212> TYPE: DNA
<213> ORGANISM: Artificial Sequence
<220> FEATURE:
<223> OTHER INFORMATION: Synthetic Probe

<400> SEQUENCE: 542
cggcaattca cctagaaact                                                    20

<210> SEQ ID NO 543
<211> LENGTH: 20
<212> TYPE: DNA
<213> ORGANISM: Artificial Sequence
<220> FEATURE:
<223> OTHER INFORMATION: Synthetic Probe

<400> SEQUENCE: 543
attttctagg tggttgcctg                                                    20

<210> SEQ ID NO 544
<211> LENGTH: 20
<212> TYPE: DNA
<213> ORGANISM: Artificial Sequence
<220> FEATURE:
<223> OTHER INFORMATION: Synthetic Probe

<400> SEQUENCE: 544
aatattgcca aaggacgacg                                                    20

<210> SEQ ID NO 545
<211> LENGTH: 20
<212> TYPE: DNA
<213> ORGANISM: Artificial Sequence
<220> FEATURE:
<223> OTHER INFORMATION: Synthetic Probe

<400> SEQUENCE: 545
aggcacaaag cagattgtta                                                    20
```

```
<210> SEQ ID NO 546
<211> LENGTH: 20
<212> TYPE: DNA
<213> ORGANISM: Artificial Sequence
<220> FEATURE:
<223> OTHER INFORMATION: Synthetic Probe

<400> SEQUENCE: 546
ataatgagga gagaccctcg                                               20

<210> SEQ ID NO 547
<211> LENGTH: 20
<212> TYPE: DNA
<213> ORGANISM: Artificial Sequence
<220> FEATURE:
<223> OTHER INFORMATION: Synthetic Probe

<400> SEQUENCE: 547
ttgcaggttt ctttagcact                                               20

<210> SEQ ID NO 548
<211> LENGTH: 20
<212> TYPE: DNA
<213> ORGANISM: Artificial Sequence
<220> FEATURE:
<223> OTHER INFORMATION: Synthetic Probe

<400> SEQUENCE: 548
gcactacatg aagatgtccc                                               20

<210> SEQ ID NO 549
<211> LENGTH: 20
<212> TYPE: DNA
<213> ORGANISM: Artificial Sequence
<220> FEATURE:
<223> OTHER INFORMATION: Synthetic Probe

<400> SEQUENCE: 549
actcatccag aaggtaggaa                                               20

<210> SEQ ID NO 550
<211> LENGTH: 20
<212> TYPE: DNA
<213> ORGANISM: Artificial Sequence
<220> FEATURE:
<223> OTHER INFORMATION: Synthetic Probe

<400> SEQUENCE: 550
gaggaaacag tctgcaagtc                                               20

<210> SEQ ID NO 551
<211> LENGTH: 20
<212> TYPE: DNA
<213> ORGANISM: Artificial Sequence
<220> FEATURE:
<223> OTHER INFORMATION: Synthetic Probe

<400> SEQUENCE: 551
cgaccgcaca aagaaggctg                                               20

<210> SEQ ID NO 552
<211> LENGTH: 20
<212> TYPE: DNA
<213> ORGANISM: Artificial Sequence
<220> FEATURE:
```

<223> OTHER INFORMATION: Synthetic Probe

<400> SEQUENCE: 552
atggaggcaa caatggttag                                           20

<210> SEQ ID NO 553
<211> LENGTH: 20
<212> TYPE: DNA
<213> ORGANISM: Artificial Sequence
<220> FEATURE:
<223> OTHER INFORMATION: Synthetic Probe

<400> SEQUENCE: 553
tgggagatgt agtccattac                                           20

<210> SEQ ID NO 554
<211> LENGTH: 20
<212> TYPE: DNA
<213> ORGANISM: Artificial Sequence
<220> FEATURE:
<223> OTHER INFORMATION: Synthetic Probe

<400> SEQUENCE: 554
tcaaatcaag gctcctcgcg                                           20

<210> SEQ ID NO 555
<211> LENGTH: 20
<212> TYPE: DNA
<213> ORGANISM: Artificial Sequence
<220> FEATURE:
<223> OTHER INFORMATION: Synthetic Probe

<400> SEQUENCE: 555
caagaccgaa ctcaatctcc                                           20

<210> SEQ ID NO 556
<211> LENGTH: 20
<212> TYPE: DNA
<213> ORGANISM: Artificial Sequence
<220> FEATURE:
<223> OTHER INFORMATION: Synthetic Probe

<400> SEQUENCE: 556
ctatttccag cggttaagag                                           20

<210> SEQ ID NO 557
<211> LENGTH: 20
<212> TYPE: DNA
<213> ORGANISM: Artificial Sequence
<220> FEATURE:
<223> OTHER INFORMATION: Synthetic Probe

<400> SEQUENCE: 557
taagaccacg cagcggtgtg                                           20

<210> SEQ ID NO 558
<211> LENGTH: 20
<212> TYPE: DNA
<213> ORGANISM: Artificial Sequence
<220> FEATURE:
<223> OTHER INFORMATION: Synthetic Probe

<400> SEQUENCE: 558
ctagctctta cagctatacg                                           20

```
<210> SEQ ID NO 559
<211> LENGTH: 20
<212> TYPE: DNA
<213> ORGANISM: Artificial Sequence
<220> FEATURE:
<223> OTHER INFORMATION: Synthetic Probe

<400> SEQUENCE: 559
tgacagcttg tatttatcac                                              20

<210> SEQ ID NO 560
<211> LENGTH: 20
<212> TYPE: DNA
<213> ORGANISM: Artificial Sequence
<220> FEATURE:
<223> OTHER INFORMATION: Synthetic Probe

<400> SEQUENCE: 560
aaacctacat ttcccaagag                                              20

<210> SEQ ID NO 561
<211> LENGTH: 20
<212> TYPE: DNA
<213> ORGANISM: Artificial Sequence
<220> FEATURE:
<223> OTHER INFORMATION: Synthetic Probe

<400> SEQUENCE: 561
cacacactcg gcacatagaa                                              20

<210> SEQ ID NO 562
<211> LENGTH: 20
<212> TYPE: DNA
<213> ORGANISM: Artificial Sequence
<220> FEATURE:
<223> OTHER INFORMATION: Synthetic Probe

<400> SEQUENCE: 562
gaagggagaa atggctcaga                                              20

<210> SEQ ID NO 563
<211> LENGTH: 20
<212> TYPE: DNA
<213> ORGANISM: Artificial Sequence
<220> FEATURE:
<223> OTHER INFORMATION: Synthetic Probe

<400> SEQUENCE: 563
atggatgcag cgggtacgta                                              20

<210> SEQ ID NO 564
<211> LENGTH: 20
<212> TYPE: DNA
<213> ORGANISM: Artificial Sequence
<220> FEATURE:
<223> OTHER INFORMATION: Synthetic Probe

<400> SEQUENCE: 564
aaatttgccc aaagggagca                                              20

<210> SEQ ID NO 565
<211> LENGTH: 20
<212> TYPE: DNA
<213> ORGANISM: Artificial Sequence
<220> FEATURE:
<223> OTHER INFORMATION: Synthetic Probe
```

```
<400> SEQUENCE: 565
gtgtgaaatg aggctctgaa                                               20

<210> SEQ ID NO 566
<211> LENGTH: 20
<212> TYPE: DNA
<213> ORGANISM: Artificial Sequence
<220> FEATURE:
<223> OTHER INFORMATION: Synthetic Probe

<400> SEQUENCE: 566
cagccagttg cagattaaaa                                               20

<210> SEQ ID NO 567
<211> LENGTH: 20
<212> TYPE: DNA
<213> ORGANISM: Artificial Sequence
<220> FEATURE:
<223> OTHER INFORMATION: Synthetic Probe

<400> SEQUENCE: 567
aacttgtgat ggtttcaagg                                               20

<210> SEQ ID NO 568
<211> LENGTH: 20
<212> TYPE: DNA
<213> ORGANISM: Artificial Sequence
<220> FEATURE:
<223> OTHER INFORMATION: Synthetic Probe

<400> SEQUENCE: 568
ttggtttatc aaatcctcgg                                               20

<210> SEQ ID NO 569
<211> LENGTH: 20
<212> TYPE: DNA
<213> ORGANISM: Artificial Sequence
<220> FEATURE:
<223> OTHER INFORMATION: Synthetic Probe

<400> SEQUENCE: 569
cgaaatgctt ccaacatggc                                               20

<210> SEQ ID NO 570
<211> LENGTH: 20
<212> TYPE: DNA
<213> ORGANISM: Artificial Sequence
<220> FEATURE:
<223> OTHER INFORMATION: Synthetic Probe

<400> SEQUENCE: 570
ctccaaaagc aacgactggt                                               20

<210> SEQ ID NO 571
<211> LENGTH: 20
<212> TYPE: DNA
<213> ORGANISM: Artificial Sequence
<220> FEATURE:
<223> OTHER INFORMATION: Synthetic Probe

<400> SEQUENCE: 571
caactcgtaa ccnctaaacc                                               20

<210> SEQ ID NO 572
<211> LENGTH: 20
```

```
<212> TYPE: DNA
<213> ORGANISM: Artificial Sequence
<220> FEATURE:
<223> OTHER INFORMATION: Synthetic Probe

<400> SEQUENCE: 572
gggtagaatt ggattctatt                                               20

<210> SEQ ID NO 573
<211> LENGTH: 20
<212> TYPE: DNA
<213> ORGANISM: Artificial Sequence
<220> FEATURE:
<223> OTHER INFORMATION: Synthetic Probe

<400> SEQUENCE: 573
tgagaatcac tgggcagaag                                               20

<210> SEQ ID NO 574
<211> LENGTH: 20
<212> TYPE: DNA
<213> ORGANISM: Artificial Sequence
<220> FEATURE:
<223> OTHER INFORMATION: Synthetic Probe

<400> SEQUENCE: 574
cttcctaaga gaagtatctt                                               20

<210> SEQ ID NO 575
<211> LENGTH: 20
<212> TYPE: DNA
<213> ORGANISM: Artificial Sequence
<220> FEATURE:
<223> OTHER INFORMATION: Synthetic Probe

<400> SEQUENCE: 575
cccataccat taagaaccga                                               20

<210> SEQ ID NO 576
<211> LENGTH: 20
<212> TYPE: DNA
<213> ORGANISM: Artificial Sequence
<220> FEATURE:
<223> OTHER INFORMATION: Synthetic Probe

<400> SEQUENCE: 576
ttagaaagac cagagactcc                                               20

<210> SEQ ID NO 577
<211> LENGTH: 20
<212> TYPE: DNA
<213> ORGANISM: Artificial Sequence
<220> FEATURE:
<223> OTHER INFORMATION: Synthetic Probe

<400> SEQUENCE: 577
caaattcctt gccctttaac                                               20

<210> SEQ ID NO 578
<211> LENGTH: 20
<212> TYPE: DNA
<213> ORGANISM: Artificial Sequence
<220> FEATURE:
<223> OTHER INFORMATION: Synthetic Probe

<400> SEQUENCE: 578
```
tccactcgac caaggaaaca                                         20

<210> SEQ ID NO 579
<211> LENGTH: 20
<212> TYPE: DNA
<213> ORGANISM: Artificial Sequence
<220> FEATURE:
<223> OTHER INFORMATION: Synthetic Probe

<400> SEQUENCE: 579
caagtcccaa atcttacgtt                                         20

<210> SEQ ID NO 580
<211> LENGTH: 20
<212> TYPE: DNA
<213> ORGANISM: Artificial Sequence
<220> FEATURE:
<223> OTHER INFORMATION: Synthetic Probe

<400> SEQUENCE: 580
atgcacagga aagactaggg                                         20

<210> SEQ ID NO 581
<211> LENGTH: 20
<212> TYPE: DNA
<213> ORGANISM: Artificial Sequence
<220> FEATURE:
<223> OTHER INFORMATION: Synthetic Probe

<400> SEQUENCE: 581
acccagtcag ataaaacagt                                         20

<210> SEQ ID NO 582
<211> LENGTH: 20
<212> TYPE: DNA
<213> ORGANISM: Artificial Sequence
<220> FEATURE:
<223> OTHER INFORMATION: Synthetic Probe

<400> SEQUENCE: 582
ccagaaatcg tggacacaca                                         20

<210> SEQ ID NO 583
<211> LENGTH: 20
<212> TYPE: DNA
<213> ORGANISM: Artificial Sequence
<220> FEATURE:
<223> OTHER INFORMATION: Synthetic Probe

<400> SEQUENCE: 583
ccaaaccaca actcgttagt                                         20

<210> SEQ ID NO 584
<211> LENGTH: 20
<212> TYPE: DNA
<213> ORGANISM: Artificial Sequence
<220> FEATURE:
<223> OTHER INFORMATION: Synthetic Probe

<400> SEQUENCE: 584
agactaagga cacgtacagg                                         20

<210> SEQ ID NO 585
<211> LENGTH: 20
<212> TYPE: DNA
<213> ORGANISM: Artificial Sequence
<220> FEATURE:
<223> OTHER INFORMATION: Synthetic Probe

<400> SEQUENCE: 585
gtttgcatct ccaaaagcaa                                               20

<210> SEQ ID NO 586
<211> LENGTH: 20
<212> TYPE: DNA
<213> ORGANISM: Artificial Sequence
<220> FEATURE:
<223> OTHER INFORMATION: Synthetic Probe

<400> SEQUENCE: 586
gcaacttcgt taagggaact                                               20

<210> SEQ ID NO 587
<211> LENGTH: 20
<212> TYPE: DNA
<213> ORGANISM: Artificial Sequence
<220> FEATURE:
<223> OTHER INFORMATION: Synthetic Probe

<400> SEQUENCE: 587
tactcagagt ctaattttgt                                               20

<210> SEQ ID NO 588
<211> LENGTH: 20
<212> TYPE: DNA
<213> ORGANISM: Artificial Sequence
<220> FEATURE:
<223> OTHER INFORMATION: Synthetic Probe

<400> SEQUENCE: 588
cttaacgttc tgatgaccag                                               20

<210> SEQ ID NO 589
<211> LENGTH: 20
<212> TYPE: DNA
<213> ORGANISM: Artificial Sequence
<220> FEATURE:
<223> OTHER INFORMATION: Synthetic Probe

<400> SEQUENCE: 589
caagaatgtt agctttcctg                                               20

<210> SEQ ID NO 590
<211> LENGTH: 20
<212> TYPE: DNA
<213> ORGANISM: Artificial Sequence
<220> FEATURE:
<223> OTHER INFORMATION: Synthetic Probe

<400> SEQUENCE: 590
tcacatacat atccttgtat                                               20

<210> SEQ ID NO 591
<211> LENGTH: 20
<212> TYPE: DNA
<213> ORGANISM: Artificial Sequence
<220> FEATURE:
<223> OTHER INFORMATION: Synthetic Probe

<400> SEQUENCE: 591
aagtgaaaca gtcagtaggt                                               20

<210> SEQ ID NO 592
<211> LENGTH: 20
<212> TYPE: DNA
<213> ORGANISM: Artificial Sequence
<220> FEATURE:
<223> OTHER INFORMATION: Synthetic Probe

<400> SEQUENCE: 592
aatggtgtac tcatttatct                                               20

<210> SEQ ID NO 593
<211> LENGTH: 20
<212> TYPE: DNA
<213> ORGANISM: Artificial Sequence
<220> FEATURE:
<223> OTHER INFORMATION: Synthetic Probe

<400> SEQUENCE: 593
ctgatcagca gacagtataa                                               20

<210> SEQ ID NO 594
<211> LENGTH: 20
<212> TYPE: DNA
<213> ORGANISM: Artificial Sequence
<220> FEATURE:
<223> OTHER INFORMATION: Synthetic Probe

<400> SEQUENCE: 594
aaatgagttg cttcaccatt                                               20

<210> SEQ ID NO 595
<211> LENGTH: 20
<212> TYPE: DNA
<213> ORGANISM: Artificial Sequence
<220> FEATURE:
<223> OTHER INFORMATION: Synthetic Probe

<400> SEQUENCE: 595
cttttaatct ccacatctag                                               20

<210> SEQ ID NO 596
<211> LENGTH: 20
<212> TYPE: DNA
<213> ORGANISM: Artificial Sequence
<220> FEATURE:
<223> OTHER INFORMATION: Synthetic Probe

<400> SEQUENCE: 596
tgttcctaca cttttaacac                                               20

<210> SEQ ID NO 597
<211> LENGTH: 20
<212> TYPE: DNA
<213> ORGANISM: Artificial Sequence
<220> FEATURE:
<223> OTHER INFORMATION: Synthetic Probe

<400> SEQUENCE: 597
tacactttta acaccttccg                                               20

<210> SEQ ID NO 598
<211> LENGTH: 20
<212> TYPE: DNA
<213> ORGANISM: Artificial Sequence
<220> FEATURE:
<223> OTHER INFORMATION: Synthetic Probe

```
<400> SEQUENCE: 598
cctatgctca tgagaataca                                              20

<210> SEQ ID NO 599
<211> LENGTH: 20
<212> TYPE: DNA
<213> ORGANISM: Artificial Sequence
<220> FEATURE:
<223> OTHER INFORMATION: Synthetic Probe

<400> SEQUENCE: 599
ctagccacag gaaagtaact                                              20

<210> SEQ ID NO 600
<211> LENGTH: 20
<212> TYPE: DNA
<213> ORGANISM: Artificial Sequence
<220> FEATURE:
<223> OTHER INFORMATION: Synthetic Probe

<400> SEQUENCE: 600
aacgcagcca caggactaaa                                              20

<210> SEQ ID NO 601
<211> LENGTH: 20
<212> TYPE: DNA
<213> ORGANISM: Artificial Sequence
<220> FEATURE:
<223> OTHER INFORMATION: Synthetic Probe

<400> SEQUENCE: 601
ttgcaaaacc tacagcttcc                                              20

<210> SEQ ID NO 602
<211> LENGTH: 20
<212> TYPE: DNA
<213> ORGANISM: Artificial Sequence
<220> FEATURE:
<223> OTHER INFORMATION: Synthetic Probe

<400> SEQUENCE: 602
aaccaatttg cttctttagt                                              20

<210> SEQ ID NO 603
<211> LENGTH: 20
<212> TYPE: DNA
<213> ORGANISM: Artificial Sequence
<220> FEATURE:
<223> OTHER INFORMATION: Synthetic Probe

<400> SEQUENCE: 603
ttccaactgt ccagtaggaa                                              20

<210> SEQ ID NO 604
<211> LENGTH: 20
<212> TYPE: DNA
<213> ORGANISM: Artificial Sequence
<220> FEATURE:
<223> OTHER INFORMATION: Synthetic Probe

<400> SEQUENCE: 604
ccagcttctg ggaaactcag                                              20

<210> SEQ ID NO 605
```

```
<211> LENGTH: 20
<212> TYPE: DNA
<213> ORGANISM: Artificial Sequence
<220> FEATURE:
<223> OTHER INFORMATION: Synthetic Probe

<400> SEQUENCE: 605
aaaaagctag tttgagcctc                                                     20

<210> SEQ ID NO 606
<211> LENGTH: 20
<212> TYPE: DNA
<213> ORGANISM: Artificial Sequence
<220> FEATURE:
<223> OTHER INFORMATION: Synthetic Probe

<400> SEQUENCE: 606
tgagatttag gactggagta                                                     20

<210> SEQ ID NO 607
<211> LENGTH: 20
<212> TYPE: DNA
<213> ORGANISM: Artificial Sequence
<220> FEATURE:
<223> OTHER INFORMATION: Synthetic Probe

<400> SEQUENCE: 607
ttggagatta gcaaccttca                                                     20

<210> SEQ ID NO 608
<211> LENGTH: 20
<212> TYPE: DNA
<213> ORGANISM: Artificial Sequence
<220> FEATURE:
<223> OTHER INFORMATION: Synthetic Probe

<400> SEQUENCE: 608
cttctgacaa ggagcctaaa                                                     20

<210> SEQ ID NO 609
<211> LENGTH: 20
<212> TYPE: DNA
<213> ORGANISM: Artificial Sequence
<220> FEATURE:
<223> OTHER INFORMATION: Synthetic Probe

<400> SEQUENCE: 609
ggaaaaccaa gagatctccc                                                     20

<210> SEQ ID NO 610
<211> LENGTH: 20
<212> TYPE: DNA
<213> ORGANISM: Artificial Sequence
<220> FEATURE:
<223> OTHER INFORMATION: Synthetic Probe

<400> SEQUENCE: 610
gatatcttct catagagatc                                                     20

<210> SEQ ID NO 611
<211> LENGTH: 20
<212> TYPE: DNA
<213> ORGANISM: Artificial Sequence
<220> FEATURE:
<223> OTHER INFORMATION: Synthetic Probe

<400> SEQUENCE: 611
```
agggacccac atctaataag                                           20

<210> SEQ ID NO 612
<211> LENGTH: 20
<212> TYPE: DNA
<213> ORGANISM: Artificial Sequence
<220> FEATURE:
<223> OTHER INFORMATION: Synthetic Probe

<400> SEQUENCE: 612
gaacagtgac ctagacattt                                           20

<210> SEQ ID NO 613
<211> LENGTH: 20
<212> TYPE: DNA
<213> ORGANISM: Artificial Sequence
<220> FEATURE:
<223> OTHER INFORMATION: Synthetic Probe

<400> SEQUENCE: 613
tgtgagcaaa cttccttctt                                           20

<210> SEQ ID NO 614
<211> LENGTH: 20
<212> TYPE: DNA
<213> ORGANISM: Artificial Sequence
<220> FEATURE:
<223> OTHER INFORMATION: Synthetic Probe

<400> SEQUENCE: 614
aaaacgcttg tcttccacag                                           20

<210> SEQ ID NO 615
<211> LENGTH: 20
<212> TYPE: DNA
<213> ORGANISM: Artificial Sequence
<220> FEATURE:
<223> OTHER INFORMATION: Synthetic Probe

<400> SEQUENCE: 615
tcattatgga tgttaagctc                                           20

<210> SEQ ID NO 616
<211> LENGTH: 20
<212> TYPE: DNA
<213> ORGANISM: Artificial Sequence
<220> FEATURE:
<223> OTHER INFORMATION: Synthetic Probe

<400> SEQUENCE: 616
cttatcccaa aagacttcca                                           20

<210> SEQ ID NO 617
<211> LENGTH: 20
<212> TYPE: DNA
<213> ORGANISM: Artificial Sequence
<220> FEATURE:
<223> OTHER INFORMATION: Synthetic Probe

<400> SEQUENCE: 617
aaatgccaca ttgtagccaa                                           20

<210> SEQ ID NO 618
<211> LENGTH: 20
<212> TYPE: DNA

```
<213> ORGANISM: Artificial Sequence
<220> FEATURE:
<223> OTHER INFORMATION: Synthetic Probe

<400> SEQUENCE: 618
gtgaaatcaa agtagcccgc                                                    20

<210> SEQ ID NO 619
<211> LENGTH: 20
<212> TYPE: DNA
<213> ORGANISM: Artificial Sequence
<220> FEATURE:
<223> OTHER INFORMATION: Synthetic Probe

<400> SEQUENCE: 619
cgccaatccc caaaacgacg                                                    20

<210> SEQ ID NO 620
<211> LENGTH: 20
<212> TYPE: DNA
<213> ORGANISM: Artificial Sequence
<220> FEATURE:
<223> OTHER INFORMATION: Synthetic Probe

<400> SEQUENCE: 620
atacttaagt agctacacca                                                    20

<210> SEQ ID NO 621
<211> LENGTH: 20
<212> TYPE: DNA
<213> ORGANISM: Artificial Sequence
<220> FEATURE:
<223> OTHER INFORMATION: Synthetic Probe

<400> SEQUENCE: 621
caaagaaacc tttccagggc                                                    20

<210> SEQ ID NO 622
<211> LENGTH: 20
<212> TYPE: DNA
<213> ORGANISM: Artificial Sequence
<220> FEATURE:
<223> OTHER INFORMATION: Synthetic Probe

<400> SEQUENCE: 622
gaacacaact tgcctagatc                                                    20

<210> SEQ ID NO 623
<211> LENGTH: 20
<212> TYPE: DNA
<213> ORGANISM: Artificial Sequence
<220> FEATURE:
<223> OTHER INFORMATION: Synthetic Probe

<400> SEQUENCE: 623
aaaatccaga cagacttcct                                                    20

<210> SEQ ID NO 624
<211> LENGTH: 20
<212> TYPE: DNA
<213> ORGANISM: Artificial Sequence
<220> FEATURE:
<223> OTHER INFORMATION: Synthetic Probe

<400> SEQUENCE: 624
ttacacatgc tttgtaagcg                                                    20
```

```
<210> SEQ ID NO 625
<211> LENGTH: 20
<212> TYPE: DNA
<213> ORGANISM: Artificial Sequence
<220> FEATURE:
<223> OTHER INFORMATION: Synthetic Probe

<400> SEQUENCE: 625
gattaggcag agtagtcaaa                                               20

<210> SEQ ID NO 626
<211> LENGTH: 20
<212> TYPE: DNA
<213> ORGANISM: Artificial Sequence
<220> FEATURE:
<223> OTHER INFORMATION: Synthetic Probe

<400> SEQUENCE: 626
ttctcttcta atgtatagga                                               20

<210> SEQ ID NO 627
<211> LENGTH: 20
<212> TYPE: DNA
<213> ORGANISM: Artificial Sequence
<220> FEATURE:
<223> OTHER INFORMATION: Synthetic Probe

<400> SEQUENCE: 627
ccagttacaa gaccttgtaa                                               20

<210> SEQ ID NO 628
<211> LENGTH: 20
<212> TYPE: DNA
<213> ORGANISM: Artificial Sequence
<220> FEATURE:
<223> OTHER INFORMATION: Synthetic Probe

<400> SEQUENCE: 628
tgaacgaaga ccagcaaggc                                               20

<210> SEQ ID NO 629
<211> LENGTH: 20
<212> TYPE: DNA
<213> ORGANISM: Artificial Sequence
<220> FEATURE:
<223> OTHER INFORMATION: Synthetic Probe

<400> SEQUENCE: 629
ctatgagtat tttatgctca                                               20

<210> SEQ ID NO 630
<211> LENGTH: 20
<212> TYPE: DNA
<213> ORGANISM: Artificial Sequence
<220> FEATURE:
<223> OTHER INFORMATION: Synthetic Probe

<400> SEQUENCE: 630
gggagacaag ggcaaaagga                                               20

<210> SEQ ID NO 631
<211> LENGTH: 20
<212> TYPE: DNA
<213> ORGANISM: Artificial Sequence
<220> FEATURE:
```

<223> OTHER INFORMATION: Synthetic Probe

<400> SEQUENCE: 631
agtgacaggt ccagataaag                                           20

<210> SEQ ID NO 632
<211> LENGTH: 20
<212> TYPE: DNA
<213> ORGANISM: Artificial Sequence
<220> FEATURE:
<223> OTHER INFORMATION: Synthetic Probe

<400> SEQUENCE: 632
atcgaacccg acttttcata                                           20

<210> SEQ ID NO 633
<211> LENGTH: 20
<212> TYPE: DNA
<213> ORGANISM: Artificial Sequence
<220> FEATURE:
<223> OTHER INFORMATION: Synthetic Probe

<400> SEQUENCE: 633
tactgtgtac ccaacgaaca                                           20

<210> SEQ ID NO 634
<211> LENGTH: 20
<212> TYPE: DNA
<213> ORGANISM: Artificial Sequence
<220> FEATURE:
<223> OTHER INFORMATION: Synthetic Probe

<400> SEQUENCE: 634
tcagactgtg ttgacaatta                                           20

<210> SEQ ID NO 635
<211> LENGTH: 20
<212> TYPE: DNA
<213> ORGANISM: Artificial Sequence
<220> FEATURE:
<223> OTHER INFORMATION: Synthetic Probe

<400> SEQUENCE: 635
ctttctgagc aacttaagtt                                           20

<210> SEQ ID NO 636
<211> LENGTH: 20
<212> TYPE: DNA
<213> ORGANISM: Artificial Sequence
<220> FEATURE:
<223> OTHER INFORMATION: Synthetic Probe

<400> SEQUENCE: 636
catcagtcaa tccaacaacc                                           20

<210> SEQ ID NO 637
<211> LENGTH: 20
<212> TYPE: DNA
<213> ORGANISM: Artificial Sequence
<220> FEATURE:
<223> OTHER INFORMATION: Synthetic Probe

<400> SEQUENCE: 637
cgaatcctta ttcagaacct                                           20

```
<210> SEQ ID NO 638
<211> LENGTH: 20
<212> TYPE: DNA
<213> ORGANISM: Artificial Sequence
<220> FEATURE:
<223> OTHER INFORMATION: Synthetic Probe

<400> SEQUENCE: 638
atcaaaactg gttcccatac                                               20

<210> SEQ ID NO 639
<211> LENGTH: 20
<212> TYPE: DNA
<213> ORGANISM: Artificial Sequence
<220> FEATURE:
<223> OTHER INFORMATION: Synthetic Probe

<400> SEQUENCE: 639
gcacacagaa ccctgaaaca                                               20

<210> SEQ ID NO 640
<211> LENGTH: 20
<212> TYPE: DNA
<213> ORGANISM: Artificial Sequence
<220> FEATURE:
<223> OTHER INFORMATION: Synthetic Probe

<400> SEQUENCE: 640
tgatccctct gtaaaaggg                                                20

<210> SEQ ID NO 641
<211> LENGTH: 20
<212> TYPE: DNA
<213> ORGANISM: Artificial Sequence
<220> FEATURE:
<223> OTHER INFORMATION: Synthetic Probe

<400> SEQUENCE: 641
ctagaatgga ggatctgcaa                                               20

<210> SEQ ID NO 642
<211> LENGTH: 20
<212> TYPE: DNA
<213> ORGANISM: Artificial Sequence
<220> FEATURE:
<223> OTHER INFORMATION: Synthetic Probe

<400> SEQUENCE: 642
aacagaacca gagacccgag                                               20

<210> SEQ ID NO 643
<211> LENGTH: 20
<212> TYPE: DNA
<213> ORGANISM: Artificial Sequence
<220> FEATURE:
<223> OTHER INFORMATION: Synthetic Probe

<400> SEQUENCE: 643
acacatgatg atctggacta                                               20

<210> SEQ ID NO 644
<211> LENGTH: 20
<212> TYPE: DNA
<213> ORGANISM: Artificial Sequence
<220> FEATURE:
<223> OTHER INFORMATION: Synthetic Probe
```

```
<400> SEQUENCE: 644
acgggaagac agtgagaagc                                              20

<210> SEQ ID NO 645
<211> LENGTH: 20
<212> TYPE: DNA
<213> ORGANISM: Artificial Sequence
<220> FEATURE:
<223> OTHER INFORMATION: Synthetic Probe

<400> SEQUENCE: 645
cgcgactggc tgagacaaac                                              20

<210> SEQ ID NO 646
<211> LENGTH: 20
<212> TYPE: DNA
<213> ORGANISM: Artificial Sequence
<220> FEATURE:
<223> OTHER INFORMATION: Synthetic Probe

<400> SEQUENCE: 646
agcagagcct ttgacataaa                                              20

<210> SEQ ID NO 647
<211> LENGTH: 20
<212> TYPE: DNA
<213> ORGANISM: Artificial Sequence
<220> FEATURE:
<223> OTHER INFORMATION: Synthetic Probe

<400> SEQUENCE: 647
catcgtgaat aagggacccg                                              20

<210> SEQ ID NO 648
<211> LENGTH: 20
<212> TYPE: DNA
<213> ORGANISM: Artificial Sequence
<220> FEATURE:
<223> OTHER INFORMATION: Synthetic Probe

<400> SEQUENCE: 648
ggcccaaacc agacaaaact                                              20

<210> SEQ ID NO 649
<211> LENGTH: 20
<212> TYPE: DNA
<213> ORGANISM: Artificial Sequence
<220> FEATURE:
<223> OTHER INFORMATION: Synthetic Probe

<400> SEQUENCE: 649
ttcctgcctg acagtaaaaa                                              20

<210> SEQ ID NO 650
<211> LENGTH: 20
<212> TYPE: DNA
<213> ORGANISM: Artificial Sequence
<220> FEATURE:
<223> OTHER INFORMATION: Synthetic Probe

<400> SEQUENCE: 650
aacaaccacc gaggaagttc                                              20

<210> SEQ ID NO 651
<211> LENGTH: 20
```

```
<212> TYPE: DNA
<213> ORGANISM: Artificial Sequence
<220> FEATURE:
<223> OTHER INFORMATION: Synthetic Probe

<400> SEQUENCE: 651
gacttgcttt gagaatttca                                              20

<210> SEQ ID NO 652
<211> LENGTH: 20
<212> TYPE: DNA
<213> ORGANISM: Artificial Sequence
<220> FEATURE:
<223> OTHER INFORMATION: Synthetic Probe

<400> SEQUENCE: 652
tgacagcaca atgtatggag                                              20

<210> SEQ ID NO 653
<211> LENGTH: 20
<212> TYPE: DNA
<213> ORGANISM: Artificial Sequence
<220> FEATURE:
<223> OTHER INFORMATION: Synthetic Probe

<400> SEQUENCE: 653
aatccccaaa aaggcctgca                                              20

<210> SEQ ID NO 654
<211> LENGTH: 20
<212> TYPE: DNA
<213> ORGANISM: Artificial Sequence
<220> FEATURE:
<223> OTHER INFORMATION: Synthetic Probe

<400> SEQUENCE: 654
ccgactcaca cgaacattca                                              20

<210> SEQ ID NO 655
<211> LENGTH: 20
<212> TYPE: DNA
<213> ORGANISM: Artificial Sequence
<220> FEATURE:
<223> OTHER INFORMATION: Synthetic Probe

<400> SEQUENCE: 655
gaacacatgt gaagctggac                                              20

<210> SEQ ID NO 656
<211> LENGTH: 20
<212> TYPE: DNA
<213> ORGANISM: Artificial Sequence
<220> FEATURE:
<223> OTHER INFORMATION: Synthetic Probe

<400> SEQUENCE: 656
ttgctgccac tgagtaaaag                                              20

<210> SEQ ID NO 657
<211> LENGTH: 20
<212> TYPE: DNA
<213> ORGANISM: Artificial Sequence
<220> FEATURE:
<223> OTHER INFORMATION: Synthetic Probe

<400> SEQUENCE: 657
```
catgtattcg gcaatccaag                                          20

<210> SEQ ID NO 658
<211> LENGTH: 20
<212> TYPE: DNA
<213> ORGANISM: Artificial Sequence
<220> FEATURE:
<223> OTHER INFORMATION: Synthetic Probe

<400> SEQUENCE: 658
caatgggtat gaacagcttc                                          20

<210> SEQ ID NO 659
<211> LENGTH: 20
<212> TYPE: DNA
<213> ORGANISM: Artificial Sequence
<220> FEATURE:
<223> OTHER INFORMATION: Synthetic Probe

<400> SEQUENCE: 659
ctgtccacca tgaaaacact                                          20

<210> SEQ ID NO 660
<211> LENGTH: 20
<212> TYPE: DNA
<213> ORGANISM: Artificial Sequence
<220> FEATURE:
<223> OTHER INFORMATION: Synthetic Probe

<400> SEQUENCE: 660
gacagtctca cattgagaag                                          20

<210> SEQ ID NO 661
<211> LENGTH: 20
<212> TYPE: DNA
<213> ORGANISM: Artificial Sequence
<220> FEATURE:
<223> OTHER INFORMATION: Synthetic Probe

<400> SEQUENCE: 661
catattgcaa ccagtagtgg                                          20

<210> SEQ ID NO 662
<211> LENGTH: 20
<212> TYPE: DNA
<213> ORGANISM: Artificial Sequence
<220> FEATURE:
<223> OTHER INFORMATION: Synthetic Probe

<400> SEQUENCE: 662
aggctgaaag caagaatcca                                          20

<210> SEQ ID NO 663
<211> LENGTH: 20
<212> TYPE: DNA
<213> ORGANISM: Artificial Sequence
<220> FEATURE:
<223> OTHER INFORMATION: Synthetic Probe

<400> SEQUENCE: 663
aggaaagaag ctgggttcag                                          20

<210> SEQ ID NO 664
<211> LENGTH: 20
<212> TYPE: DNA
<213> ORGANISM: Artificial Sequence

```
<220> FEATURE:
<223> OTHER INFORMATION: Synthetic Probe

<400> SEQUENCE: 664
agaggtcaca tcagggttta                                        20

<210> SEQ ID NO 665
<211> LENGTH: 20
<212> TYPE: DNA
<213> ORGANISM: Artificial Sequence
<220> FEATURE:
<223> OTHER INFORMATION: Synthetic Probe

<400> SEQUENCE: 665
gaaatgagaa tcggctcccg                                        20

<210> SEQ ID NO 666
<211> LENGTH: 20
<212> TYPE: DNA
<213> ORGANISM: Artificial Sequence
<220> FEATURE:
<223> OTHER INFORMATION: Synthetic Probe

<400> SEQUENCE: 666
aaagggaacc atcagaaccc                                        20

<210> SEQ ID NO 667
<211> LENGTH: 20
<212> TYPE: DNA
<213> ORGANISM: Artificial Sequence
<220> FEATURE:
<223> OTHER INFORMATION: Synthetic Probe

<400> SEQUENCE: 667
cggggccaga atacagatcg                                        20

<210> SEQ ID NO 668
<211> LENGTH: 20
<212> TYPE: DNA
<213> ORGANISM: Artificial Sequence
<220> FEATURE:
<223> OTHER INFORMATION: Synthetic Probe

<400> SEQUENCE: 668
agcagatatg aattcagaga                                        20

<210> SEQ ID NO 669
<211> LENGTH: 20
<212> TYPE: DNA
<213> ORGANISM: Artificial Sequence
<220> FEATURE:
<223> OTHER INFORMATION: Synthetic Probe

<400> SEQUENCE: 669
tggaggaaga agtaagggcg                                        20

<210> SEQ ID NO 670
<211> LENGTH: 20
<212> TYPE: DNA
<213> ORGANISM: Artificial Sequence
<220> FEATURE:
<223> OTHER INFORMATION: Synthetic Probe

<400> SEQUENCE: 670
caccaaccaa aggtctatca                                        20
```

```
<210> SEQ ID NO 671
<211> LENGTH: 20
<212> TYPE: DNA
<213> ORGANISM: Artificial Sequence
<220> FEATURE:
<223> OTHER INFORMATION: Synthetic Probe

<400> SEQUENCE: 671
tcaccctggg cttaacgaag                                              20

<210> SEQ ID NO 672
<211> LENGTH: 20
<212> TYPE: DNA
<213> ORGANISM: Artificial Sequence
<220> FEATURE:
<223> OTHER INFORMATION: Synthetic Probe

<400> SEQUENCE: 672
cagcaattgg caaactcccg                                              20

<210> SEQ ID NO 673
<211> LENGTH: 20
<212> TYPE: DNA
<213> ORGANISM: Artificial Sequence
<220> FEATURE:
<223> OTHER INFORMATION: Synthetic Probe

<400> SEQUENCE: 673
aacatgagat gttgacaggc                                              20

<210> SEQ ID NO 674
<211> LENGTH: 20
<212> TYPE: DNA
<213> ORGANISM: Artificial Sequence
<220> FEATURE:
<223> OTHER INFORMATION: Synthetic Probe

<400> SEQUENCE: 674
gaagccggga agaaaggagg                                              20

<210> SEQ ID NO 675
<211> LENGTH: 20
<212> TYPE: DNA
<213> ORGANISM: Artificial Sequence
<220> FEATURE:
<223> OTHER INFORMATION: Synthetic Probe

<400> SEQUENCE: 675
gtcaaaccct agacaatgga                                              20

<210> SEQ ID NO 676
<211> LENGTH: 20
<212> TYPE: DNA
<213> ORGANISM: Artificial Sequence
<220> FEATURE:
<223> OTHER INFORMATION: Synthetic Probe

<400> SEQUENCE: 676
gccgcgaaag aggcgagaaa                                              20

<210> SEQ ID NO 677
<211> LENGTH: 20
<212> TYPE: DNA
<213> ORGANISM: Artificial Sequence
<220> FEATURE:
<223> OTHER INFORMATION: Synthetic Probe
```

<400> SEQUENCE: 677
aggaatcagc tggagaaagg                                              20

<210> SEQ ID NO 678
<211> LENGTH: 20
<212> TYPE: DNA
<213> ORGANISM: Artificial Sequence
<220> FEATURE:
<223> OTHER INFORMATION: Synthetic Probe

<400> SEQUENCE: 678
ctcccataac tgcacagaaa                                              20

<210> SEQ ID NO 679
<211> LENGTH: 20
<212> TYPE: DNA
<213> ORGANISM: Artificial Sequence
<220> FEATURE:
<223> OTHER INFORMATION: Synthetic Probe

<400> SEQUENCE: 679
tttattctat aagacccagc                                              20

<210> SEQ ID NO 680
<211> LENGTH: 20
<212> TYPE: DNA
<213> ORGANISM: Artificial Sequence
<220> FEATURE:
<223> OTHER INFORMATION: Synthetic Probe

<400> SEQUENCE: 680
tcatcataca actttcttgc                                              20

<210> SEQ ID NO 681
<211> LENGTH: 20
<212> TYPE: DNA
<213> ORGANISM: Artificial Sequence
<220> FEATURE:
<223> OTHER INFORMATION: Synthetic Probe

<400> SEQUENCE: 681
taagtgtgag aaagaggcca                                              20

<210> SEQ ID NO 682
<211> LENGTH: 20
<212> TYPE: DNA
<213> ORGANISM: Artificial Sequence
<220> FEATURE:
<223> OTHER INFORMATION: Synthetic Probe

<400> SEQUENCE: 682
ccattttgaa gccgagttaa                                              20

<210> SEQ ID NO 683
<211> LENGTH: 20
<212> TYPE: DNA
<213> ORGANISM: Artificial Sequence
<220> FEATURE:
<223> OTHER INFORMATION: Synthetic Probe

<400> SEQUENCE: 683
tccaaaaaca tcttctctcc                                              20

<210> SEQ ID NO 684

```
<211> LENGTH: 20
<212> TYPE: DNA
<213> ORGANISM: Artificial Sequence
<220> FEATURE:
<223> OTHER INFORMATION: Synthetic Probe

<400> SEQUENCE: 684
atcctttgct ttttcaagaa                                               20

<210> SEQ ID NO 685
<211> LENGTH: 20
<212> TYPE: DNA
<213> ORGANISM: Artificial Sequence
<220> FEATURE:
<223> OTHER INFORMATION: Synthetic Probe

<400> SEQUENCE: 685
gaaaccagct gtcgggaaac                                               20

<210> SEQ ID NO 686
<211> LENGTH: 20
<212> TYPE: DNA
<213> ORGANISM: Artificial Sequence
<220> FEATURE:
<223> OTHER INFORMATION: Synthetic Probe

<400> SEQUENCE: 686
agatgtcagt taatcacaca                                               20

<210> SEQ ID NO 687
<211> LENGTH: 20
<212> TYPE: DNA
<213> ORGANISM: Artificial Sequence
<220> FEATURE:
<223> OTHER INFORMATION: Synthetic Probe

<400> SEQUENCE: 687
gctagataca tgtggcaaag                                               20

<210> SEQ ID NO 688
<211> LENGTH: 20
<212> TYPE: DNA
<213> ORGANISM: Artificial Sequence
<220> FEATURE:
<223> OTHER INFORMATION: Synthetic Probe

<400> SEQUENCE: 688
ggatttccct tataaggtaa                                               20

<210> SEQ ID NO 689
<211> LENGTH: 20
<212> TYPE: DNA
<213> ORGANISM: Artificial Sequence
<220> FEATURE:
<223> OTHER INFORMATION: Synthetic Probe

<400> SEQUENCE: 689
caatcaaagc cttccacacg                                               20

<210> SEQ ID NO 690
<211> LENGTH: 28
<212> TYPE: DNA
<213> ORGANISM: Artificial Sequence
<220> FEATURE:
<223> OTHER INFORMATION: Synthetic Probe

<400> SEQUENCE: 690
```

```
tttcactgta gctagaccaa aatcacct                                              28

<210> SEQ ID NO 691
<211> LENGTH: 28
<212> TYPE: DNA
<213> ORGANISM: Artificial Sequence
<220> FEATURE:
<223> OTHER INFORMATION: Synthetic Probe

<400> SEQUENCE: 691
tttctctgta gctagaccaa aatcacct                                              28

<210> SEQ ID NO 692
<211> LENGTH: 17
<212> TYPE: DNA
<213> ORGANISM: Artificial Sequence
<220> FEATURE:
<223> OTHER INFORMATION: Synthetic Probe

<400> SEQUENCE: 692
aggtgatttt ggtctag                                                          17

<210> SEQ ID NO 693
<211> LENGTH: 26
<212> TYPE: DNA
<213> ORGANISM: Artificial Sequence
<220> FEATURE:
<223> OTHER INFORMATION: Synthetic Probe

<400> SEQUENCE: 693
ggcgtgtaag taatccatgc cctgtg                                                26

<210> SEQ ID NO 694
<211> LENGTH: 26
<212> TYPE: DNA
<213> ORGANISM: Artificial Sequence
<220> FEATURE:
<223> OTHER INFORMATION: Synthetic Probe

<400> SEQUENCE: 694
ggcgagtaag taatccatgc cctgtg                                                26

<210> SEQ ID NO 695
<211> LENGTH: 17
<212> TYPE: DNA
<213> ORGANISM: Artificial Sequence
<220> FEATURE:
<223> OTHER INFORMATION: Synthetic Probe

<400> SEQUENCE: 695
cacagggcat ggattac                                                          17

<210> SEQ ID NO 696
<211> LENGTH: 24
<212> TYPE: DNA
<213> ORGANISM: Artificial Sequence
<220> FEATURE:
<223> OTHER INFORMATION: Synthetic Probe

<400> SEQUENCE: 696
cttggttccc gttttctaga cgtc                                                  24

<210> SEQ ID NO 697
<211> LENGTH: 24
<212> TYPE: DNA
```

```
<213> ORGANISM: Artificial Sequence
<220> FEATURE:
<223> OTHER INFORMATION: Synthetic Probe

<400> SEQUENCE: 697
cttcgttccc gttttctaga cgtc                                          24

<210> SEQ ID NO 698
<211> LENGTH: 15
<212> TYPE: DNA
<213> ORGANISM: Artificial Sequence
<220> FEATURE:
<223> OTHER INFORMATION: Synthetic Probe

<400> SEQUENCE: 698
gacgtctaga aaacg                                                    15

<210> SEQ ID NO 699
<211> LENGTH: 25
<212> TYPE: DNA
<213> ORGANISM: Artificial Sequence
<220> FEATURE:
<223> OTHER INFORMATION: Synthetic Probe

<400> SEQUENCE: 699
cattttgttc agtttctgtg ttgga                                         25

<210> SEQ ID NO 700
<211> LENGTH: 25
<212> TYPE: DNA
<213> ORGANISM: Artificial Sequence
<220> FEATURE:
<223> OTHER INFORMATION: Synthetic Probe

<400> SEQUENCE: 700
cattctgttc agtttctgtg ttgga                                         25

<210> SEQ ID NO 701
<211> LENGTH: 19
<212> TYPE: DNA
<213> ORGANISM: Artificial Sequence
<220> FEATURE:
<223> OTHER INFORMATION: Synthetic Probe

<400> SEQUENCE: 701
tccaacacag aaactgaac                                                19

<210> SEQ ID NO 702
<211> LENGTH: 25
<212> TYPE: DNA
<213> ORGANISM: Artificial Sequence
<220> FEATURE:
<223> OTHER INFORMATION: Synthetic Probe

<400> SEQUENCE: 702
gagacgggtc atcatcatag attgg                                         25

<210> SEQ ID NO 703
<211> LENGTH: 25
<212> TYPE: DNA
<213> ORGANISM: Artificial Sequence
<220> FEATURE:
<223> OTHER INFORMATION: Synthetic Probe

<400> SEQUENCE: 703
gagatgggtc atcatcatag attgg                                         25
```

<210> SEQ ID NO 704
<211> LENGTH: 19
<212> TYPE: DNA
<213> ORGANISM: Artificial Sequence
<220> FEATURE:
<223> OTHER INFORMATION: Synthetic Probe

<400> SEQUENCE: 704
ccaatctatg atgatgacc                                                  19

<210> SEQ ID NO 705
<211> LENGTH: 31
<212> TYPE: DNA
<213> ORGANISM: Artificial Sequence
<220> FEATURE:
<223> OTHER INFORMATION: Synthetic Probe

<400> SEQUENCE: 705
atctctattg gatattctat tcatgaaaca c                                    31

<210> SEQ ID NO 706
<211> LENGTH: 31
<212> TYPE: DNA
<213> ORGANISM: Artificial Sequence
<220> FEATURE:
<223> OTHER INFORMATION: Synthetic Probe

<400> SEQUENCE: 706
atctgtattg gatattctat tcatgaaaca c                                    31

<210> SEQ ID NO 707
<211> LENGTH: 25
<212> TYPE: DNA
<213> ORGANISM: Artificial Sequence
<220> FEATURE:
<223> OTHER INFORMATION: Synthetic Probe

<400> SEQUENCE: 707
gtgtttcatg aatagaatat ccaat                                           25

<210> SEQ ID NO 708
<211> LENGTH: 25
<212> TYPE: DNA
<213> ORGANISM: Artificial Sequence
<220> FEATURE:
<223> OTHER INFORMATION: Synthetic Probe

<400> SEQUENCE: 708
ctgtataaat gaatctgcct ggtgt                                           25

<210> SEQ ID NO 709
<211> LENGTH: 25
<212> TYPE: DNA
<213> ORGANISM: Artificial Sequence
<220> FEATURE:
<223> OTHER INFORMATION: Synthetic Probe

<400> SEQUENCE: 709
ctgtgtaaat gaatctgcct ggtgt                                           25

<210> SEQ ID NO 710
<211> LENGTH: 19
<212> TYPE: DNA
<213> ORGANISM: Artificial Sequence
<220> FEATURE:

<223> OTHER INFORMATION: Synthetic Probe

<400> SEQUENCE: 710
acaccaggca gattcattt                                                    19

<210> SEQ ID NO 711
<211> LENGTH: 19
<212> TYPE: DNA
<213> ORGANISM: Artificial Sequence
<220> FEATURE:
<223> OTHER INFORMATION: Synthetic Probe

<400> SEQUENCE: 711
ggagggcagg aggcggccg                                                    19

<210> SEQ ID NO 712
<211> LENGTH: 18
<212> TYPE: DNA
<213> ORGANISM: Artificial Sequence
<220> FEATURE:
<223> OTHER INFORMATION: Synthetic Probe

<400> SEQUENCE: 712
tcccggggcc aggagagc                                                     18

<210> SEQ ID NO 713
<211> LENGTH: 24
<212> TYPE: DNA
<213> ORGANISM: Artificial Sequence
<220> FEATURE:
<223> OTHER INFORMATION: Synthetic Probe

<400> SEQUENCE: 713
aggaaacaac gttagcctgg tggc                                              24

<210> SEQ ID NO 714
<211> LENGTH: 23
<212> TYPE: DNA
<213> ORGANISM: Artificial Sequence
<220> FEATURE:
<223> OTHER INFORMATION: Synthetic Probe

<400> SEQUENCE: 714
ccaccgaacg gcacgattcc agc                                               23

<210> SEQ ID NO 715
<211> LENGTH: 23
<212> TYPE: DNA
<213> ORGANISM: Artificial Sequence
<220> FEATURE:
<223> OTHER INFORMATION: Synthetic Probe

<400> SEQUENCE: 715
cacccacccc aggaaataac ggg                                               23

<210> SEQ ID NO 716
<211> LENGTH: 21
<212> TYPE: DNA
<213> ORGANISM: Artificial Sequence
<220> FEATURE:
<223> OTHER INFORMATION: Synthetic Probe

<400> SEQUENCE: 716
cccatgttgg ccaagaggtc t                                                 21

```
<210> SEQ ID NO 717
<211> LENGTH: 22
<212> TYPE: DNA
<213> ORGANISM: Artificial Sequence
<220> FEATURE:
<223> OTHER INFORMATION: Synthetic Probe

<400> SEQUENCE: 717
gacactcccc gtgaacacgt gg                                              22

<210> SEQ ID NO 718
<211> LENGTH: 23
<212> TYPE: DNA
<213> ORGANISM: Artificial Sequence
<220> FEATURE:
<223> OTHER INFORMATION: Synthetic Probe

<400> SEQUENCE: 718
acctcgctga caccttgctg aca                                             23

<210> SEQ ID NO 719
<211> LENGTH: 24
<212> TYPE: DNA
<213> ORGANISM: Artificial Sequence
<220> FEATURE:
<223> OTHER INFORMATION: Synthetic Probe

<400> SEQUENCE: 719
ccactactac tactctaatt gctc                                            24

<210> SEQ ID NO 720
<211> LENGTH: 21
<212> TYPE: DNA
<213> ORGANISM: Artificial Sequence
<220> FEATURE:
<223> OTHER INFORMATION: Synthetic Probe

<400> SEQUENCE: 720
cagccgaccg accctccaac c                                               21

<210> SEQ ID NO 721
<211> LENGTH: 25
<212> TYPE: DNA
<213> ORGANISM: Artificial Sequence
<220> FEATURE:
<223> OTHER INFORMATION: Synthetic Probe

<400> SEQUENCE: 721
aaaagaatct ttatcccttt ccccc                                           25

<210> SEQ ID NO 722
<211> LENGTH: 23
<212> TYPE: DNA
<213> ORGANISM: Artificial Sequence
<220> FEATURE:
<223> OTHER INFORMATION: Synthetic Probe

<400> SEQUENCE: 722
ctcctaaggc tgcttctgaa tca                                             23

<210> SEQ ID NO 723
<211> LENGTH: 25
<212> TYPE: DNA
<213> ORGANISM: Artificial Sequence
<220> FEATURE:
<223> OTHER INFORMATION: Synthetic Probe
```

```
<400> SEQUENCE: 723
tgacccaccc agaacttcat agcca                                         25

<210> SEQ ID NO 724
<211> LENGTH: 23
<212> TYPE: DNA
<213> ORGANISM: Artificial Sequence
<220> FEATURE:
<223> OTHER INFORMATION: Synthetic Probe

<400> SEQUENCE: 724
gaaggcgaac cacttcccgg aag                                           23

<210> SEQ ID NO 725
<211> LENGTH: 23
<212> TYPE: DNA
<213> ORGANISM: Artificial Sequence
<220> FEATURE:
<223> OTHER INFORMATION: Synthetic Probe

<400> SEQUENCE: 725
tgggacctca gcatacccaa tag                                           23

<210> SEQ ID NO 726
<211> LENGTH: 20
<212> TYPE: DNA
<213> ORGANISM: Artificial Sequence
<220> FEATURE:
<223> OTHER INFORMATION: Synthetic Probe

<400> SEQUENCE: 726 cccectcaat ggcctgcttc                                               20

<210> SEQ ID NO 727
<211> LENGTH: 24
<212> TYPE: DNA
<213> ORGANISM: Artificial Sequence
<220> FEATURE:
<223> OTHER INFORMATION: Synthetic Probe

<400> SEQUENCE: 727
accagcctgg gcagcatagc gaaa                                          24

<210> SEQ ID NO 728
<211> LENGTH: 25
<212> TYPE: DNA
<213> ORGANISM: Artificial Sequence
<220> FEATURE:
<223> OTHER INFORMATION: Synthetic Probe

<400> SEQUENCE: 728
tcctctctaa gactcaagaa tctgg                                         25

<210> SEQ ID NO 729
<211> LENGTH: 19
<212> TYPE: DNA
<213> ORGANISM: Artificial Sequence
<220> FEATURE:
<223> OTHER INFORMATION: Synthetic Probe

<400> SEQUENCE: 729
tcgatccgag cccgacggg                                                19

<210> SEQ ID NO 730
<211> LENGTH: 19
```

```
<212> TYPE: DNA
<213> ORGANISM: Artificial Sequence
<220> FEATURE:
<223> OTHER INFORMATION: Synthetic Probe

<400> SEQUENCE: 730
ggagagcagg aggcggccg                                              19

<210> SEQ ID NO 731
<211> LENGTH: 18
<212> TYPE: DNA
<213> ORGANISM: Artificial Sequence
<220> FEATURE:
<223> OTHER INFORMATION: Synthetic Probe

<400> SEQUENCE: 731
tccccgggcc aggagagc                                               18

<210> SEQ ID NO 732
<211> LENGTH: 24
<212> TYPE: DNA
<213> ORGANISM: Artificial Sequence
<220> FEATURE:
<223> OTHER INFORMATION: Synthetic Probe

<400> SEQUENCE: 732
aggagacaac gttagcctgg tggc                                        24

<210> SEQ ID NO 733
<211> LENGTH: 23
<212> TYPE: DNA
<213> ORGANISM: Artificial Sequence
<220> FEATURE:
<223> OTHER INFORMATION: Synthetic Probe

<400> SEQUENCE: 733
ccactgaacg gcacgattcc agc                                         23

<210> SEQ ID NO 734
<211> LENGTH: 23
<212> TYPE: DNA
<213> ORGANISM: Artificial Sequence
<220> FEATURE:
<223> OTHER INFORMATION: Synthetic Probe

<400> SEQUENCE: 734
caccgacccc aggaaataac ggg                                         23

<210> SEQ ID NO 735
<211> LENGTH: 21
<212> TYPE: DNA
<213> ORGANISM: Artificial Sequence
<220> FEATURE:
<223> OTHER INFORMATION: Synthetic Probe

<400> SEQUENCE: 735
cccacgttgg ccaagaggtc t                                           21

<210> SEQ ID NO 736
<211> LENGTH: 22
<212> TYPE: DNA
<213> ORGANISM: Artificial Sequence
<220> FEATURE:
<223> OTHER INFORMATION: Synthetic Probe

<400> SEQUENCE: 736
```
gacagtcccc gtgaacacgt gg    22

<210> SEQ ID NO 737
<211> LENGTH: 23
<212> TYPE: DNA
<213> ORGANISM: Artificial Sequence
<220> FEATURE:
<223> OTHER INFORMATION: Synthetic Probe

<400> SEQUENCE: 737
accttgctga caccttgctg aca    23

<210> SEQ ID NO 738
<211> LENGTH: 24
<212> TYPE: DNA
<213> ORGANISM: Artificial Sequence
<220> FEATURE:
<223> OTHER INFORMATION: Synthetic Probe

<400> SEQUENCE: 738
ccaccactac tactctaatt gctc    24

<210> SEQ ID NO 739
<211> LENGTH: 21
<212> TYPE: DNA
<213> ORGANISM: Artificial Sequence
<220> FEATURE:
<223> OTHER INFORMATION: Synthetic Probe

<400> SEQUENCE: 739
cagcagaccg accctccaac c    21

<210> SEQ ID NO 740
<211> LENGTH: 25
<212> TYPE: DNA
<213> ORGANISM: Artificial Sequence
<220> FEATURE:
<223> OTHER INFORMATION: Synthetic Probe

<400> SEQUENCE: 740
aaaataatct ttatcccttt ccccc    25

<210> SEQ ID NO 741
<211> LENGTH: 23
<212> TYPE: DNA
<213> ORGANISM: Artificial Sequence
<220> FEATURE:
<223> OTHER INFORMATION: Synthetic Probe

<400> SEQUENCE: 741
ctcccaaggc tgcttctgaa tca    23

<210> SEQ ID NO 742
<211> LENGTH: 25
<212> TYPE: DNA
<213> ORGANISM: Artificial Sequence
<220> FEATURE:
<223> OTHER INFORMATION: Synthetic Probe

<400> SEQUENCE: 742
tgacacaccc agaacttcat agcca    25

<210> SEQ ID NO 743
<211> LENGTH: 23
<212> TYPE: DNA
<213> ORGANISM: Artificial Sequence
<220> FEATURE:
<223> OTHER INFORMATION: Synthetic Probe

<400> SEQUENCE: 743
gaagccgaac cacttcccgg aag                                   23

<210> SEQ ID NO 744
<211> LENGTH: 23
<212> TYPE: DNA
<213> ORGANISM: Artificial Sequence
<220> FEATURE:
<223> OTHER INFORMATION: Synthetic Probe

<400> SEQUENCE: 744
tggggcctca gcatacccaa tag                                   23

<210> SEQ ID NO 745
<211> LENGTH: 20
<212> TYPE: DNA
<213> ORGANISM: Artificial Sequence
<220> FEATURE:
<223> OTHER INFORMATION: Synthetic Probe

<400> SEQUENCE: 745 cccttcaat ggcctgcttc                                        20

<210> SEQ ID NO 746
<211> LENGTH: 24
<212> TYPE: DNA
<213> ORGANISM: Artificial Sequence
<220> FEATURE:
<223> OTHER INFORMATION: Synthetic Probe

<400> SEQUENCE: 746
accaacctgg gcagcatagc gaaa                                  24

<210> SEQ ID NO 747
<211> LENGTH: 25
<212> TYPE: DNA
<213> ORGANISM: Artificial Sequence
<220> FEATURE:
<223> OTHER INFORMATION: Synthetic Probe

<400> SEQUENCE: 747
ttctttctaa gactcaagaa tctgg                                 25

<210> SEQ ID NO 748
<211> LENGTH: 19
<212> TYPE: DNA
<213> ORGANISM: Artificial Sequence
<220> FEATURE:
<223> OTHER INFORMATION: Synthetic Probe

<400> SEQUENCE: 748
tcgacccgag cccgacggg                                        19

<210> SEQ ID NO 749
<211> LENGTH: 13
<212> TYPE: DNA
<213> ORGANISM: Artificial Sequence
<220> FEATURE:
<223> OTHER INFORMATION: Synthetic Probe

<400> SEQUENCE: 749
cggccgcctc ctg                                              13

<210> SEQ ID NO 750
<211> LENGTH: 12
<212> TYPE: DNA
<213> ORGANISM: Artificial Sequence
<220> FEATURE:
<223> OTHER INFORMATION: Synthetic Probe

<400> SEQUENCE: 750
gctctcctgg cc                                                           12

<210> SEQ ID NO 751
<211> LENGTH: 18
<212> TYPE: DNA
<213> ORGANISM: Artificial Sequence
<220> FEATURE:
<223> OTHER INFORMATION: Synthetic Probe

<400> SEQUENCE: 751
gccaccaggc taacgttg                                                     18

<210> SEQ ID NO 752
<211> LENGTH: 17
<212> TYPE: DNA
<213> ORGANISM: Artificial Sequence
<220> FEATURE:
<223> OTHER INFORMATION: Synthetic Probe

<400> SEQUENCE: 752
gctggaatcg tgccgtt                                                      17

<210> SEQ ID NO 753
<211> LENGTH: 17
<212> TYPE: DNA
<213> ORGANISM: Artificial Sequence
<220> FEATURE:
<223> OTHER INFORMATION: Synthetic Probe

<400> SEQUENCE: 753
cccgttattt cctgggg                                                      17

<210> SEQ ID NO 754
<211> LENGTH: 15
<212> TYPE: DNA
<213> ORGANISM: Artificial Sequence
<220> FEATURE:
<223> OTHER INFORMATION: Synthetic Probe

<400> SEQUENCE: 754
agacctcttg gccaa                                                        15

<210> SEQ ID NO 755
<211> LENGTH: 16
<212> TYPE: DNA
<213> ORGANISM: Artificial Sequence
<220> FEATURE:
<223> OTHER INFORMATION: Synthetic Probe

<400> SEQUENCE: 755
ccacgtgttc acgggg                                                       16

<210> SEQ ID NO 756
<211> LENGTH: 17
<212> TYPE: DNA
<213> ORGANISM: Artificial Sequence
<220> FEATURE:
<223> OTHER INFORMATION: Synthetic Probe

<400> SEQUENCE: 756
tgtcagcaag gtgtcag                                                 17

<210> SEQ ID NO 757
<211> LENGTH: 18
<212> TYPE: DNA
<213> ORGANISM: Artificial Sequence
<220> FEATURE:
<223> OTHER INFORMATION: Synthetic Probe

<400> SEQUENCE: 757
gagcaattag agtagtag                                                18

<210> SEQ ID NO 758
<211> LENGTH: 15
<212> TYPE: DNA
<213> ORGANISM: Artificial Sequence
<220> FEATURE:
<223> OTHER INFORMATION: Synthetic Probe

<400> SEQUENCE: 758
ggttggaggg tcggt                                                   15

<210> SEQ ID NO 759
<211> LENGTH: 19
<212> TYPE: DNA
<213> ORGANISM: Artificial Sequence
<220> FEATURE:
<223> OTHER INFORMATION: Synthetic Probe

<400> SEQUENCE: 759
gggggaaagg gataaagat                                               19

<210> SEQ ID NO 760
<211> LENGTH: 17
<212> TYPE: DNA
<213> ORGANISM: Artificial Sequence
<220> FEATURE:
<223> OTHER INFORMATION: Synthetic Probe

<400> SEQUENCE: 760
tgattcagaa gcagcct                                                 17

<210> SEQ ID NO 761
<211> LENGTH: 19
<212> TYPE: DNA
<213> ORGANISM: Artificial Sequence
<220> FEATURE:
<223> OTHER INFORMATION: Synthetic Probe

<400> SEQUENCE: 761
tggctatgaa gttctgggt                                               19

<210> SEQ ID NO 762
<211> LENGTH: 17
<212> TYPE: DNA
<213> ORGANISM: Artificial Sequence
<220> FEATURE:
<223> OTHER INFORMATION: Synthetic Probe

<400> SEQUENCE: 762
cttccgggaa gtggttc                                                 17

<210> SEQ ID NO 763
<211> LENGTH: 17

```
<212> TYPE: DNA
<213> ORGANISM: Artificial Sequence
<220> FEATURE:
<223> OTHER INFORMATION: Synthetic Probe

<400> SEQUENCE: 763
ctattgggta tgctgag                                                  17

<210> SEQ ID NO 764
<211> LENGTH: 14
<212> TYPE: DNA
<213> ORGANISM: Artificial Sequence
<220> FEATURE:
<223> OTHER INFORMATION: Synthetic Probe

<400> SEQUENCE: 764
gaagcaggcc attg                                                     14

<210> SEQ ID NO 765
<211> LENGTH: 18
<212> TYPE: DNA
<213> ORGANISM: Artificial Sequence
<220> FEATURE:
<223> OTHER INFORMATION: Synthetic Probe

<400> SEQUENCE: 765
tttcgctatg ctgcccag                                                 18

<210> SEQ ID NO 766
<211> LENGTH: 19
<212> TYPE: DNA
<213> ORGANISM: Artificial Sequence
<220> FEATURE:
<223> OTHER INFORMATION: Synthetic Probe

<400> SEQUENCE: 766
ccagattctt gagtcttag                                                19

<210> SEQ ID NO 767
<211> LENGTH: 13
<212> TYPE: DNA
<213> ORGANISM: Artificial Sequence
<220> FEATURE:
<223> OTHER INFORMATION: Synthetic Probe

<400> SEQUENCE: 767
cccgtcgggc tcg                                                      13
```

METHOD FOR DETECTING MUTATIONS IN SINGLE CELLS OR SINGLE MOLECULES

CROSS-REFERENCE TO RELATED APPLICATIONS

The present application is a 35 U.S.C. § 371 national phase application from, and claims priority to, International Application No. PCT/US2014/025703, filed Mar. 13, 2014, and published under PCT Article 21(2) in English, which claims priority under 35 U.S.C. § 119(e) to U.S. Provisional Application No. 61/785,498, filed Mar. 14, 2013, all of which applications are incorporated herein by reference in their entireties.

STATEMENT REGARDING FEDERALLY SPONSORED RESEARCH OR DEVELOPMENT

This invention was made with government support under Grant No. 1DP2OD008514 awarded by the National Institute of Health (NIH). The government has certain rights in the invention.

BACKGROUND OF THE INVENTION

Genome-wide association studies have highlighted the need for tools to quantify the expression of genes in an allele-specific manner to show how disease-associated single nucleotide variants (SNVs) affect transcription. Advances in single cell imaging have enabled researchers to detect individual RNAs with single molecule resolution (Femino et al., 1998, Science 280:585-590; Raj et al., 2008, Nat Methods 5:877-879), or in conjunction with single chromosomes (Levesque and Raj, 2013, Nat Methods, doi: 10.1038/nmeth.2372). However, such methods are typically unable to distinguish SNVs in these molecules, and the few methods available for in situ SNV detection tend to be complex and suffer from low efficiency (Larsson et al., 2004, Nat Methods 1:227-232; Larsson et al., 2010, Nat Methods 7:395-397). In one method, a complex enzymatic scheme was used to amplify signals from SNVs on RNA molecules to the point where SNVs could be detected in situ (Larsson et al., 2010, Nat Methods 7:395-397). However, the detection efficiency of this method was very low, likely on the order of 1% or lower in many cases. Accordingly, development of a method for SNV detection that is able to measure allele-specific gene expression at the single-cell and single-molecule level would be of great utility in a variety of fields, including genetics and transcription (Ferguson-Smith, 2011, Nat Rev Genet 12:565-575; Gimelbrant et al., 2007, Science 318:1136-1140; Gregg et al., 2010, Science 329: 643-648).

One of the primary difficulties associated with detecting a difference of a single base via RNA fluorescence in situ hybridization (FISH) is that an oligonucleotide probe on the order of 20 bases or more often hybridizes to the RNA despite the presence of a single mismatch. On the other hand, very short oligonucleotide probes, while able to discriminate between single-base differences, often fail to remain bound to the target due to reduced binding energy. In either case, distinguishing legitimate signals from false positives can be problematic when using just a single probe.

Thus, there is a need in the art for a method for SNV detection that can efficiently measure gene expression at the population, single cell or single molecule level. The present invention addresses this unmet need in the art.

BRIEF SUMMARY OF THE INVENTION

The invention includes a method for detecting a mutation in a target nucleic acid. The method comprises hybridizing at least one labeled, masked detection probe to a target nucleic acid having at least one mutation, wherein the hybridization region of the detection probe and target nucleic acid includes the mutation. In one embodiment, the mutation is a small-scale mutation selected from the group consisting of a single nucleotide variant (SNV), insertion, and deletion. In another embodiment, the method further comprises hybridizing the target nucleic acid with at least one labeled guide probe. In yet another embodiment, the hybridization region of the at least one guide probe and target nucleic acid does not include the mutation. In a further embodiment, the at least one guide probe and the detection probe are each labeled with a fluorophore. In another embodiment, the fluorophore for the at least one guide probe and the fluorophore for the detection probe are distinguishable when visualized.

In another embodiment, the method of the invention further comprises detecting the at least one guide probe fluorophore in a first image; detecting the detection probe fluorophore in a second image; and detecting the mutation in the nucleotide sequence of the target nucleic acid by comparing said first image with said second image to determine a colocation of the at least one guide probe fluorophore and the detection probe fluorophore.

In yet another embodiment, the detection probe is masked by an oligonucleotide that hybridizes to a portion of a nucleotide sequence of the detection probe. In a further embodiment, the detection probe hybridizes to the target nucleic acid on the unmasked region of the detection probe. In yet another embodiment, the oligonucleotide masking a portion of the nucleotide sequence of the detection probe denatures from the detection probe when the detection probe hybridizes to the target nucleic acid. In another embodiment, the previously masked portion of the detection probe hybridizes to the target nucleic acid subsequent to the oligonucleotide denaturing from the detection probe.

In an additional embodiment, the target nucleic acid is a ribonucleic acid (RNA). In another embodiment, the RNA is selected from the group consisting of messenger RNA, intronic RNA, exonic DNA, and non-coding RNA. In yet another embodiment, the detection probe comprises a nucleotide sequence of at least 10 bases. In a further embodiment, the at least one guide probe comprises a nucleotide sequence of at least 10 bases. In yet a further embodiment, the oligonucleotide masking the detection probe has a nucleotide sequence of at least 5 bases. In another embodiment, the detection probe comprises an unmasked nucleotide sequence of at least 2 bases when the oligonucleotide mask is hybridized to the detection probe.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A through FIG. 1D, is a set of diagrams, images, and graphs showing that toehold probes enable SNV detection on individual RNA molecules in situ. FIG. 1A: Schematic of the principle behind in situ SNV detection, using the T1799A mutation of BRAF as an example. FIG. 1B: Visualization of the guide probe detecting BRAF mRNA (ATTO488, left panel) and the wild-type and mutant detection probes (Cy5, Cy3, middle and right panels, respectively). FIG. 1C: Classification of RNA as being either wild-type or mutant using the detection probes. FIG. 1D: Quantification and classification of RNA as wild-type or mutant in a group of single cells. Left: cells with only wild-type BRAF; middle: cells that are heterozygous for BRAF; right: cells that are mutant for BRAF. Scale bars are 5 µm long.

FIG. 2, comprising FIG. 2A: Allelic imbalance was quantified in the population of the indicated genes by measuring the probability that a transcript comes from either the maternal or paternal allele. Error bars reflect 99% confidence intervals. FIG. 2B: Using a statistical model, the number of RNAs required to determine whether an allelic imbalance exists for a given actual imbalance was examined. FIG. 2C: Statistical examination of the likelihood of finding a population with the measured number of maternal vs. paternal transcripts given a null hypothesis in which each mRNA was randomly assigned as being either maternal or paternal. As depicted, DNMT1 shows single cell imbalance, whereas SUZ12 and SKA3 do not.

FIG. 3, comprising FIG. 3A: Illustration of the chromosome detection method. iceFISH probes that target chromosome 19 and SNV detection probes targeting 19 SNPs within 15 of these genes on the paternal chromosome were designed. FIG. 3B: Example images showing the two copies of chromosome 19 (dashed regions) with the computationally identified colocalized detection probes labeled with circles.

FIG. 4, comprising FIG. 4A: The WM3918 cell line was probed, which is homozygous for the wild-type allele, with probes targeting both the mutant and wild type allele, either with or without the mask (left, right, respectively). Each bar represents the mRNA counts from a single cell. It was found that in the presence of mask, the vast majority of transcripts are wild-type, whereas without mask, a large fraction of the mutant probe spuriously bound to the target. FIG. 4B: Other targets also showed single base mismatch discrimination. Sequences were targeted as shown with both perfect match and mismatch detection probes, and found that the perfect match probe was far more likely to bind.

DETAILED DESCRIPTION

Figure 1A:
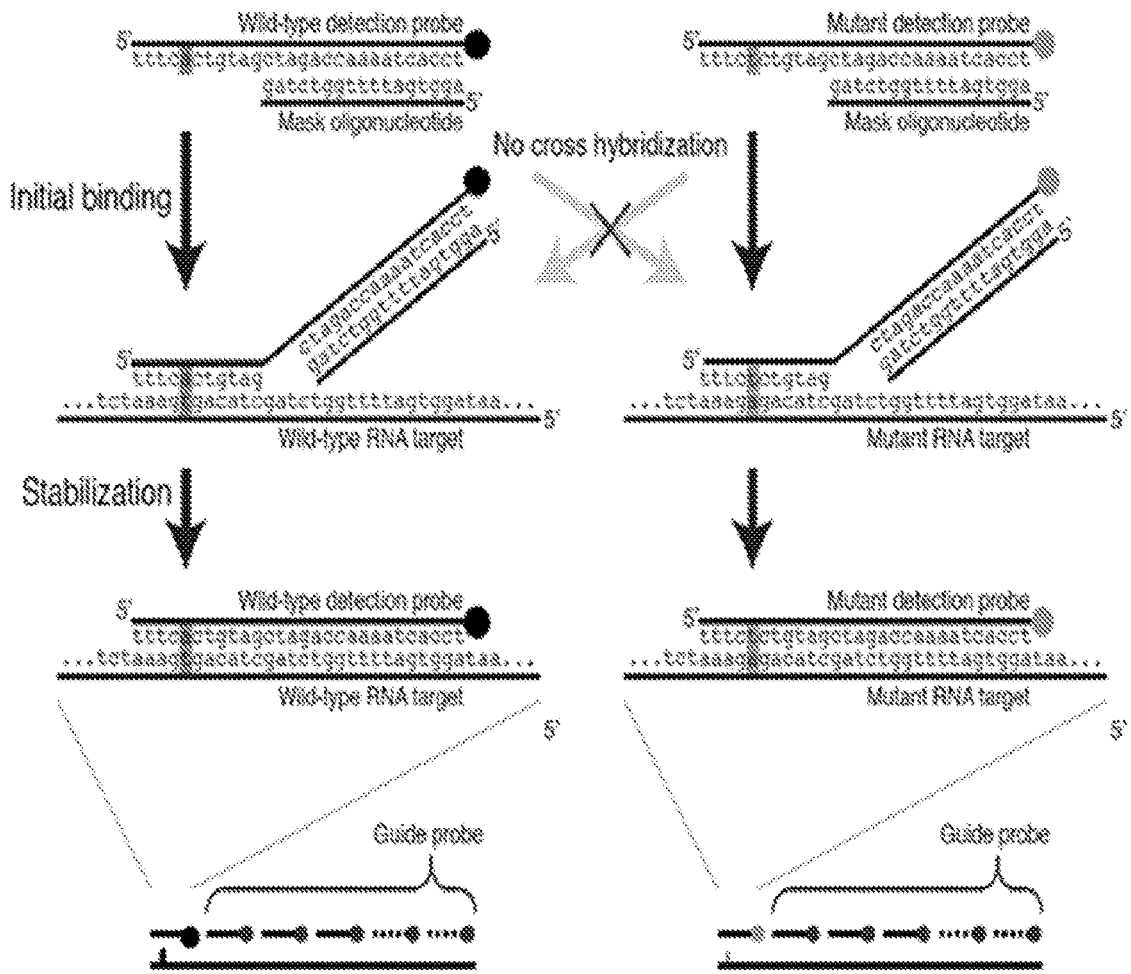

The present invention relates to a fluorescence in situ hybridization method for detecting a mutation on an individual RNA transcript. The method provides high-efficiency detection of mutations in the sequence of individual RNA molecules in single cells.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of ±20% or ±10%, ±5%, ±1%, or ±0.1% from the specified value, as such variations are appropriate.

The term "mutation" as used herein refers to any change of one or more nucleotides in a nucleotide sequence.

The term "single nucleotide variant" (SNV) refers to a single nucleotide in a DNA or RNA sequence that is different in comparison to a control or reference sequence. The term "single nucleotide variant" includes and encompasses single nucleotide polymorphisms (SNPs), which are DNA sequence variations characterized by a single nucleotide in the genome sequence that is altered in at least 1% of the human population.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'-ATTGCC-5' and 3'-TATGGC-5' share 75% homology.

As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene. A "coding region" of an mRNA molecule also consists of the nucleotide residues of the mRNA molecule which are matched with an anti-codon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids, which have been substantially purified from other components, which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

A "portion" of a polynucleotide means at least at least about five to about fifty sequential nucleotide residues of the polynucleotide. It is understood that a portion of a polynucleotide may include every nucleotide residue of the polynucleotide.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Naturally occurring" as used herein describes a composition that can be found in nature as distinct from being artificially produced. For example, a nucleotide sequence present in an organism, which can be isolated from a source in nature and which has not been intentionally modified by a person in the laboratory, is naturally occurring.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

The terms "patient," "subject," "individual," and the like are used interchangeably herein, and refer to any animal, or cells thereof whether in vitro or in situ, amenable to the methods described herein. Preferably, the patient, subject or individual is a mammal, and more preferable, a human.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for detecting nucleotide mutations. For example, the invention can be used to detect small-scale mutations including, but not limited to single nucleotide variants (SNVs), point mutations small insertions, and small deletions.

Single nucleotide polymorphisms (SNPs) are changes to a single DNA base in the genetic sequence that can lead to differences between individuals. Often, these SNPs appear in the transcribed portion of a gene and as such also appear as single nucleotide variants (SNVs) in the sequence of the transcribed RNA. The present invention relates to a method for detecting these SNVs on individual RNA molecules in single cells via fluorescence microscopy using in situ hybridization.

In situ hybridization (ISH) is a method that utilizes nucleic acid probes to detect DNA or RNA targets in cells via Watson-Crick base pairing of the probe to the target. A version of fluorescence-based ISH targeting RNA (RNA FISH) in which tens of fluorescently-labeled DNA oligonucleotide probes are used, each of which bind to different segments of the same RNA target, has been previously described (Raj et al., 2008, Nat Methods 5:877-879) and is incorporated by reference herein in its entirety. The method in Raj leads to a signal concentration at the target RNA, appearing as a bright spot in a fluorescence microscope. However, the RNA FISH method described in Raj does not provide the necessary discriminating power to distinguish small-scale mutations at the RNA level. This is because each DNA oligonucleotide probe will typically bind to a target despite the presence of a single or small number of mismatched, inserted or deleted nucleotides.

One method relating to in situ detection of SNVs on RNA molecules has been described demonstrating the use of signal amplification via a complex enzymatic scheme (Larsson et al., 2010, Nat Methods 7:395-397). However, the detection efficiency of this method is reported to be highly variable, leading to unreliable quantification.

One issue associated with detecting small-scale mutations, including a difference of a single base, via RNA FISH is that hybridization of relatively long oligonucleotide probes to the RNA may occur, despite not being fully complementary to the target. Conversely, very short oligonucleotide probes, while able to discriminate between single base differences, will often fail to remain bound to the target due to reduced binding energy. Additionally, in either case, distinguishing signals indicating the presence of a mutation on a target RNA from a false positive result can be difficult or impossible when using only a single oligonucleotide probe. The method described herein employs a strategy to overcome these issues.

In order to distinguish between single-base mismatches, the method of the present invention includes a "toehold probe" strategy in which a single-stranded DNA oligonucleotide mutation-detection probe, designed to bind to the target RNA region including the mutation, is hybridized to a shorter DNA "mask" oligonucleotide. In one embodiment, the mask oligonucleotide blocks a portion of the detection probe from binding to the targeted RNA (FIG. 1A) (Zhang & Winfree, 2009, J Am Chem Soc 131:17303-17314; Zhang et al., 2012, Nat Chem 4:208-214; Li et al., 2002, Nucleic Acids Res 30:E5). The remaining single-stranded portion of the oligonucleotide mutation-detection probe may be of a short enough length to confer selectivity based on single base mismatches in the targeted RNA to which it selectively binds. Once the oligonucleotide mutation-detection probe is bound to the target RNA, the mask oligonucleotide dissociates from the mutation-detection probe, enabling the remainder of the mutation-detection probe length that was previously masked to bind to the target RNA. Thus, the method of the present invention comprises probes that have specificity for the desired mutation while still retaining a sufficient binding energy to prevent the detection probe from rapidly dissociating from the target after hybridization.

Targeted Nucleic Acid Sample

As contemplated herein, the present invention may be used in the analysis of any nucleic acid sample for which mutational analysis may be applied, as would be understood by those having ordinary skill in the art. For example, in certain embodiments, the nucleic acid can be mRNA. However, it should appreciated that there is no limitation to the type of nucleic acid sample, which may include without limitation, any type of RNA, cDNA, genomic DNA, fragmented RNA or DNA and the like. In certain embodiments, the nucleic acid sample comprises at least one of messenger RNA, intronic RNA, exonic DNA, and non-coding RNA. The nucleic acid may be prepared for hybridization according to any manner as would be understood by those having ordinary skill in the art. It should also be appreciated that the sample may be an isolated nucleic acid sample, or it may form part of a lysed cell, or it may be an intact living cell. Samples may further be individual cells, or a population of cells, such as a population of cells corresponding to a particular tissue. It should be appreciated that there is no limitation to the size or type of sample, provided the sample includes at least one nucleic acid therein. For example, the sample may be derived or obtained from one or more eukaryotic cells, prokaryotic cells, bacteria, virus, exosome, liposome, and the like.

RNA FISH Method

The present invention includes use of a highly sensitive and specific RNA FISH method to identify mutations in a targeted nucleic acid sequence. Additional description and explanation of RNA FISH methodologies can be found in copending patent application publication numbers WO/2010/030818 and WO 2012/106711, the entire contents of each are incorporated by reference herein it their entirety.

Probes useful in this invention may be DNA, RNA or mixtures of DNA and RNA. They may include non-natural nucleotides, and they may include non-natural internucleotide linkages. Non-natural nucleotides that increase the binding affinity of probes include 2'-O-methyl ribonucleotides, for example. The lengths of probes useful in this invention can be about 15-40 nucleotides for typical DNA or RNA probes of average binding affinity. In certain embodiments, the guide probes are about 10-50 nucleotides long, detection probes are about 10-50 nucleotides long, and masks (short oligonucleotides) are about 5-48 nucleotides long. If means are included to increase a probe's binding affinity, the probe can be shorter, as short as seven nucleotides, as persons in the art will appreciate. A fluorophore can be attached to a probe at any position, including, without limitation, attaching a fluorophore to one end of a probe, preferably to the 3' end. The probes may be included in a hybridization solution that contains the probes in excess.

A single cell can be probed simultaneously for multiple RNA target sequences, either more than one target sequence of one RNA molecule, or one or more sequences of different RNA molecules. Additionally, one target sequence of an RNA molecule can be probed with more than one set of probes, wherein each set is labeled with a distinguishable fluorophore, and the fluorophores are distinguishable. In one embodiment, the guide probe and the detection probe will have distinguishable fluorophores. Using more than one color for each of multiple targets permits the use of color-coding schemes in highly multiplexed probing methods, according to the present invention.

Methods of the present invention may also include determining if one or more spots representing a target mutation sequence is present. Methods according to the present invention also include counting spots of a given color corresponding to a given RNA mutation species. When it is desired to detect more than one mutation, different sets of probes labeled with distinct fluorophores can be used in the same hybridization mixture.

Spots can be detected utilizing microscopic methods. A confocal microscope, or a wide-field fluorescence microscope is sufficient. There is no limitation to the type of microscope used.

In another aspect, the present invention includes sets of probes for in situ hybridization that enable detection of SNVs on individual RNA molecules in cells. The probes render each molecule so intensely fluorescent that it can be seen as a fine fluorescent spot in fluorescence microscopy. A computer program can be used to identify and count all the RNA molecules in the cell from the microscopic image.

The invention also provides a kit, generally comprising a set of probes, an instruction manual for performing any of the methods contemplated herein, and optionally the computer-readable media as described herein.

Method

Accordingly, the present invention relates to a method for reliably detecting mutations using RNA FISH. The method can be generally described as including the following steps.

The method comprises detecting the target RNA of interest in a sample via a conventional RNA FISH method, without having any oligonucleotide probes binding to the region of the RNA containing the mutation. These initial oligonucleotide probes serve as control probes, and are referred to herein as guide probes, since the use of these probes determines the location of the RNA of interest, regardless of whether or not it contains a mutation. The guide probes of the present invention are labeled with a fluorophore that is spectrally distinct from any other types of fluorophores associated with other probes described herein.

Figure 1A:
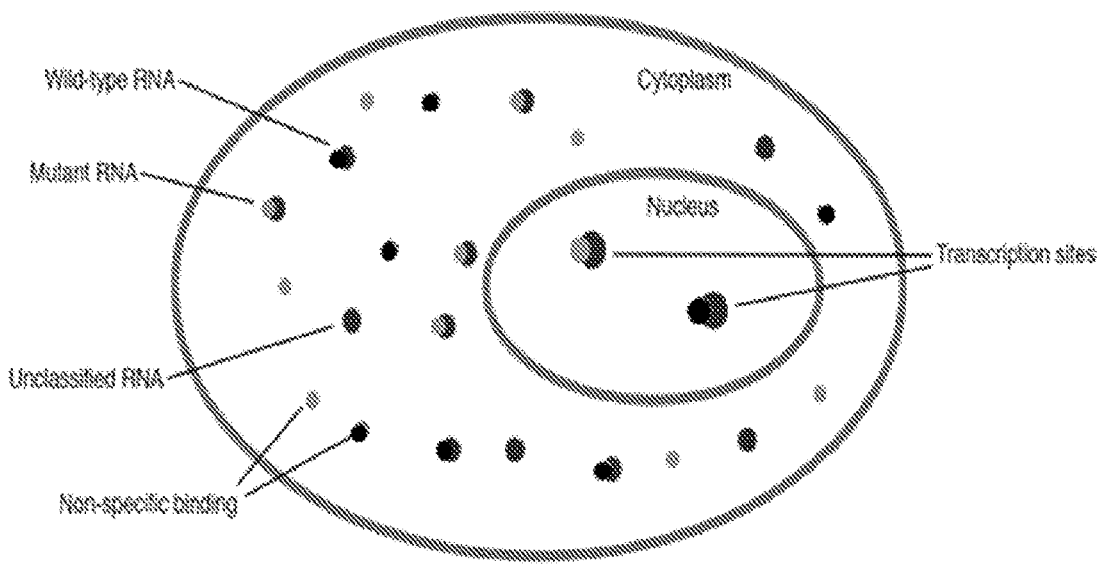

In one embodiment, the method comprises construction of a second oligonucleotide probe that serves as a mutation detection oligonucleotide probe (the detection probe). In one embodiment, the detection probe is a 28-base probe. The detection probe of the present invention targets a mutation, and is labeled with a fluorophore that is spectrally-distinct from the guide probe. In order to make sure that the mutation detection oligonucleotide probe only binds to the target sequence containing the mutation, and not to RNA molecules that do not contain the mutation, a DNA oligonucleotide mask is introduced that binds to a portion of the mutation detection oligonucleotide probe, as shown in FIG. 1. The unmasked region of the mutation detection oligonucleotide probe left exposed is relatively short, and will not bind to a sequence if there is at least one base mismatch in the target. The mutation detection oligonucleotide probe can be used to detect mutations in the RNA of interest.

In certain embodiments, the method comprises hybridization of the detection probe and mask. In certain embodiments, the hybridized detection probe/mask complex is added to the sample under reaction conditions suitable for the unmasked region of the detection probe to hybridize to the targeted RNA of interest.

In certain embodiments, the guide probe, detection probe, and oligonucleotide mask are simultaneously applied to the RNA of interest. For example in one embodiment, the method comprises applying a hybridization solution comprising the guide probe, detection probe, and oligonucleotide mask, to a sample. The method further comprise providing suitable conditions to allow for hybridization of the guide probe to the RNA, hybridization of the mask to the detection mask, and hybridization of the unmasked portion of the detection probe to a mutation-containing portion of the RNA.

After the detection probe hybridizes to the targeted RNA of interest (containing the mutation), the mask oligonucleotide denatures from the detection probe allowing the previously masked portion of the detection probe sequence to hybridize to the targeted RNA of interest.

In certain embodiments, the method of the invention comprises detecting more than one mutation in a sample. For example, in one embodiment, the method comprises contacting the sample with more than one detection probe, where each detection probe targets a different mutation, and where each detection probe is labeled with a fluorophore that is spectrally-distinct from the guide probe and spectrally-distinct from all other detection probes used.

The method of the present invention has a much higher efficiency than any methods presently described in the art for detecting small-scale mutations. Further, the method provides significantly more quantitative and reliable results than existing methods. In addition, as compared with biochemical methods such as sequencing, the method of the present invention may provide considerable cost advantages for detecting a particular mutation cheaply and effectively in a particular population of cells. Additionally, the method can work well in tissue sections.

For example, in existing methods, the use of a single probe can lead to a large number of false-positive signals, because every off-target binding event is indistinguishable from on-target binding. Such false-positives can be avoided by relying on the colocalization of multiple probes (Raj et al., 2008, Nat Methods 5:877-879), but colocalization is typically not possible when only a single probe can be used, as is the case in detection of a mutation in a single nucleotide or small number of nucleotides. Therefore, the method of the present invention uses multiple oligonucleotide control probes, collectively referred to as "guide" probes, that bind to the target RNA, thereby robustly identifying the target RNA. Detection probe signals are only considered as legitimate if they colocalize with a guide probe signal, thereby clearly distinguishing false positive signals from true positives (FIG. 1A).

As with any in situ hybridization probe, the mutation detection oligonucleotide probes, i.e. detection probes, of the present invention may have a considerable amount of off-target binding, which would be impossible to distinguish from the signals indicating the presence of a mutation on the RNA of interest. However, the method of the present invention utilizes the fact that the RNA of interest, or target RNA, has been separately labeled using at least one guide probe, i.e. an initial oligonucleotide control probe. Therefore, any detection probes that are bound to the correct target will colocalize with a guide probe, whereas detection probes that do not colocalize with a guide probe are binding off-target. These colocalized spots, comprising a fluorophore from at least one guide probe and a fluorophore from a detection probe, can be determined using computational methods described herein for detecting spots in microscope images, thereby allowing identification of target RNA that have the mutation of interest.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Figure 4A:
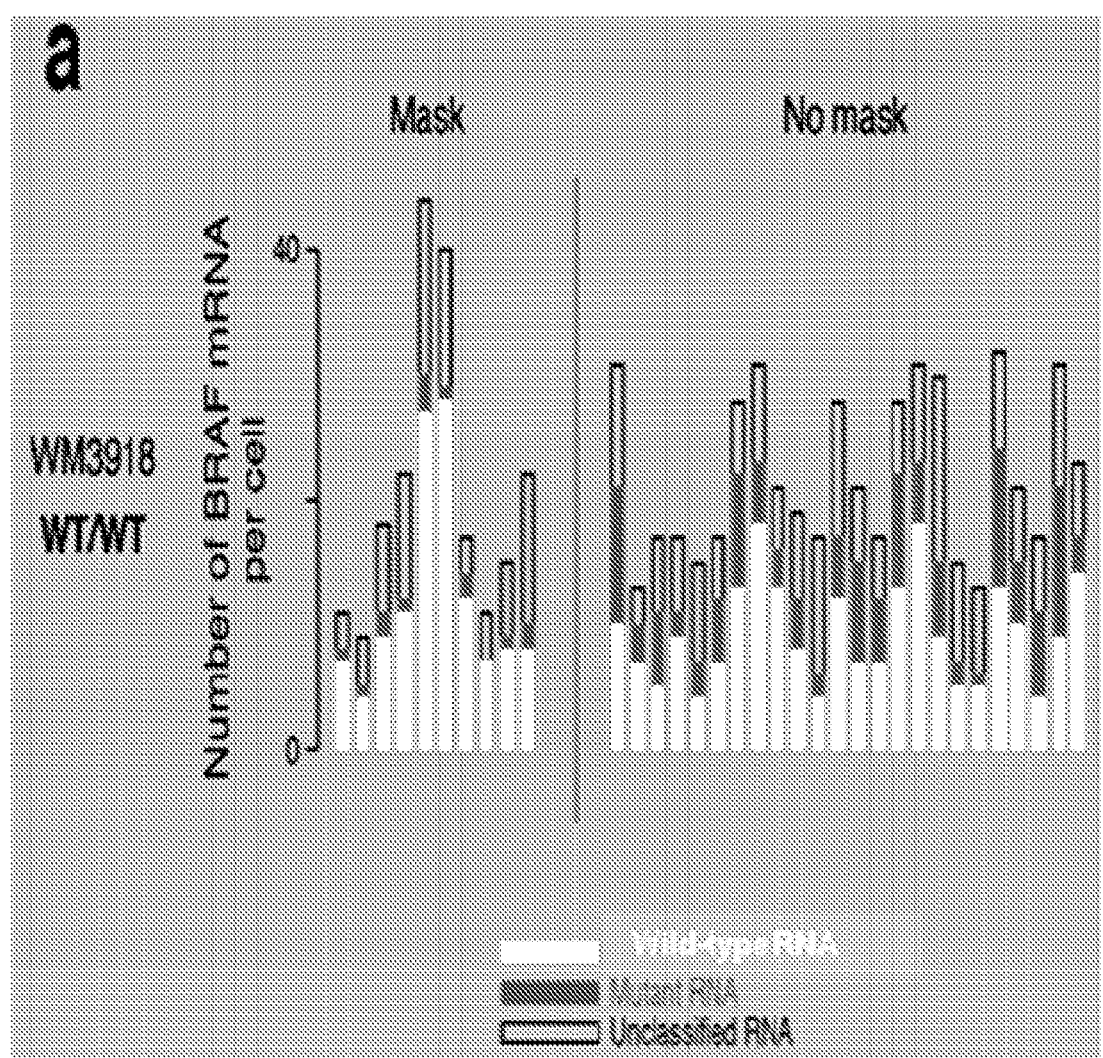
FIGS. 4A and 4B, is a set of graphs showing that the addition of a mask is required for proper discrimination of single nucleotide variant targets.
Figure 4B:
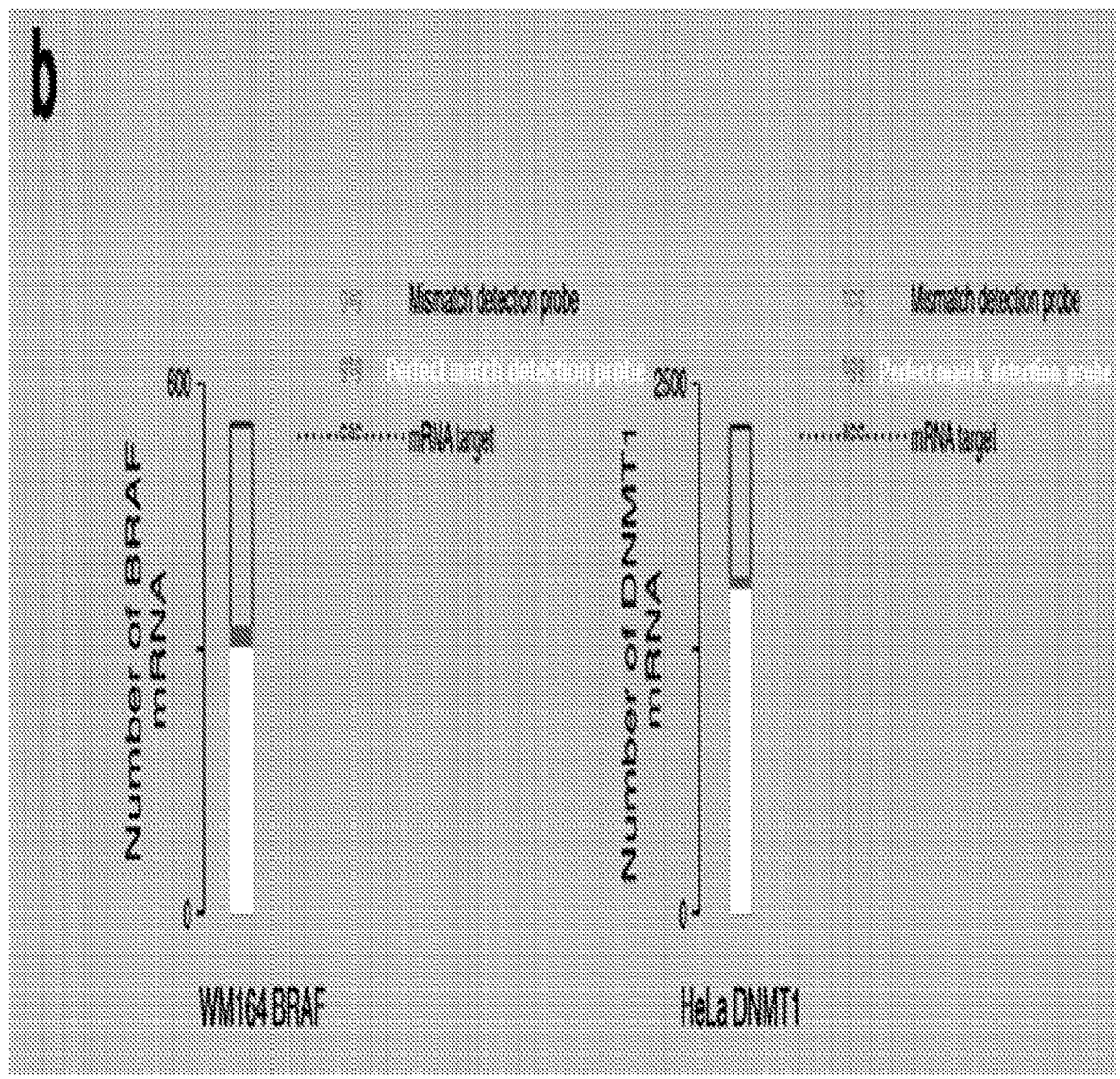

Single Cell Allele-Specific Expression Via Single Nucleotide Variant Detection in Situ To demonstrate the efficacy of the method of the present invention, a series of melanoma cell lines harboring a well-known mutation in the BRAF oncogene were utilized. Cell lines used were homozygous mutant, heterozygous mutant/wild-type and homozygous wild-type in a mutation of the 1799 position from T to A. Two detection probes were designed for this particular SNV, one targeting the mutant and one targeting wild-type transcripts. A mask oligonucleotide was utilized that was common to both. In the homozygous mutant cell line, it was found that roughly 56% of the RNA identified by the guide probe colocalized with signals from the mutant detection probe, whereas only 7% of the guide probe signals colocalized with the wild-type detection probe. Conversely, in the homozygous wild-type cell line, it was found that 58% of guide probe signals colocalized with the wild-type detection probe whereas only 7% of the guide probe signals colocalized with the mutant detection probe. In the heterozygous mutant/wild-type cell line, it was found that 36% of BRAF transcripts colocalized with the wild-type detection probe while 29% colocalized with the mutant detection probe, indicating that both copies of the genes transcribe equivalently in these cells. Overall, it was found that the colocalization efficiency was around 60%, roughly in line with other estimates of efficiency of hybridization of DNA oligonucleotides to RNA (Lubeck & Cai, 2012, Nat Methods 9:743-748). It was also found that the presence of the wild-type probe improves specificity of the mutant detection probe and vice-versa. The mask oligonucleotide is preferred for maintaining this specificity, as the number of false positive detections observed increased when detection was performed without the mask present (FIG. 4A). This approach works for a variety of different target sequence mismatches (FIG. 4B).

Figures 2A, 2B:
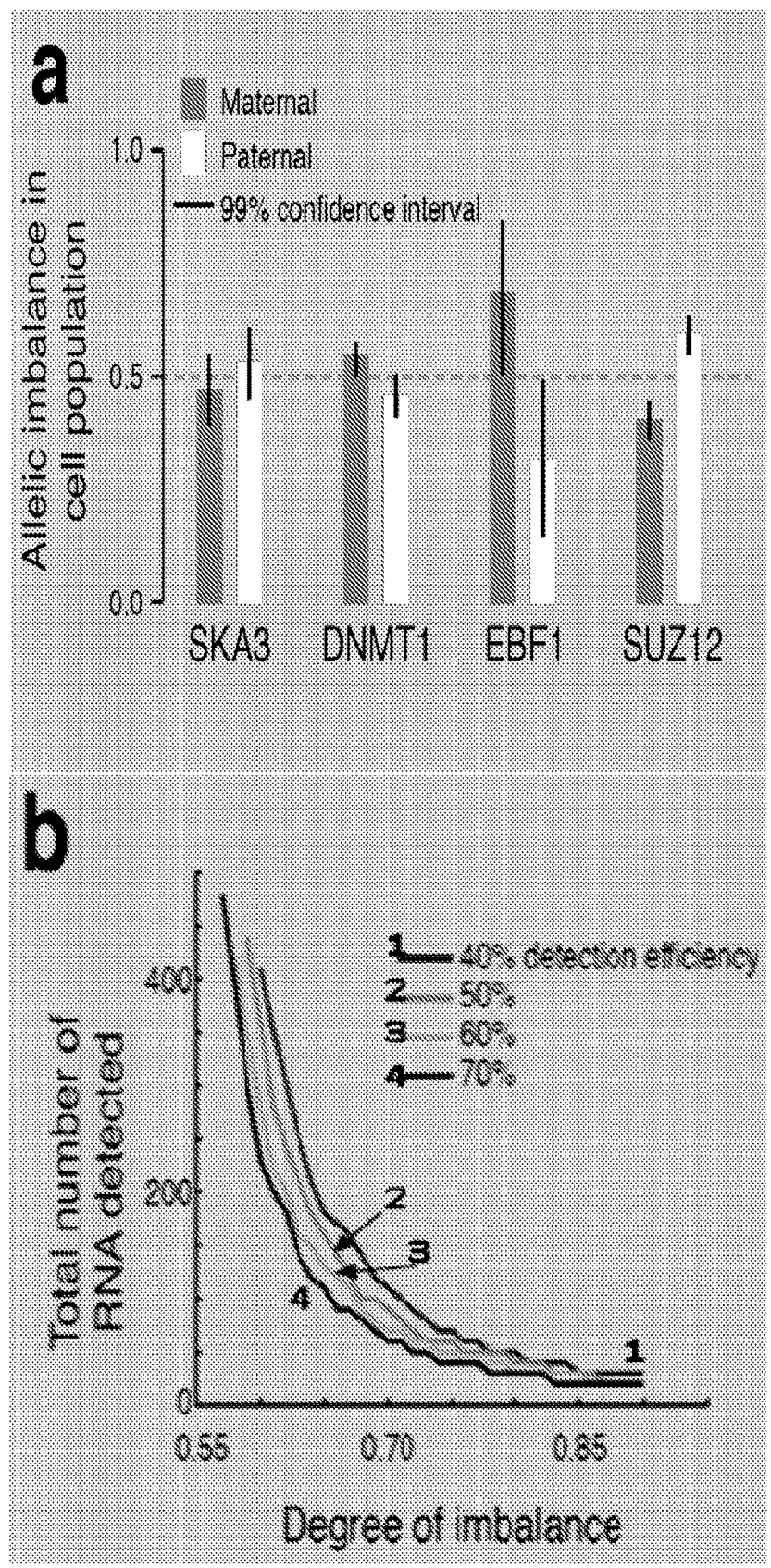
FIGS. 2A through 2C, is a set of diagrams and graphs, showing allele-specific expression at the population and single-cell level in GM12878 cells.

The method for detecting SNVs on RNA molecules provided the ability to measure differences in transcription from the maternal vs. paternal copy of a gene, both at the population and single cell level. This was explored using the GM12878 cell line, for which complete genetic phase information is available (1000 Genomes Project Consortium et al., 2010, Nature 467:1061-1073), making it ideal for studies involving allele-specific expression (Gertz et al., 2011, PLoS Genet 7:e1002228; Rozowsky et al., 2011, Mol Syst Biol 7:522). First, population-level imbalances were examined in maternal vs. paternal transcript abundance. It was found that two of the genes (SKA3 and DNMT1) displayed no imbalance, whereas EBF1 and SUZ12 favored transcription from the maternal and paternal chromosome, respectively (FIG. 2A). Through the use of a statistical model, the number of mRNAs that must be classified with this method in order to make the determination that an imbalance exits were computed (FIG. 2B). Strikingly, the ability to make this determination does not depend strongly on the detection efficiency of the SNV detection probes of this method (FIG. 2B).

Figure 2C:
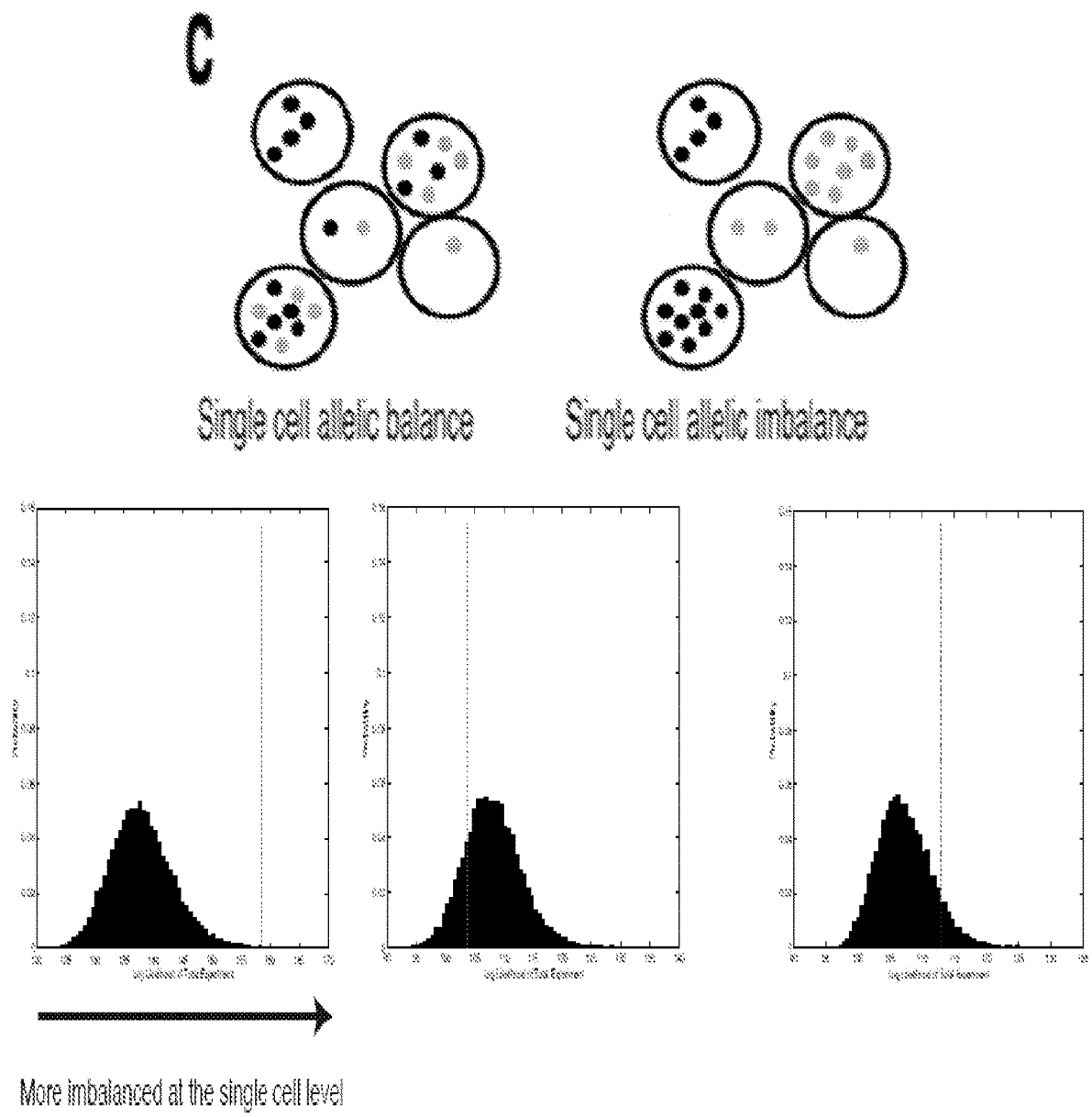
Figures 3A, 3B:
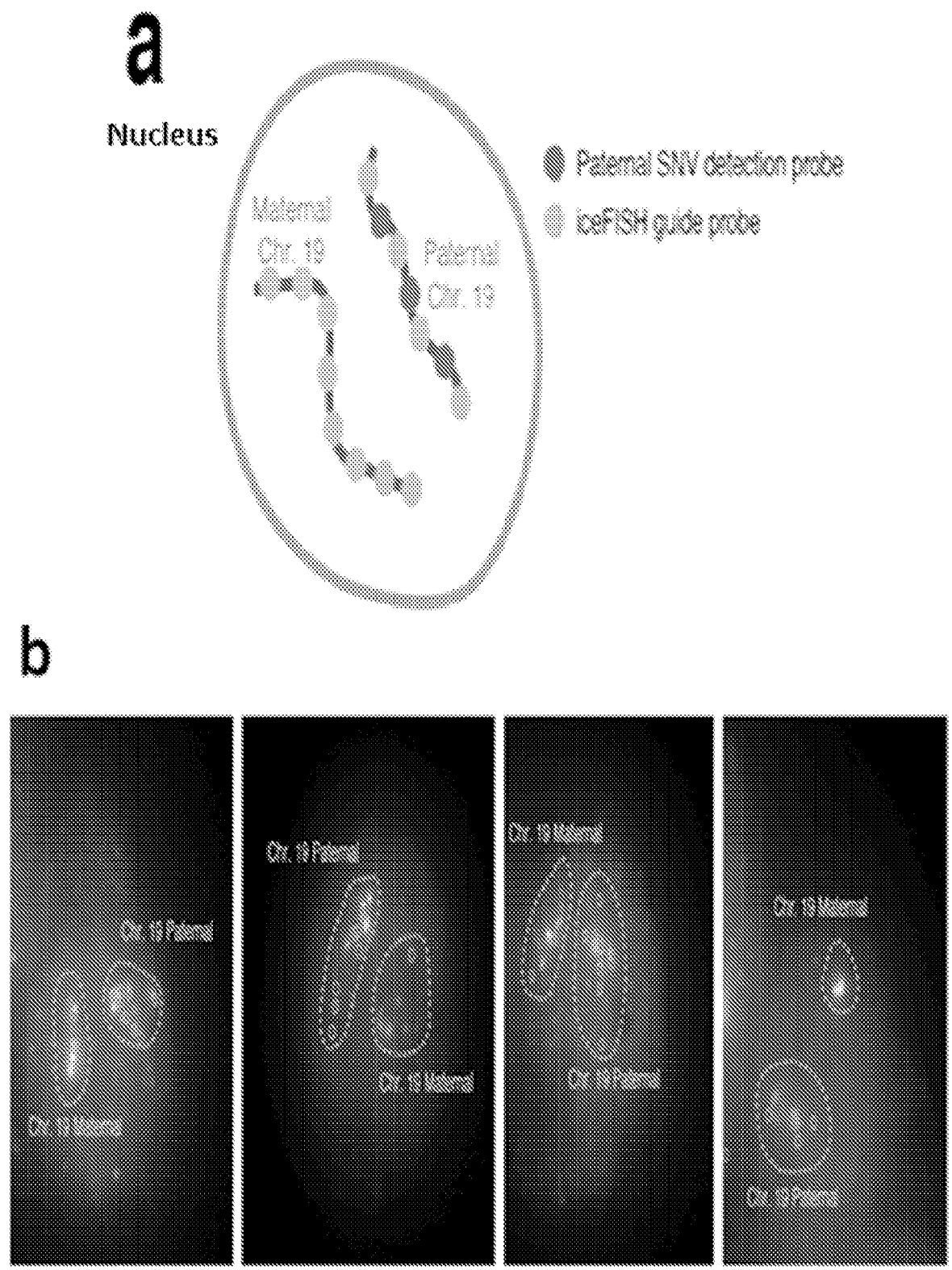
FIGS. 3A and 3B, is a set of images and diagrams showing the detection of maternal and paternal chromosomes in situ using SNV detection.

A search for single cell imbalances that may not be visible at the population level was then conducted (FIG. 2C). A statistical test was used to demonstrate whether the ensemble of individual cells displayed any signs of single cell imbalance.

Figure 5:
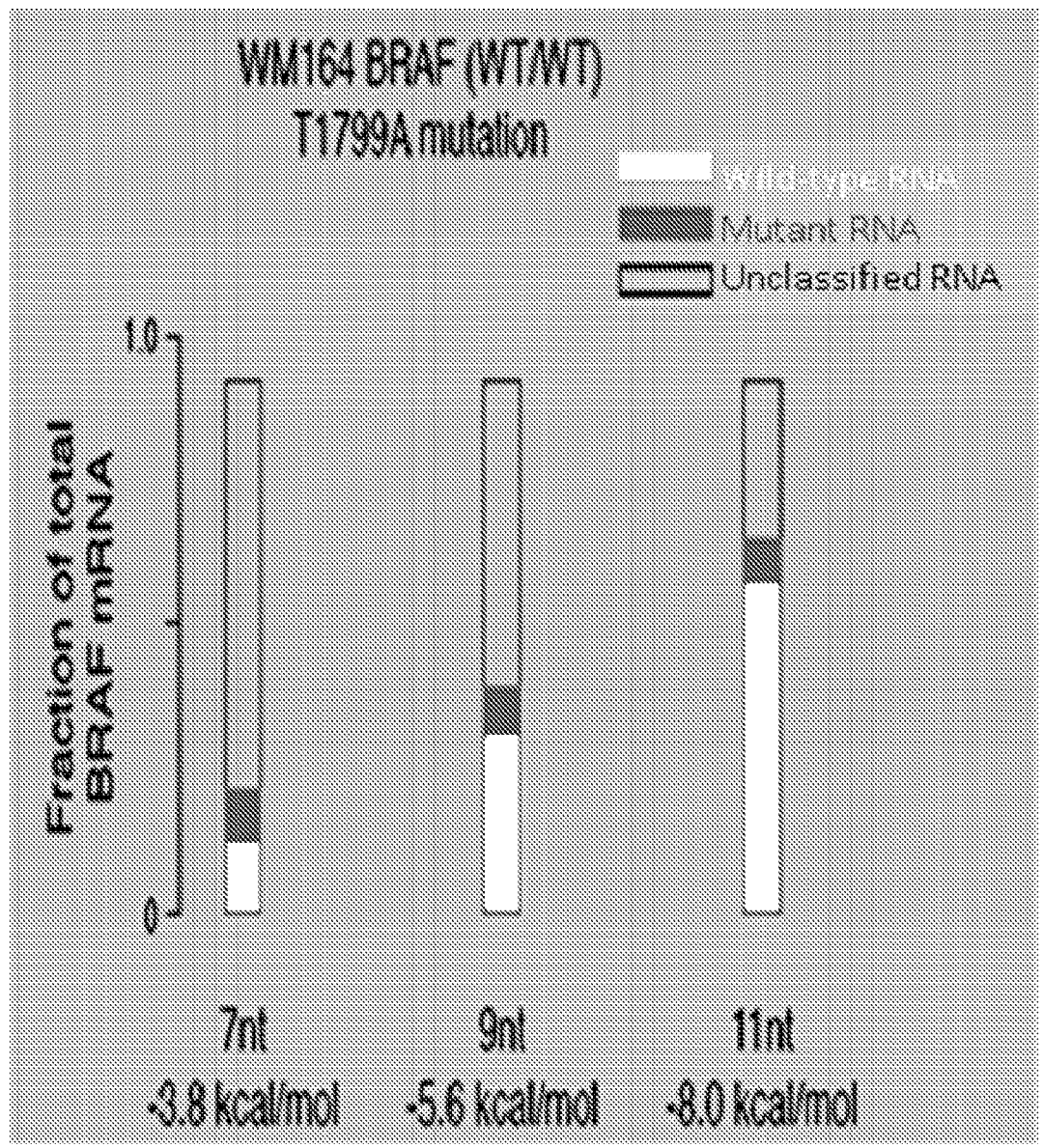
FIG. 5 is a graph showing that changing the toehold length can change the detection efficiency without dramatically increasing off-target binding. Toehold length is in nucleotides, with the total probe length remaining constant (toehold length changed by changing the mask probe length). The free energy change of the toehold binding (given in kcal/mol) was computed using parameters from Sugimoto et al. Biochemistry 34: 11211-11216 (1995).

To examine the effect of the toehold length on detection efficiency, the mask probe length was varied. As shown in FIG. 5, changing the toehold length can change the detection efficiency without dramatically increasing off-target binding. Toehold length is in nucleotides, with the total probe length remaining constant (toehold length changed by changing the mask probe length). The free energy change of the toehold binding (given in kcal/mol) was computed using parameters from Sugimoto et al. Biochemistry 34: 11211-11216 (1995).

Another application of the method is to distinguish transcription from the maternal vs. paternal chromosomes in situ. A set of probes were developed targeting introns of a set of 31 genes along chromosome 19, yielding an RNA-based chromosome "paint" (Levesque & Raj, 2013, Nat Methods, doi:10.1038/nmeth.2372). A database of SNVs in GM12878 cells was used to find SNVs in the introns of these genes and created a set of detection probes designed to label 15 of the introns from the paternal chromosomes in a distinct color. In this manner, chromosomes were visualized and classified as being either maternal or paternal in situ.

Accordingly, the ability to distinguish SNVs with high efficiency and specificity at the level of individual RNA molecules has been demonstrated. The method is simple to implement and uses readily available reagents. Without wishing to be bound by any particular theory, using different nucleic acid chemistries for the detection probe increases the detection efficiency. Among other applications, the method may be used to study the effects of SNVs on gene expression.

Cell Culture and Fixation

Melanoma cell lines were grown with the BRAF V600E mutation, SK-MEL-28 (Mut/Mut, ATCC #HTB-72), WM3918 (WT/WT) and WM398b & WM9 (both WT/Mut) (gifts from the lab of Meenhard Herlyn, Wistar Institute), using the recommended cell culture guidelines for each line. The cells were grown on Lab-Tek chambered coverglass (Lab-Tek) and fixed the cells following the protocol in Raj (Raj et al., 2008, Nat Methods 5:877-879). GM12878 cells were obtained from the Coriell Cell Repositories and were grown according to guidelines. Fixed cells were stored in 70% ethanol at 4° C. for up to 4 weeks before hybridization; the duration of storage did not affect hybridization efficiency.

Probe Design and Synthesis

Detection probes were designed with the single nucleotide difference located at the 5th base position from their 5' end. The total length of the detection oligonucleotide was adjusted to ensure the hybridization energy with target RNA was similar or greater than that of the guide probe oligonucleotides. Mask oligonucleotides complementary to the detection probes were designed that, upon binding to the detection probe, left a 5 to 11 base toehold regions available to target RNAs regions with SNVs. Guide probe oligonucleotides were conjugated to ATTO 488 dye (ATTO-TEC) and Cy3 and Cy5 (GE Healthcare) dyes were used interchangeably for the SNV detection probes. Changes to detection efficiency were not observed when swapping the Cy3/Cy5 dyes. The choice of dyes was influenced by dye stability after a post-fixation step described below and affinities of some dyes that cause excessive binding to the incorrect target. The detection, mask, and guide probe sequences are listed in Example 2 and Example 3.

RNA Fish

RNA fluorescence in situ hybridization (FISH) was performed as outlined in Raj (Raj et al., 2008, Nat Methods 5:877-879) with some modifications as outlined presently. Firstly, the hybridization buffer consisted of 10% dextran sulfate, 2× saline-sodium citrate (SSC) and 10% formamide (Lubeck & Cai, 2012, Nat Methods 9:743-748). The hybridization was performed as in Raj, using final concentrations of 5 nM for the guide probe, wild-type and mutant detection probe, and 10 nM for the mask, thereby leading to 1:1 mask:detection oligonucleotide ratios. The hybridization was allowed to proceed overnight at 37° C. For Lab-Tek chamber samples, 50 μL hybridization solution was used with a coverslip and included a moistened paper towel to prevent excessive evaporation in a para-filmed culture dish. For suspension cells, 50 uL hybridization solution was used in a 1.5 mL Eppendorf tube. In the morning, the samples were washed twice with a 2×SSC and 10% formamide wash buffer. Suspension cells included 0.1% Triton-X in the wash and fixation buffers. A postfixation step was then performed using 4% formaldehyde in 2×SSC for 30 minutes at 25° C. to crosslink the detection probes and thereby prevent dissociation during imaging, followed by 2 washes in 2×SSC. The cells were then put into anti-fade buffer with catalase and glucose oxidase as described (Raj et al., 2008, Nat Methods 5:877-879) to prevent photobleaching of Cy5 during imaging. For the chromosome 19 paints, probes against introns of 31 genes with 12-16 oligonucelotides per gene were used, each at 0.1 nM, for the guide probe in Cy3 (Levesque & Raj, 2013, Nat Methods, doi:10.1038/nmeth.2372). Maternal and paternal probes were added, in Cy3 and Cy5 respectively, for 19 SNV sites within 15 of the chromosome 19 paint genes, added masks, and performed hybridization as described elsewhere herein.

Imaging

All images were taken on a Leica DMI600B automated widefield fluorescence microscope equipped with a 100× Plan Apo objective, a Pixis 1024BR cooled CCD camera and a Prior Lumen 220 light source. Image stacks were taken in each fluorescence channel consisting of sets of images separated by 0.35 μm. The exposure times were 1500 ms and 3500 ms for guide and detection probes respectively. Longer exposure times were used for the wild-type and mutant detection probes owing to the low signal afforded by single dye molecules relative to the dozens of fluorophores typically used in the guide probes.

Image Analysis

The image analysis involved first manually segmenting the cells using custom software written in MATLAB (Mathworks), after which spots were identified using algorithms Relatively permissive thresholds were chosen for spots in the channels for the SNV detection probe channels, thereby trying to avoid false negatives due to overly stringent criteria for spot detection. Once the spots were located, spots were denoted as colocalized if two spots from different fluorescence channels were within 4 pixels of each other in order to account for a ~2 pixel chromatic aberration in portions of the images from the different channels. In the event of a colocalization event in which spots appeared in more than 2 channels or in which more than 2 spots were in the neighborhood of the guide probe, colocalized pairs in the rest of the image were used as a measure of how to correct for shifts between channels, thereby allowing the colocalization window to be tightened.

Example 2

Guide Probe Sequences

| Probe | Sequence | Identifier |
|---|---|---|
| SUZ12_mRNA_2 | gaggaaaagctcgtggtcag | SEQ ID NO: 1 |
| SUZ12_mRNA_3 | gatctgtgttggcttctcaa | SEQ ID NO: 2 |
| SUZ12_mRNA_4 | gagattccgagttcgaagaa | SEQ ID NO: 3 |
| SUZ12_mRNA_5 | tgtgcaaaaatattggtgct | SEQ ID NO: 4 |
| SUZ12_mRNA_6 | tctggagtttcgatgagaca | SEQ ID NO: 5 |
| SUZ12_mRNA_7 | tgagattcttgctctccttt | SEQ ID NO: 6 |
| SUZ12_mRNA_8 | ctgcaaatgagctgacaagc | SEQ ID NO: 7 |
| SUZ12_mRNA_9 | tggaagaaaccagtaaacgt | SEQ ID NO: 8 |
| SUZ12_mRNA_10 | aagagtgaactgcaacgtag | SEQ ID NO: 9 |
| SUZ12_mRNA_11 | gcaataggagccgtagattt | SEQ ID NO: 10 |
| SUZ12_mRNA_12 | atttctagtggcaagaggtt | SEQ ID NO: 11 |
| SUZ12_mRNA_13 | taactgaaccaggcttgttt | SEQ ID NO: 12 |
| SUZ12_mRNA_14 | acagcaatagtttgagtagg | SEQ ID NO: 13 |
| SUZ12_mRNA_15 | tgttgccttgtattgttgtt | SEQ ID NO: 14 |
| SUZ12_mRNA_16 | caggtcatctcttgcttcag | SEQ ID NO: 15 |
| SUZ12_mRNA_17 | tcagagtacaccaagggcaa | SEQ ID NO: 16 |
| SUZ12_mRNA_18 | aaactataaagtttgcggca | SEQ ID NO: 17 |
| SUZ12_mRNA_19 | tggcagagtttaagatgctt | SEQ ID NO: 18 |
| SUZ12_mRNA_20 | cctagcaccttttggatgat | SEQ ID NO: 19 |
| SUZ12_mRNA_21 | ggagccatcataacactcat | SEQ ID NO: 20 |
| SUZ12_mRNA_22 | tatcctgaggatttcctgca | SEQ ID NO: 21 |
| SUZ12_mRNA_23 | tgcgactaaaagcaaatcca | SEQ ID NO: 22 |
| SUZ12_mRNA_24 | ggtgttctcttaactggtcc | SEQ ID NO: 23 |
| SUZ12_mRNA_25 | gcctgcacacaagaatatgt | SEQ ID NO: 24 |
| SUZ12_mRNA_26 | catgcttgcttttgttcgtt | SEQ ID NO: 25 |

-continued

| Probe | Sequence | Identifier |
|---|---|---|
| SUZ12_mRNA_27 | ctttgctgttctacttcccc | SEQ ID NO: 26 |
| SUZ12_mRNA_28 | aaatacagacgattgtggcc | SEQ ID NO: 27 |
| SUZ12_mRNA_29 | agaggtaagcaggtatcact | SEQ ID NO: 28 |
| SUZ12_mRNA_30 | gacatggagattccagagtt | SEQ ID NO: 29 |
| SUZ12_mRNA_31 | cagcaataaacccatgcttc | SEQ ID NO: 30 |
| SUZ12_mRNA_32 | caggcatgattcatttgatt | SEQ ID NO: 31 |
| SUZ12_mRNA_33 | tgaagcatgaagtttcgaca | SEQ ID NO: 32 |
| SUZ12_mRNA_34 | aaagtcatgcatgctgacta | SEQ ID NO: 33 |
| SUZ12_mRNA_35 | catttcacggagcttggtaa | SEQ ID NO: 34 |
| SUZ12_mRNA_36 | tatttcttcgtttgcagggg | SEQ ID NO: 35 |
| SUZ12_mRNA_37 | ccatttgctgtcccattttg | SEQ ID NO: 36 |
| SUZ12_mRNA_38 | ctgttttgaaacccctgaga | SEQ ID NO: 37 |
| SUZ12_mRNA_39 | acatggggttagagcttttc | SEQ ID NO: 38 |
| SUZ12_mRNA_40 | agaggatgaattccctaaaa | SEQ ID NO: 39 |
| SUZ12_mRNA_41 | tgaagtagaaccctgataca | SEQ ID NO: 40 |
| SUZ12_mRNA_42 | cctccccaagaaaatgtctc | SEQ ID NO: 41 |
| SUZ12_mRNA_43 | aggatcaaagtttgactgca | SEQ ID NO: 42 |
| SUZ12_mRNA_44 | gggtgagcaatgcactaaaa | SEQ ID NO: 43 |
| SUZ12_mRNA_46 | caaatgcgttctttccttgg | SEQ ID NO: 44 |
| SUZ12_mRNA_47 | ttctcccettataagtgaca | SEQ ID NO: 45 |
| SUZ12_mRNA_49 | acacatataacacagggcaa | SEQ ID NO: 46 |
| SUZ12_mRNA_50 | caactgcaaatatgtgcgtg | SEQ ID NO: 47 |
| SUZ12_mRNA_51 | tgcttgttaatgtgccagta | SEQ ID NO: 48 |
| SUZ12_mRNA_52 | cggagttggaataaaaacct | SEQ ID NO: 49 |
| SUZ12_mRNA_53 | gatgttactcaaccacagtg | SEQ ID NO: 50 |
| SUZ12_mRNA_54 | acacatcttaaagaccagtc | SEQ ID NO: 51 |
| SUZ12_mRNA_55 | tcgttaaatagcctcacagt | SEQ ID NO: 52 |
| SUZ12_mRNA_56 | tgacaaatcacatccacact | SEQ ID NO: 53 |
| SUZ12_mRNA_57 | aatgaaagctgcagtttccc | SEQ ID NO: 54 |
| SUZ12_mRNA_58 | gcttaccaatcaaggaatct | SEQ ID NO: 55 |
| SUZ12_mRNA_59 | ccagaggcaaaaatcagagt | SEQ ID NO: 56 |
| SUZ12_mRNA_60 | cgagataaacgctcgagatc | SEQ ID NO: 57 |
| SUZ12_mRNA_61 | tatgtgcacagcttttagcaa | SEQ ID NO: 58 |
| SUZ12_mRNA_62 | ttctacacctacatctcccc | SEQ ID NO: 59 |
| SUZ12_mRNA_63 | agcattaagagcataactgc | SEQ ID NO: 60 |
| SUZ12_mRNA_64 | gcaaacaatgctagccttct | SEQ ID NO: 61 |
| SUZ12_mRNA_65 | ggtgggaatcaccaactttt | SEQ ID NO: 62 |
| DNMT1_mRNA_1 | gatacectgtgcagaaggat | SEQ ID NO: 63 |
| DNMT1_mRNA_2 | gatgtaccaaacggagagag | SEQ ID NO: 64 |
| DNMT1_mRNA_3 | cattcacttcccggttgtaa | SEQ ID NO: 65 |
| DNMT1_mRNA_4 | ttggttcccgttttctagac | SEQ ID NO: 66 |
| DNMT1_mRNA_5 | ctctacgggcttcacttctt | SEQ ID NO: 67 |
| DNMT1_mRNA_6 | gaggtttggaaaggggtttg | SEQ ID NO: 68 |
| DNMT1_mRNA_7 | ctggtcttttgtcttcttcct | SEQ ID NO: 69 |
| DNMT1_mRNA_8 | cgttctctggatgtaactct | SEQ ID NO: 70 |
| DNMT1_mRNA_9 | tttctcgtctccatcttcgt | SEQ ID NO: 71 |
| DNMT1_mRNA_10 | gttttgcgtctcttctcctc | SEQ ID NO: 72 |
| DNMT1_mRNA_11 | agttcatgactgttttggcg | SEQ ID NO: 73 |
| DNMT1_mRNA_12 | agcttctcatttgtcagcat | SEQ ID NO: 74 |
| DNMT1_mRNA_13 | gactcgttggcatcaaagat | SEQ ID NO: 75 |
| DNMT1_mRNA_14 | ctgaagcaggtcagtttgtg | SEQ ID NO: 76 |
| DNMT1_mRNA_15 | gtgaccgtgcttacagtaca | SEQ ID NO: 77 |
| DNMT1_mRNA_16 | tattcttctcgatgaggccg | SEQ ID NO: 78 |
| DNMT1_mRNA_18 | ctccatcaaagccagtgatc | SEQ ID NO: 79 |
| DNMT1_mRNA_19 | ccatcagaatgtattcggca | SEQ ID NO: 80 |
| DNMT1_mRNA_20 | caaatatgggcgcatactcg | SEQ ID NO: 81 |
| DNMT1_mRNA_21 | tcataggtcgagtcggaatt | SEQ ID NO: 82 |
| DNMT1_mRNA_22 | ctcgatcttgttgatcaggt | SEQ ID NO: 83 |
| DNMT1_mRNA_23 | gttcaagttgaggccagaag | SEQ ID NO: 84 |
| DNMT1_mRNA_24 | ctcgtcataactctccacct | SEQ ID NO: 85 |
| DNMT1_mRNA_25 | gtagaatgcctgatggtctg | SEQ ID NO: 86 |
| DNMT1_mRNA_26 | cctttcaatttgctctgcg | SEQ ID NO: 87 |
| DNMT1_mRNA_27 | cttaaaggcgttctccttgt | SEQ ID NO: 88 |
| DNMT1_mRNA_28 | tccactgccaccaaatttaa | SEQ ID NO: 89 |
| DNMT1_mRNA_29 | cttcatggccatattgggac | SEQ ID NO: 90 |
| DNMT1_mRNA_30 | gacttcctcatcgtcatctg | SEQ ID NO: 91 |
| DNMT1_mRNA_31 | ggcatctctgggatgttatc | SEQ ID NO: 92 |
| DNMT1_mRNA_32 | cttctccgacccaagagatg | SEQ ID NO: 93 |
| BRAF_mRNA_2 | ttgatattccacacctcctc | SEQ ID NO: 94 |
| BRAF_mRNA_3 | tgtccaatagggcctctata | SEQ ID NO: 95 |
| BRAF_mRNA_5 | gctggtgtattcttcatagg | SEQ ID NO: 96 |
| BRAF_mRNA_6 | tctttgttggagtgcatcta | SEQ ID NO: 97 |
| BRAF_mRNA_7 | gttccccagagattccaata | SEQ ID NO: 98 |
| BRAF_mRNA_8 | gtatccattgatgcagagct | SEQ ID NO: 99 |
| BRAF_mRNA_9 | ttgttgggcaggaagactct | SEQ ID NO: 100 |
| BRAF_mRNA_10 | actgtaactccacaccttgc | SEQ ID NO: 101 |
| BRAF_mRNA_11 | agtgctttcttttagactgtc | SEQ ID NO: 102 |
| BRAF_mRNA_12 | ttctctccatcctgaattct | SEQ ID NO: 103 |

| Probe | Sequence | Identifier |
|---|---|---|
| BRAF_mRNA_13 | agtgtcccaaccaattggtt | SEQ ID NO: 104 |
| BRAF_mRNA_14 | tccacatgcaattcttctcc | SEQ ID NO: 105 |
| BRAF_mRNA_15 | tggtattgggtggtgttcaa | SEQ ID NO: 106 |
| BRAF_mRNA_16 | cttcatctgctggtcggaag | SEQ ID NO: 107 |
| BRAF_mRNA_18 | ggggtagcagacaaacctgt | SEQ ID NO: 108 |
| BRAF_mRNA_19 | tcacgttagttagtgagcca | SEQ ID NO: 109 |
| BRAF_mRNA_20 | tgaggtcctggagatttctg | SEQ ID NO: 110 |
| BRAF_mRNA_21 | attcctgtcttctgaggatg | SEQ ID NO: 111 |
| BRAF_mRNA_22 | ctcccaatcatcactcgagt | SEQ ID NO: 112 |
| BRAF_mRNA_23 | tctttgtcccactgtaatct | SEQ ID NO: 113 |
| BRAF_mRNA_24 | ttcactgccacatcaccatg | SEQ ID NO: 114 |
| BRAF_mRNA_25 | gtaggtgctgtcacattcaa | SEQ ID NO: 115 |
| BRAF_mRNA_26 | tcacatgtcgtgttttcctg | SEQ ID NO: 116 |
| BRAF_mRNA_27 | caatagccagttgtggcttt | SEQ ID NO: 117 |
| BRAF_mRNA_28 | tggtgatacaagctggagcc | SEQ ID NO: 118 |
| BRAF_mRNA_32 | gcattctgatgacttctggt | SEQ ID NO: 119 |
| BRAF_mRNA_33 | tccctgttgttgatgtttga | SEQ ID NO: 120 |
| BRAF_mRNA_34 | gcttttggacagttactccg | SEQ ID NO: 121 |
| BRAF_mRNA_35 | tcaaggagggttctgatgca | SEQ ID NO: 122 |
| BRAF_mRNA_36 | tcctctgtttggaaaccagc | SEQ ID NO: 123 |
| BRAF_mRNA_37 | tcctgaactctctcactcat | SEQ ID NO: 124 |
| BRAF_mRNA_38 | aagcctctagaagaggctct | SEQ ID NO: 125 |
| BRAF_mRNA_40 | atctgttcagtttgccttat | SEQ ID NO: 126 |
| SKA3_mRNA_1 | atcttcaaagtcgctttcct | SEQ ID NO: 127 |
| SKA3_mRNA_2 | catcatcctttagagtctga | SEQ ID NO: 128 |
| SKA3_mRNA_3 | ccttcttgatttttccaatct | SEQ ID NO: 129 |
| SKA3_mRNA_4 | gtacttttgttgcctttatg | SEQ ID NO: 130 |
| SKA3_mRNA_5 | gacacgtggactatatccat | SEQ ID NO: 131 |
| SKA3_mRNA_6 | tcttgctcgtgtactgaatt | SEQ ID NO: 132 |
| SKA3_mRNA_7 | ctctgggtcagagttaatgg | SEQ ID NO: 133 |
| SKA3_mRNA_8 | atctttcacatcagtcttct | SEQ ID NO: 134 |
| SKA3_mRNA_9 | cttgcaacaggaggatcaga | SEQ ID NO: 135 |
| SKA3_mRNA_10 | actacgtggagacttctcag | SEQ ID NO: 136 |
| SKA3_mRNA_11 | tgtggagggtttggtagaac | SEQ ID NO: 137 |
| SKA3_mRNA_12 | ctcttccttatagttgttca | SEQ ID NO: 138 |
| SKA3_mRNA_13 | agtgattgtttggtaggtgg | SEQ ID NO: 139 |
| SKA3_mRNA_14 | gtgcacattttggagttttt | SEQ ID NO: 140 |
| SKA3_mRNA_15 | tcccattgtgtaatcttcat | SEQ ID NO: 141 |
| SKA3_mRNA_16 | cctcactttattattcctc | SEQ ID NO: 142 |
| SKA3_mRNA_17 | ctggattctgtatctatggc | SEQ ID NO: 143 |
| SKA3_mRNA_18 | gctgggagtggcaaaaacat | SEQ ID NO: 144 |
| SKA3_mRNA_19 | ccaggagtacagaatgtagg | SEQ ID NO: 145 |
| SKA3_mRNA_20 | gtggataccaaagctatgct | SEQ ID NO: 146 |
| SKA3_mRNA_21 | agtacgatcttcaacttcca | SEQ ID NO: 147 |
| SKA3_mRNA_22 | cgtaggtgaagagggatctg | SEQ ID NO: 148 |
| SKA3_mRNA_23 | gcagggcaatgtgaatgtta | SEQ ID NO: 149 |
| SKA3_mRNA_24 | ggtcaacgtttaaaggggga | SEQ ID NO: 150 |
| SKA3_mRNA_25 | atgactgggctacatgtcaa | SEQ ID NO: 151 |
| SKA3_mRNA_26 | ctacttcctggtactactta | SEQ ID NO: 152 |
| SKA3_mRNA_27 | cagacagcactgagcaagta | SEQ ID NO: 153 |
| SKA3_mRNA_28 | ctccaatggtcacagtatat | SEQ ID NO: 154 |
| SKA3_mRNA_29 | aactctcaacctgacagcag | SEQ ID NO: 155 |
| SKA3_mRNA_30 | aagagaaaagacccccacac | SEQ ID NO: 156 |
| SKA3_mRNA_31 | cagctgccatgtgatagaaa | SEQ ID NO: 157 |
| SKA3_mRNA_32 | aaattcagggtctactgggt | SEQ ID NO: 158 |
| SKA3_mRNA_33 | catagctaacagtgcacagg | SEQ ID NO: 159 |
| SKA3_mRNA_34 | taagcaggtcaacctgaagc | SEQ ID NO: 160 |
| SKA3_mRNA_35 | aatcagaaggatcgtaggcc | SEQ ID NO: 161 |
| SKA3_mRNA_36 | cggtacacagtgaaaggctg | SEQ ID NO: 162 |
| EBF1_mRNA_1 | ctctgctcaaaactgagcga | SEQ ID NO: 163 |
| EBF1_mRNA_2 | aagttggatttccgcagatt | SEQ ID NO: 164 |
| EBF1_mRNA_3 | tattggtcttttcgctgttg | SEQ ID NO: 165 |
| EBF1_mRNA_4 | tatcccattgctgtagagaa | SEQ ID NO: 166 |
| EBF1_mRNA_5 | tcaatgaggcgcacgtagaa | SEQ ID NO: 167 |
| EBF1_mRNA_6 | acactatggcttgttttgtc | SEQ ID NO: 168 |
| EBF1_mRNA_7 | caagactcggcacatttctg | SEQ ID NO: 169 |
| EBF1_mRNA_8 | ttttcttgtcacaacagcgg | SEQ ID NO: 170 |
| EBF1_mRNA_9 | atctgagggagtctcatttc | SEQ ID NO: 171 |
| EBF1_mRNA_10 | tgatggctttgatacaggga | SEQ ID NO: 172 |
| EBF1_mRNA_12 | aatgaccttctgtaacctct | SEQ ID NO: 173 |
| EBF1_mRNA_13 | tgagtattacttcctttggc | SEQ ID NO: 174 |
| EBF1_mRNA_14 | atacagtgcttctaccagat | SEQ ID NO: 175 |
| EBF1_mRNA_15 | tccactgaacgaattcacgc | SEQ ID NO: 176 |
| EBF1_mRNA_16 | gagttatagttggtctgctg | SEQ ID NO: 177 |
| EBF1_mRNA_17 | aattggacattgcggcagag | SEQ ID NO: 178 |
| EBF1_mRNA_18 | ggtgagaaggagaagatgcc | SEQ ID NO: 179 |
| EBF1_mRNA_19 | tctgacgactggtgcgaaag | SEQ ID NO: 180 |
| EBF1_mRNA_20 | acaatcatgccagatatcgc | SEQ ID NO: 181 |

| Probe | Sequence | Identifier |
|---|---|---|
| EBF1_mRNA_21 | ctctgggacttgtatcagat | SEQ ID NO: 182 |
| EBF1_mRNA_22 | cctcttaaaaaggcctgagt | SEQ ID NO: 183 |
| EBF1_mRNA_23 | ccttgtatagagctttacgg | SEQ ID NO: 184 |
| EBF1_mRNA_24 | tcttcctttacacagcttta | SEQ ID NO: 185 |
| EBF1_mRNA_25 | tttaaggcgcaaaagccgac | SEQ ID NO: 186 |
| EBF1_mRNA_26 | taaggggtggcatgttaagt | SEQ ID NO: 187 |
| EBF1_mRNA_27 | acatcgcgttttaactttcc | SEQ ID NO: 188 |
| EBF1_mRNA_28 | tagaggcactggattttcga | SEQ ID NO: 189 |
| EBF1_mRNA_29 | cagagtgtggaattctgtgc | SEQ ID NO: 190 |
| EBF1_mRNA_30 | gtgaggttttggcttgttaa | SEQ ID NO: 191 |
| EBF1_mRNA_31 | gtctgcatttaggacgagta | SEQ ID NO: 192 |
| EBF1_mRNA_32 | cgaaaatacctgccacgttg | SEQ ID NO: 193 |
| EBF1_mRNA_33 | ctgatagaggcagtatctgg | SEQ ID NO: 194 |
| EBF1_mRNA_34 | cccttta actcttaattcca | SEQ ID NO: 195 |
| EBF1_mRNA_35 | aaatgcatcctcagagcttt | SEQ ID NO: 196 |
| EBF1_mRNA_36 | cgcacttttcacgtagcaaa | SEQ ID NO: 197 |
| EBF1_mRNA_37 | tccaagggagagattccat | SEQ ID NO: 198 |
| EBF1_mRNA_38 | ctatgaagtttctccctaga | SEQ ID NO: 199 |
| EBF1_mRNA_39 | tgcattgttaaggcatccaa | SEQ ID NO: 200 |
| EBF1_mRNA_40 | ctggtgcacagttacaatgt | SEQ ID NO: 201 |
| EBF1_mRNA_41 | agcctagtgaaaaccattgc | SEQ ID NO: 202 |
| EBF1_mRNA_42 | tttctgagtaccgagaagca | SEQ ID NO: 203 |
| EBF1_mRNA_43 | tgacagatgggtagtgtctg | SEQ ID NO: 204 |
| EBF1_mRNA_44 | agttctaaccactgcacatg | SEQ ID NO: 205 |
| EBF1_mRNA_45 | aggctctttggactttcaag | SEQ ID NO: 206 |
| EBF1_mRNA_46 | agtcatccagaagctgtatt | SEQ ID NO: 207 |
| EBF1_mRNA_47 | ttaagctgcatcctagtaca | SEQ ID NO: 208 |
| EBF1_mRNA_48 | gaactgtacagtgtgtgtct | SEQ ID NO: 209 |
| DHPS_int_1 | ctagtaccgcgttggttcta | SEQ ID NO: 210 |
| DHPS_int_2 | cagagtgcaaaatcccttc | SEQ ID NO: 211 |
| DHPS_int_3 | taccgtaccagcatgtaact | SEQ ID NO: 212 |
| DHPS_int_4 | cacaccaagaatcagtcctc | SEQ ID NO: 213 |
| DHPS_int_5 | gcccattccagaaagcttta | SEQ ID NO: 214 |
| DHPS_int_6 | cctcccatatcctcccttaa | SEQ ID NO: 215 |
| DHPS_int_7 | tctaaattcaagaaccgccc | SEQ ID NO: 216 |
| DHPS_int_8 | atctccttcagatccggtc | SEQ ID NO: 217 |
| DHPS_int_9 | ggctccagaaacagatttca | SEQ ID NO: 218 |
| DHPS_int_10 | taaatcccagactcaggact | SEQ ID NO: 219 |
| DHPS_int_11 | aagggccaagtcaagttaag | SEQ ID NO: 220 |
| DHPS_int_12 | ataactgcattgcccattga | SEQ ID NO: 221 |
| DHPS_int_13 | tgactcttatgagggagctc | SEQ ID NO: 222 |
| DHPS_int_14 | agtgaatttggcccaagaag | SEQ ID NO: 223 |
| DHPS_int_15 | cagagatagtctgggaggag | SEQ ID NO: 224 |
| DHPS_int_16 | gctaagtgttgcctctactg | SEQ ID NO: 225 |
| DNMT1_int_1 | gaatccacggtccattttgg | SEQ ID NO: 226 |
| DNMT1_int_2 | cttgctgtatttgggatca | SEQ ID NO: 227 |
| DNMT1_int_3 | catcgagatgcacagctttg | SEQ ID NO: 228 |
| DNMT1_int_4 | gtgacatccgtctctggagg | SEQ ID NO: 229 |
| DNMT1_int_5 | aaggagcaagaaccacacag | SEQ ID NO: 230 |
| DNMT1_int_6 | aatgcacggttaaagttcct | SEQ ID NO: 231 |
| DNMT1_int_7 | caggcacagatttacaggaa | SEQ ID NO: 232 |
| DNMT1_int_8 | agccagttctcattagcaag | SEQ ID NO: 233 |
| DNMT1_int_9 | acacactaaagaacacaccc | SEQ ID NO: 234 |
| DNMT1_int_10 | gatccttgtgcacggaagtt | SEQ ID NO: 235 |
| DNMT1_int_11 | aatgaactgatggcgttcat | SEQ ID NO: 236 |
| DNMT1_int_12 | cacacctcacttgaacaagt | SEQ ID NO: 237 |
| DNMT1_int_13 | gtgagggttcctctgactca | SEQ ID NO: 238 |
| DNMT1_int_14 | tttcacaaatccagctggaa | SEQ ID NO: 239 |
| DNMT1_int_15 | cccaaagacccaaatcagaa | SEQ ID NO: 240 |
| DNMT1_int_16 | ggggttgaaccaaatatcca | SEQ ID NO: 241 |
| EGLN2_int_1 | aactgcctaaaccttctgtg | SEQ ID NO: 242 |
| EGLN2_int_2 | gtccccacaagtaagcatac | SEQ ID NO: 243 |
| EGLN2_int_3 | atcaggtgcacacattaagg | SEQ ID NO: 244 |
| EGLN2_int_5 | gaatgtcagcagctctcatg | SEQ ID NO: 245 |
| EGLN2_int_7 | gatggactagaaacatgggc | SEQ ID NO: 246 |
| EGLN2_int_8 | ccacccatgaagacaatgat | SEQ ID NO: 247 |
| EGLN2_int_9 | cagaagcagaacccaagatg | SEQ ID NO: 248 |
| EGLN2_int_10 | gctcagctatcaagtaacgg | SEQ ID NO: 249 |
| EGLN2_int_11 | gtattccgtggatcagcaaa | SEQ ID NO: 250 |
| EGLN2_int_12 | gtccccaaccacatagaaag | SEQ ID NO: 251 |
| EGLN2_int_13 | tccttacttccctaggacaa | SEQ ID NO: 252 |
| EGLN2_int_14 | cccatctaaaagcgggaaag | SEQ ID NO: 253 |
| EGLN2_int_15 | gagtacaggagagagtccag | SEQ ID NO: 254 |
| EGLN2_int_16 | cagaacgactaagaagcacg | SEQ ID NO: 255 |
| EIF3K_int_1 | gattctctcgcttctaggcc | SEQ ID NO: 256 |
| EIF3K_int_2 | cgaagagactgagtggtacc | SEQ ID NO: 257 |
| EIF3K_int_3 | aaggaaaccttaaggcaatt | SEQ ID NO: 258 |
| EIF3K_int_4 | atgtccacctgaacactctg | SEQ ID NO: 259 |

-continued

| Probe | Sequence | Identifier |
|---|---|---|
| EIF3K_int_5 | tcctgaatgtctctgctact | SEQ ID NO: 260 |
| EIF3K_int_6 | tcagtcactgcagcttgtac | SEQ ID NO: 261 |
| EIF3K_int_7 | taggatgcctcctcaacctc | SEQ ID NO: 262 |
| EIF3K_int_8 | aagctctaaactccactgga | SEQ ID NO: 263 |
| EIF3K_int_9 | ttcttatcccagacctctcg | SEQ ID NO: 264 |
| EIF3K_int_10 | gctctatccaggtagtgaat | SEQ ID NO: 265 |
| EIF3K_int_11 | cagccaccttatggagcaag | SEQ ID NO: 266 |
| EIF3K_int_12 | agacagagagctagacactt | SEQ ID NO: 267 |
| EIF3K_int_13 | ctagttgctgcaatgggagt | SEQ ID NO: 268 |
| EIF3K_int_14 | gctgcattgttcaggatact | SEQ ID NO: 269 |
| EIF3K_int_15 | ctagtcttgcacaccaagag | SEQ ID NO: 270 |
| FBL_int_1 | gacctgctggaatcagaatc | SEQ ID NO: 271 |
| FBL_int_2 | cctattagacggcctcaatg | SEQ ID NO: 272 |
| FBL_int_3 | ctcctgcccaatatccaaaa | SEQ ID NO: 273 |
| FBL_int_4 | cagatgcctgaatccaaact | SEQ ID NO: 274 |
| FBL_int_5 | caagcctgattcccaaaaca | SEQ ID NO: 275 |
| FBL_int_6 | ggtggaaatcttaatccca | SEQ ID NO: 276 |
| FBL_int_7 | cgagcttgttaagtctcgtc | SEQ ID NO: 277 |
| FBL_int_8 | gagtggtttcagcagaatct | SEQ ID NO: 278 |
| FBL_int_9 | accaccgagaaggattctaa | SEQ ID NO: 279 |
| FBL_int_10 | ttctcacacagatgagtgcg | SEQ ID NO: 280 |
| FBL_int_11 | taggaaaacagaccctttgg | SEQ ID NO: 281 |
| FBL_int_12 | tcaagagatccccaaacacg | SEQ ID NO: 282 |
| FBL_int_13 | atcacagaccagaatgcctg | SEQ ID NO: 283 |
| FBL_int_14 | cattctaccacacatggagg | SEQ ID NO: 284 |
| FBL_int_15 | gagctaacacctgacaactt | SEQ ID NO: 285 |
| FBL_int_16 | ctcactcaggctaaaatcct | SEQ ID NO: 286 |
| MARK4_int_1 | gaccttgaagaagccagaaa | SEQ ID NO: 287 |
| MARK4_int_2 | cctgaagctgagaagttgat | SEQ ID NO: 288 |
| MARK4_int_3 | caagggaaaagggcttaaaa | SEQ ID NO: 289 |
| MARK4_int_4 | gagaaagcttccagcagatt | SEQ ID NO: 290 |
| MARK4_int_5 | aggtcaaggggtctagaaat | SEQ ID NO: 291 |
| MARK4_int_6 | agatgaataaaggctgagcc | SEQ ID NO: 292 |
| MARK4_int_7 | ctggaagtatggggtaggaa | SEQ ID NO: 293 |
| MARK4_int_8 | tcctaggaatcagagaaggg | SEQ ID NO: 294 |
| MARK4_int_9 | ggaatggtggaaagtgacaa | SEQ ID NO: 295 |
| MARK4_int_10 | tgatcagagacacaggagat | SEQ ID NO: 296 |
| MARK4_int_11 | gcaggtctttggaagtgatc | SEQ ID NO: 297 |
| MARK4_int_12 | tggggagaagtctaggattg | SEQ ID NO: 298 |
| MARK4_int_13 | gatctgcaagatgaggaagg | SEQ ID NO: 299 |
| MARK4_int_14 | actccaaattggagttctgg | SEQ ID NO: 300 |
| MARK4_int_15 | attgtagtgaccaaggaaca | SEQ ID NO: 301 |
| MARK4_int_16 | nctgaatcgagtaagccttgg | SEQ ID NO: 302 |
| PPP2R1A_int_1 | caaccggggagataagagac | SEQ ID NO: 303 |
| PPP2R1A_int_2 | cctacttggagcaagtcatg | SEQ ID NO: 304 |
| PPP2R1A_int_3 | aattaggatggcaggccttc | SEQ ID NO: 305 |
| PPP2R1A_int_4 | aaaatgagaggcggaggaag | SEQ ID NO: 306 |
| PPP2R1A_int_5 | cgtcctcttaggacacctaa | SEQ ID NO: 307 |
| PPP2R1A_int_6 | gctcctaaacttggctagtc | SEQ ID NO: 308 |
| PPP2R1A_int_7 | tatcctggtcaatgggagga | SEQ ID NO: 309 |
| PPP2R1A_int_8 | gcttagcaaatccctcaacc | SEQ ID NO: 310 |
| PPP2R1A_int_9 | catcccataaccaggaatgt | SEQ ID NO: 311 |
| PPP2R1A_int_10 | cctctttaatcaccactccc | SEQ ID NO: 312 |
| PPP2R1A_int_11 | aacagacctaaagggaggat | SEQ ID NO: 313 |
| PPP2R1A_int_12 | gtttggcaggttacccagtg | SEQ ID NO: 314 |
| PPP2R1A_int_13 | tataccaggaacctaggagg | SEQ ID NO: 315 |
| PPP2R1A_int_14 | tccccagcatcatatctcat | SEQ ID NO: 316 |
| PPP2R1A_int_15 | tatagcaactggtgtctcca | SEQ ID NO: 317 |
| PPP2R1A_int_16 | cctgtttcacatctggatcc | SEQ ID NO: 318 |
| PTBP1_int_1 | gaatgcgaaacatctccagc | SEQ ID NO: 319 |
| PTBP1_int_2 | aaacttctcaggaaaacgga | SEQ ID NO: 320 |
| PTBP1_int_3 | ctcttctgacaccacagact | SEQ ID NO: 321 |
| PTBP1_int_5 | gaacacagcctcagttactg | SEQ ID NO: 322 |
| PTBP1_int_6 | ctgaaactggcaaactcaca | SEQ ID NO: 323 |
| PTBP1_int_7 | gtgctttccagtaagttgga | SEQ ID NO: 324 |
| PTBP1_int_8 | cacgttccaagacaaagaca | SEQ ID NO: 325 |
| PTBP1_int_9 | ccacttgactgcaacttgaa | SEQ ID NO: 326 |
| PTBP1_int_10 | cgctagagaaagctcagaag | SEQ ID NO: 327 |
| PTBP1_int_11 | cggagaagcaaagtgagaag | SEQ ID NO: 328 |
| PTBP1_int_12 | aactccagattccagaccaa | SEQ ID NO: 329 |
| PTBP1_int_13 | tgacagcaagaaccgaagag | SEQ ID NO: 330 |
| PTBP1_int_14 | taggctggattctatccagg | SEQ ID NO: 331 |
| PTBP1_int_15 | tcaaccagtaaatgcccatc | SEQ ID NO: 332 |
| PTBP1_int_16 | ccctttcctcacatgctgag | SEQ ID NO: 333 |
| RPL18A_int_1 | gttgggtgcaacaagagaag | SEQ ID NO: 334 |
| RPL18A_int_2 | ctatgctgcgcgacttattc | SEQ ID NO: 335 |
| RPL18A_int_3 | tttcatctgcttctcacagc | SEQ ID NO: 336 |
| RPL18A_int_4 | tatgtaccacagcgttaagc | SEQ ID NO: 337 |

| Probe | Sequence | Identifier |
|---|---|---|
| RPL18A_int_5 | ccatagagccgtttgattct | SEQ ID NO: 338 |
| RPL18A_int_6 | agtccaggttctcctatctc | SEQ ID NO: 339 |
| RPL18A_int_7 | agctggagatctggacataa | SEQ ID NO: 340 |
| RPL18A_int_8 | cctttgacagcaaggaaacc | SEQ ID NO: 341 |
| RPL18A_int_9 | gttcaggaagggaacaatgg | SEQ ID NO: 342 |
| RPL18A_int_10 | ttttactgtgaacctgaccc | SEQ ID NO: 343 |
| RPL18A_int_11 | aaaccacctctgaaactgac | SEQ ID NO: 344 |
| RPL18A_int_12 | aatctttggtcaagtccagg | SEQ ID NO: 345 |
| RPL18A_int_13 | ggtttacagatgcagaggtg | SEQ ID NO: 346 |
| RPL18A_int_14 | aactgcaatccaaacgtttg | SEQ ID NO: 347 |
| RPL18A_int_15 | agaactaggacaagacctca | SEQ ID NO: 348 |
| RPL18A_int_16 | catcttctttcaccctgagg | SEQ ID NO: 349 |
| RPS19_int_1 | tctggatcgcactaacagag | SEQ ID NO: 350 |
| RPS19_int_2 | catcctaaaccgtggtaccc | SEQ ID NO: 351 |
| RPS19_int_3 | ggagaaagtcaagcatgtga | SEQ ID NO: 352 |
| RPS19_int_4 | tttgaacctcagtccccaaa | SEQ ID NO: 353 |
| RPS19_int_5 | gtacaaagagaggctggaac | SEQ ID NO: 354 |
| RPS19_int_6 | cctcaacacaactatgctgt | SEQ ID NO: 355 |
| RPS19_int_7 | ctaccccatatcccaaatgc | SEQ ID NO: 356 |
| RPS19_int_8 | cacgattcagtcatctccac | SEQ ID NO: 357 |
| RPS19_int_10 | gaagtatggtttgtgccagg | SEQ ID NO: 358 |
| RPS19_int_12 | caagtggtgacacaaccaag | SEQ ID NO: 359 |
| RPS19_int_13 | tcgaatgtcacatcacacaa | SEQ ID NO: 360 |
| RPS19_int_14 | aaaaacttggagtaccaagt | SEQ ID NO: 361 |
| RPS19_int_15 | ttcatctgtctctggtttcc | SEQ ID NO: 362 |
| RPS19_int_16 | aaaccacctgtaagcaaaat | SEQ ID NO: 363 |
| RPS9_int_1 | gcttactcatggaaactcgg | SEQ ID NO: 364 |
| RPS9_int_2 | tcatagtcagtatctgcccc | SEQ ID NO: 365 |
| RPS9_int_3 | atccgatctcgcgagaataa | SEQ ID NO: 366 |
| RPS9_int_4 | gagagaagtgtgagcgtaag | SEQ ID NO: 367 |
| RPS9_int_5 | atagagtacatgggcacctt | SEQ ID NO: 368 |
| RPS9_int_6 | gtaccaaatttaggggacgg | SEQ ID NO: 369 |
| RPS9_int_7 | tggaatcacaaaaccttcct | SEQ ID NO: 370 |
| RPS9_int_8 | cgtactggcacaacaactag | SEQ ID NO: 371 |
| RPS9_int_9 | gggagaatgaacctcacaag | SEQ ID NO: 372 |
| RPS9_int_10 | gacacaactctcatcactgg | SEQ ID NO: 373 |
| RPS9_int_11 | aaggctggttccatttatcc | SEQ ID NO: 374 |
| RPS9_int_12 | tttcctacttcacaagtgcc | SEQ ID NO: 375 |
| RPS9_int_13 | acctaagaaacagggcaaag | SEQ ID NO: 376 |
| RPS9_int_14 | aggcctatctttagctctgg | SEQ ID NO: 377 |
| RPS9_int_15 | gcccagaaattccacttcat | SEQ ID NO: 378 |
| RPS9_int_16 | aaccctgttatcaccatcac | SEQ ID NO: 379 |
| SLC1A5_int_1 | gaggactcactgagcgaaag | SEQ ID NO: 380 |
| SLC1A5_int_2 | tgcattttccaggaactaa | SEQ ID NO: 381 |
| SLC1A5_int_3 | tgagcccgtattctcattga | SEQ ID NO: 382 |
| SLC1A5_int_4 | aattaaaactcacaggaggc | SEQ ID NO: 383 |
| SLC1A5_int_5 | atgccaagctaacaatgctc | SEQ ID NO: 384 |
| SLC1A5_int_6 | gtgtccatcgttaccagggc | SEQ ID NO: 385 |
| SLC1A5_int_7 | taggcaaagaggtagagccc | SEQ ID NO: 386 |
| SLC1A5_int_8 | aaggactgcagagtgtcaat | SEQ ID NO: 387 |
| SLC1A5_int_9 | acaaagtagagacctatcca | SEQ ID NO: 388 |
| SLC1A5_int_10 | cacctggggtgggaaaagag | SEQ ID NO: 389 |
| SLC1A5_int_11 | gagagggcagcatggaatgg | SEQ ID NO: 390 |
| SLC1A5_int_12 | cagtttgagcaggttgaggg | SEQ ID NO: 391 |
| SLC1A5_int_13 | aaaggacactcagtctacct | SEQ ID NO: 392 |
| SLC1A5_int_14 | ctgtgggcaaggaacagatc | SEQ ID NO: 393 |
| SLC1A5_int_15 | caaacagaatgccccgcacc | SEQ ID NO: 394 |
| SLC1A5_int_16 | gtgaatagagggtgcccat | SEQ ID NO: 395 |
| SUPT5H_int_1 | tctcttgagacaatctggga | SEQ ID NO: 396 |
| SUPT5H_int_2 | cctttgcttgacttcgactt | SEQ ID NO: 397 |
| SUPT5H_int_3 | tgttatctcactggacctga | SEQ ID NO: 398 |
| SUPT5H_int_4 | cttttttaggggtggtgg | SEQ ID NO: 399 |
| SUPT5H_int_5 | ctctgatccaaccaaagtgg | SEQ ID NO: 400 |
| SUPT5H_int_6 | ggaacacagtagtagatgca | SEQ ID NO: 401 |
| SUPT5H_int_7 | accagacacctgagaagtaa | SEQ ID NO: 402 |
| SUPT5H_int_8 | ctggtttgtgattgctacct | SEQ ID NO: 403 |
| SUPT5H_int_9 | gtgcatcaaacaagggatct | SEQ ID NO: 404 |
| SUPT5H_int_10 | ggcaactaacatatcctggg | SEQ ID NO: 405 |
| SUPT5H_int_11 | acacagccacatgaaatctt | SEQ ID NO: 406 |
| SUPT5H_int_12 | gcactctccatctaccaaac | SEQ ID NO: 407 |
| SUPT5H_int_13 | taagtgactgggacaagtca | SEQ ID NO: 408 |
| SUPT5H_int_14 | ggcaatcaaatgtccacaga | SEQ ID NO: 409 |
| SUPT5H_int_15 | cactctccaaaggtcacaat | SEQ ID NO: 410 |
| SUPT5H_int_16 | atccagtgctacagcttaga | SEQ ID NO: 411 |
| TOMM40_int_1 | atcacctcctagtgctgtta | SEQ ID NO: 412 |
| TOMM40_int_2 | ccatcattctaagcccaag | SEQ ID NO: 413 |
| TOMM40_int_3 | ctgctatgacattccatccc | SEQ ID NO: 414 |
| TOMM40_int_4 | gatcacaagagaagtctggc | SEQ ID NO: 415 |

| Probe | Sequence | Identifier |
|---|---|---|
| TOMM40_int_5 | gaacaccagaacagaactcc | SEQ ID NO: 416 |
| TOMM40_int_6 | cacagaattgtcccaaggat | SEQ ID NO: 417 |
| TOMM40_int_7 | aagctgagcaacttaggtc | SEQ ID NO: 418 |
| TOMM40_int_8 | ttgcttgctcaaatctcact | SEQ ID NO: 419 |
| TOMM40_int_9 | tacagcctagttagacaggg | SEQ ID NO: 420 |
| TOMM40_int_10 | gattccacctgtaaagaggc | SEQ ID NO: 421 |
| TOMM40_int_11 | cacagcagaacatctcacaa | SEQ ID NO: 422 |
| TOMM40_int_12 | gagaagagaaacgctgtcac | SEQ ID NO: 423 |
| TOMM40_int_13 | tctggcactatatctccgag | SEQ ID NO: 424 |
| TOMM40_int_14 | taggtccccaaaactgagtag | SEQ ID NO: 425 |
| TOMM40_int_15 | agagactcagagaaaggagg | SEQ ID NO: 426 |
| TOMM40_int_16 | tgtgacgatactggacagat | SEQ ID NO: 427 |
| UBA52_int_1 | ctaaagtcagcacaacccac | SEQ ID NO: 428 |
| UBA52_int_2 | gagaagcaagggcaaaacag | SEQ ID NO: 429 |
| UBA52_int_3 | caaacgttcttcagatcaca | SEQ ID NO: 430 |
| UBA52_int_4 | ggccaactgaggtagaagat | SEQ ID NO: 431 |
| UBA52_int_5 | cactaccccagtttctcaa | SEQ ID NO: 432 |
| UBA52_int_6 | tattactggcagtgtcctct | SEQ ID NO: 433 |
| UBA52_int_7 | gaggctcagttagaggctct | SEQ ID NO: 434 |
| UBA52_int_8 | caatgctcctttcctaggac | SEQ ID NO: 435 |
| UBA52_int_9 | acactgaattcttgtcgctc | SEQ ID NO: 436 |
| UBA52_int_10 | aaggtcagacactgaagtct | SEQ ID NO: 437 |
| UBA52_int_11 | ccgacctctaagtggttcag | SEQ ID NO: 438 |
| UBA52_int_12 | gcatccatctgggtttctaa | SEQ ID NO: 439 |
| UBA52_int_13 | ggagtctgagactgacacat | SEQ ID NO: 440 |
| UBA52_int_14 | cgtgtggaagatacactgtc | SEQ ID NO: 441 |
| UBA52_int_15 | gcctatagtctgctgctttc | SEQ ID NO: 442 |
| UBA52_int_16 | caagcatcggagcacacata | SEQ ID NO: 443 |
| ZNF444_int_1 | gagtcacactggttttcagg | SEQ ID NO: 444 |
| ZNF444_int_2 | cttctctgataagccgtgac | SEQ ID NO: 445 |
| ZNF444_int_3 | gagaggacagctggtaactg | SEQ ID NO: 446 |
| ZNF444_int_4 | ttttgaacacattgggtcc | SEQ ID NO: 447 |
| ZNF444_int_5 | gtgccactactgaaaggat | SEQ ID NO: 448 |
| ZNF444_int_6 | gactgctctgactcttcacc | SEQ ID NO: 449 |
| ZNF444_int_7 | ggtacgcacttatgaggaac | SEQ ID NO: 450 |
| ZNF444_int_8 | tctctgctgctacatctcag | SEQ ID NO: 451 |
| ZNF444_int_9 | catgagaagggagacggatg | SEQ ID NO: 452 |
| ZNF444_int_10 | atcccagacaataagagggg | SEQ ID NO: 453 |
| ZNF444_int_11 | cgaggatagagaagccagag | SEQ ID NO: 454 |
| ZNF444_int_12 | cccactttgggaacaatga | SEQ ID NO: 455 |
| ZNF444_int_13 | gctgcgtttgtgatttgtta | SEQ ID NO: 456 |
| ZNF444_int_14 | ggatgaaagcagaggtcaag | SEQ ID NO: 457 |
| ZNF444_int_15 | ggatgaaagcagaggtcaag | SEQ ID NO: 458 |
| ZNF444_int_16 | taagtgggtcaaggtcagag | SEQ ID NO: 459 |
| ZNF91_int_1 | gattgtggagctgactgaag | SEQ ID NO: 460 |
| ZNF91_int_2 | catcttatcgctgaagggga | SEQ ID NO: 461 |
| ZNF91_int_3 | ctgcacaatctgggagagac | SEQ ID NO: 462 |
| ZNF91_int_4 | gagttaggctggaggaacag | SEQ ID NO: 463 |
| ZNF91_int_5 | tggtaagatagctgcgtcta | SEQ ID NO: 464 |
| ZNF91_int_6 | actgaagacacatcaccta | SEQ ID NO: 465 |
| ZNF91_int_7 | tccaagaaaaaactgaaggg | SEQ ID NO: 466 |
| ZNF91_int_8 | agagaatatgacccagaagc | SEQ ID NO: 467 |
| ZNF91_int_9 | tcaatacctcaggttgtcct | SEQ ID NO: 468 |
| ZNF91_int_10 | gtccacacttgagaagctaa | SEQ ID NO: 469 |
| ZNF91_int_11 | cactattttctgcccccta | SEQ ID NO: 470 |
| ZNF91_int_12 | gcaagttcttacgccatcta | SEQ ID NO: 471 |
| ZNF91_int_13 | gtgcctcaggcacattatac | SEQ ID NO: 472 |
| ZNF91_int_14 | aggagactctgaactatgcc | SEQ ID NO: 473 |
| ZNF91_int_15 | ttaagtgctcaataaccccc | SEQ ID NO: 474 |
| ZNF91_int_16 | tcaagtcaggccattcaatt | SEQ ID NO: 475 |
| AMH_int_1 | cacctgaaggaagacggcgg | SEQ ID NO: 476 |
| AMH_int_2 | ctgatcttccctaggaggac | SEQ ID NO: 477 |
| AMH_int_3 | tcctaggaacaagaccacag | SEQ ID NO: 478 |
| AMH_int_5 | ttcggggacaggacagagtg | SEQ ID NO: 479 |
| AMH_int_6 | aggggcaagtctaagagctg | SEQ ID NO: 480 |
| AMH_int_7 | cagggagtatcttaggccag | SEQ ID NO: 481 |
| AMH_int_9 | ccgggaatctttgggatctg | SEQ ID NO: 482 |
| AMH_int_10 | tgagccattgaaggccacac | SEQ ID NO: 483 |
| AMH_int_12 | gaccctgcaacaaatccatg | SEQ ID NO: 484 |
| AMH_int_13 | ctacgctgttctcagtactg | SEQ ID NO: 485 |
| AMH_int_16 | tggaacccgcaattggagga | SEQ ID NO: 486 |
| AXL_int_1 | ggagatgagacagagaggag | SEQ ID NO: 487 |
| AXL_int_2 | agggagaagccagagaaagg | SEQ ID NO: 488 |
| AXL_int_3 | tctagagacttaacaggtcg | SEQ ID NO: 489 |
| AXL_int_4 | cgacatagttgcagagtgac | SEQ ID NO: 490 |
| AXL_int_5 | ggaagagttagcttaggaac | SEQ ID NO: 491 |
| AXL_int_6 | tgtatgacgctaggttcatc | SEQ ID NO: 492 |
| AXL_int_7 | acccaaaactctgacattct | SEQ ID NO: 493 |

| Probe | Sequence | Identifier |
|---|---|---|
| AXL_int_8 | taacttatatggactcccag | SEQ ID NO: 494 |
| AXL_int_9 | cttttcacccagaacatata | SEQ ID NO: 495 |
| AXL_int_10 | tgatgcctaggacatccaac | SEQ ID NO: 496 |
| AXL_int_11 | tatctgaagaccagaatggc | SEQ ID NO: 497 |
| AXL_int_12 | catctcattctatggatgag | SEQ ID NO: 498 |
| AXL_int_13 | cagaatgtctgacagctcat | SEQ ID NO: 499 |
| AXL_int_14 | atacccaacacacacgtgac | SEQ ID NO: 500 |
| AXL_int_15 | attgacttgccttatctgat | SEQ ID NO: 501 |
| AXL_int_16 | caagatgcctgactcaccac | SEQ ID NO: 502 |
| BCL3_int_1 | atatctatatccttggaacc | SEQ ID NO: 503 |
| BCL3_int_2 | taagagcttgtactttcttg | SEQ ID NO: 504 |
| BCL3_int_3 | tcataacgctacacatctgg | SEQ ID NO: 505 |
| BCL3_int_4 | atatcaggatacagggaacc | SEQ ID NO: 506 |
| BCL3_int_5 | tgagattgtgacatcctgag | SEQ ID NO: 507 |
| BCL3_int_6 | taactgagtacccagaaacc | SEQ ID NO: 508 |
| BCL3_int_7 | cctgatcttgacctcaaata | SEQ ID NO: 509 |
| BCL3_int_8 | agggtgcagaaactacctaa | SEQ ID NO: 510 |
| BCL3_int_9 | tctcactcttggaataggaa | SEQ ID NO: 511 |
| BCL3_int_10 | actgtttaaaaaggggccac | SEQ ID NO: 512 |
| BCL3_int_11 | ttaccagaagcctgttcaaa | SEQ ID NO: 513 |
| BCL3_int_12 | gtgggataaatgtagagtgg | SEQ ID NO: 514 |
| BCL3_int_13 | gattttgtggctgatgaatt | SEQ ID NO: 515 |
| BCL3_int_14 | gacaaagggtcccttaagaa | SEQ ID NO: 516 |
| BCL3_int_15 | acttctaaaactttgctcct | SEQ ID NO: 517 |
| BCL3_int_16 | aatggaggacagagaaggga | SEQ ID NO: 518 |
| ATF5_int_1 | gagaagagactgtgatccga | SEQ ID NO: 519 |
| ATF5_int_2 | gctgacaaacatcgagtcta | SEQ ID NO: 520 |
| ATF5_int_3 | aacaaccaagcacgaagaat | SEQ ID NO: 521 |
| ATF5_int_4 | ggtccaattgcctttacacc | SEQ ID NO: 522 |
| ATF5_int_5 | ctgtcaatctaagccagtcc | SEQ ID NO: 523 |
| ATF5_int_6 | cacttagagggttgcctctg | SEQ ID NO: 524 |
| ATF5_int_7 | gtgacgacagtggttctatc | SEQ ID NO: 525 |
| ATF5_int_8 | tcacaatgtgcttccgaaat | SEQ ID NO: 526 |
| ATF5_int_9 | cctcaactaacggttggttt | SEQ ID NO: 527 |
| ATF5_int_10 | gcctctttgtcacatcgaaa | SEQ ID NO: 528 |
| ATF5_int_11 | agcccttcagcaatgttatc | SEQ ID NO: 529 |
| ATF5_int_12 | cagaatatttcgcctcaagg | SEQ ID NO: 530 |
| ATF5_int_13 | tcccaggggaattaccttag | SEQ ID NO: 531 |
| ATF5_int_14 | gtcctaaagtaggaccgatg | SEQ ID NO: 532 |
| ATF5_int_15 | actcccaagggaatttcttt | SEQ ID NO: 533 |
| ATF5_int_16 | ctacacgcgtgagacaagag | SEQ ID NO: 534 |
| C19orf48_int_1 | acacagccggaaaaagtaat | SEQ ID NO: 535 |
| C19orf48_int_2 | cagctataggagtcgcaaac | SEQ ID NO: 536 |
| C19orf48_int_3 | gaaagaactcaatgtcgcct | SEQ ID NO: 537 |
| C19orf48_int_4 | agcacgaaaatggaaacact | SEQ ID NO: 538 |
| C19orf48_int_5 | ttcctaaggaagcacctgta | SEQ ID NO: 539 |
| C19orf48_int_6 | ctaggttgcacaaaaatgcc | SEQ ID NO: 540 |
| C19orf48_int_7 | actcgatacccccatctgtgc | SEQ ID NO: 541 |
| C19orf48_int_8 | cggcaattcacctagaaact | SEQ ID NO: 542 |
| C19orf48_int_9 | attttctaggtggttgcctg | SEQ ID NO: 543 |
| C19orf48_int_10 | aatattgccaaaggacgacg | SEQ ID NO: 544 |
| C19orf48_int_11 | aggcacaaagcagattgtta | SEQ ID NO: 545 |
| C19orf48_int_12 | ataatgaggagagaccctcg | SEQ ID NO: 546 |
| C19orf48_int_13 | ttgcaggtttctttagcact | SEQ ID NO: 547 |
| C19orf48_int_14 | gcactacatgaagatgtccc | SEQ ID NO: 548 |
| C19orf48_int_15 | actcatccagaaggtaggaa | SEQ ID NO: 549 |
| C19orf48_int_16 | gaggaaacagtctgcaagtc | SEQ ID NO: 550 |
| FTL_int_1 | cgaccgcacaaagaaggctg | SEQ ID NO: 551 |
| FTL_int_2 | atggaggcaacaatggttag | SEQ ID NO: 552 |
| FTL_int_3 | tgggagatgtagtccattac | SEQ ID NO: 553 |
| FTL_int_4 | tcaaatcaaggctcctcgcg | SEQ ID NO: 554 |
| FTL_int_5 | caagaccgaactcaatctcc | SEQ ID NO: 555 |
| FTL_int_6 | ctatttccagcggttaagag | SEQ ID NO: 556 |
| FTL_int_7 | taagaccacgcagcggtgtg | SEQ ID NO: 557 |
| FTL_int_8 | ctagctcttacagctatacg | SEQ ID NO: 558 |
| FTL_int_9 | tgacagcttgtatttatcac | SEQ ID NO: 559 |
| FTL_int_10 | aaacctacatttcccaagag | SEQ ID NO: 560 |
| FTL_int_11 | cacacactcggcacatagaa | SEQ ID NO: 561 |
| FTL_int_12 | gaagggagaaatggctcaga | SEQ ID NO: 562 |
| FTL_int_13 | atggatgcagcgggtacgta | SEQ ID NO: 563 |
| FTL_int_14 | aaatttgcccaaagggagca | SEQ ID NO: 564 |
| FTL_int_15 | gtgtgaaatgaggctctgaa | SEQ ID NO: 565 |
| FTL_int_16 | cagccagttgcagattaaaa | SEQ ID NO: 566 |
| HNRNPL_int_1 | aacttgtgatggtttcaagg | SEQ ID NO: 567 |
| HNRNPL_int_2 | ttggtttatcaaatcctcgg | SEQ ID NO: 568 |
| HNRNPL_int_3 | cgaaatgcttccaacatggc | SEQ ID NO: 569 |
| HNRNPL_int_4 | ctccaaaagcaacgactggt | SEQ ID NO: 570 |
| HNRNPL_int_5 | caactcgtaaccccctaaacc | SEQ ID NO: 571 |

-continued

| Probe | Sequence | Identifier |
|---|---|---|
| HNRNPL_int_6 | gggtagaattggattctatt | SEQ ID NO: 572 |
| HNRNPL_int_7 | tgagaatcactgggcagaag | SEQ ID NO: 573 |
| HNRNPL_int_8 | cttcctaagagaagtatctt | SEQ ID NO: 574 |
| HNRNPL_int_9 | cccataccattaagaaccga | SEQ ID NO: 575 |
| HNRNPL_int_10 | ttagaaagaccagagactcc | SEQ ID NO: 576 |
| HNRNPL_int_11 | caaattccttgccctttaac | SEQ ID NO: 577 |
| HNRNPL_int_12 | tccactcgaccaaggaaaca | SEQ ID NO: 578 |
| HNRNPL_int_13 | caagtcccaaatcttacgtt | SEQ ID NO: 579 |
| HNRNPL_int_14 | atgcacaggaaagactaggg | SEQ ID NO: 580 |
| HNRNPL_int_15 | acccagtcagataaaacagt | SEQ ID NO: 581 |
| HNRNPL_int_16 | ccagaaatcgtggacacaca | SEQ ID NO: 582 |
| MRPL34_int_1 | ccaaaccacaactcgttagt | SEQ ID NO: 583 |
| MRPL34_int_2 | agactaaggacacgtacagg | SEQ ID NO: 584 |
| MRPL34_int_3 | gtttgcatctccaaaagcaa | SEQ ID NO: 585 |
| MRPL34_int_4 | gcaacttcgttaagggaact | SEQ ID NO: 586 |
| MRPL34_int_5 | tactcagagtctaattttgt | SEQ ID NO: 587 |
| MRPL34_int_6 | cttaacgttctgatgaccag | SEQ ID NO: 588 |
| MRPL34_int_7 | caagaatgttagcttttcctg | SEQ ID NO: 589 |
| MRPL34_int_8 | tcacatacatatccttgtat | SEQ ID NO: 590 |
| MRPL34_int_9 | aagtgaaacagtcagtaggt | SEQ ID NO: 591 |
| MRPL34_int_10 | aatggtgtactcatttatct | SEQ ID NO: 592 |
| MRPL34_int_11 | ctgatcagcagacagtataa | SEQ ID NO: 593 |
| MRPL34_int_12 | aaatgagttgcttcaccatt | SEQ ID NO: 594 |
| MRPL34_int_13 | cttttaatctccacatctag | SEQ ID NO: 595 |
| MRPL34_int_14 | tgttcctacacttttaacac | SEQ ID NO: 596 |
| MRPL34_int_15 | tacacttttaacaccttccg | SEQ ID NO: 597 |
| MRPL34_int_16 | cctatgctcatgagaataca | SEQ ID NO: 598 |
| MYADM_int_1 | ctagccacaggaaagtaact | SEQ ID NO: 599 |
| MYADM_int_2 | aacgcagccacaggactaaa | SEQ ID NO: 600 |
| MYADM_int_3 | ttgcaaaacctacagcttcc | SEQ ID NO: 601 |
| MYADM_int_4 | aaccaatttgcttctttagt | SEQ ID NO: 602 |
| MYADM_int_5 | ttccaactgtccagtaggaa | SEQ ID NO: 603 |
| MYADM_int_6 | ccagcttctgggaaactcag | SEQ ID NO: 604 |
| MYADM_int_7 | aaaaagctagtttgagcctc | SEQ ID NO: 605 |
| MYADM_int_8 | tgagatttaggactggagta | SEQ ID NO: 606 |
| MYADM_int_9 | ttggagattagcaaccttca | SEQ ID NO: 607 |
| MYADM_int_10 | cttctgacaaggagcctaaa | SEQ ID NO: 608 |
| MYADM_int_11 | ggaaaaccaagagatctccc | SEQ ID NO: 609 |
| MYADM_int_12 | gatatcttctcatagagatc | SEQ ID NO: 610 |
| MYADM_int_13 | agggacccacatctaataag | SEQ ID NO: 611 |
| MYADM_int_14 | gaacagtgacctagacattt | SEQ ID NO: 612 |
| MYADM_int_15 | tgtgagcaaacttccttctt | SEQ ID NO: 613 |
| MYADM_int_16 | aaaacgcttgtcttccacag | SEQ ID NO: 614 |
| RPL13A_int_1 | tcattatggatgttaagctc | SEQ ID NO: 615 |
| RPL13A_int_2 | cttatcccaaaagacttcca | SEQ ID NO: 616 |
| RPL13A_int_3 | aaatgccacattgtagccaa | SEQ ID NO: 617 |
| RPL13A_int_4 | gtgaaatcaaagtagcccgc | SEQ ID NO: 618 |
| RPL13A_int_5 | cgccaatccccaaaacgacg | SEQ ID NO: 619 |
| RPL13A_int_6 | atacttaagtagctacacca | SEQ ID NO: 620 |
| RPL13A_int_7 | caaagaaacctttccagggc | SEQ ID NO: 621 |
| RPL13A_int_8 | gaacacaacttgcctagatc | SEQ ID NO: 622 |
| RPL13A_int_9 | aaaatccagacagacttcct | SEQ ID NO: 623 |
| RPL13A_int_10 | ttacacatgctttgtaagcg | SEQ ID NO: 624 |
| RPL13A_int_11 | gattaggcagagtagtcaaa | SEQ ID NO: 625 |
| RPL13A_int_12 | ttctcttctaatgtatagga | SEQ ID NO: 626 |
| RPL13A_int_13 | ccagttacaagaccttgtaa | SEQ ID NO: 627 |
| RPL13A_int_14 | tgaacgaagaccagcaaggc | SEQ ID NO: 628 |
| RPL13A_int_15 | ctatgagtattttatgctca | SEQ ID NO: 629 |
| RPL13A_int_16 | gggagacaagggcaaaagga | SEQ ID NO: 630 |
| RPL18_int_1 | agtgacaggtccagataaag | SEQ ID NO: 631 |
| RPL18_int_2 | atcgaacccgacttttcata | SEQ ID NO: 632 |
| RPL18_int_3 | tactgtgtacccaacgaaca | SEQ ID NO: 633 |
| RPL18_int_4 | tcagactgtgttgacaatta | SEQ ID NO: 634 |
| RPL18_int_5 | ctttctgagcaacttaagtt | SEQ ID NO: 635 |
| RPL18_int_6 | catcagtcaatccaacaacc | SEQ ID NO: 636 |
| RPL18_int_7 | cgaatccttattcagaacct | SEQ ID NO: 637 |
| RPL18_int_8 | atcaaaactggttcccatac | SEQ ID NO: 638 |
| RPL18_int_9 | gcacacagaaccctgaaaca | SEQ ID NO: 639 |
| RPL18_int_10 | tgatccctctgtaaaaaggg | SEQ ID NO: 640 |
| RPL18_int_11 | ctagaatggaggatctgcaa | SEQ ID NO: 641 |
| RPL18_int_12 | aacagaaccagagacccgag | SEQ ID NO: 642 |
| RPL18_int_13 | acacatgatgatctggacta | SEQ ID NO: 643 |
| RPL18_int_14 | acgggaagacagtgagaagc | SEQ ID NO: 644 |
| RPL18_int_15 | cgcgactggctgagacaaac | SEQ ID NO: 645 |
| RPL18_int_16 | agcagagcctttgacataaa | SEQ ID NO: 646 |
| RPL28_int_1 | catcgtgaataagggacccg | SEQ ID NO: 647 |
| RPL28_int_2 | ggcccaaaccagacaaaact | SEQ ID NO: 648 |
| RPL28_int_3 | ttcctgcctgacagtaaaaa | SEQ ID NO: 649 |

| Probe | Sequence | Identifier |
|---|---|---|
| RPL28_int_4 | aacaaccaccgaggaagttc | SEQ ID NO: 650 |
| RPL28_int_5 | gacttgctttgagaatttca | SEQ ID NO: 651 |
| RPL28_int_6 | tgacagcacaatgtatggag | SEQ ID NO: 652 |
| RPL28_int_7 | aatccccaaaaaggcctgca | SEQ ID NO: 653 |
| RPL28_int_8 | ccgactcacacgaacattca | SEQ ID NO: 654 |
| RPL28_int_9 | gaacacatgtgaagctggac | SEQ ID NO: 655 |
| RPL28_int_10 | ttgctgccactgagtaaaag | SEQ ID NO: 656 |
| RPL28_int_11 | catgtattcggcaatccaag | SEQ ID NO: 657 |
| RPL28_int_12 | caatgggtatgaacagcttc | SEQ ID NO: 658 |
| RPL28_int_13 | ctgtccaccatgaaaacact | SEQ ID NO: 659 |
| RPL28_int_14 | gacagtctcacattgagaag | SEQ ID NO: 660 |
| RPL28_int_15 | catattgcaaccagtagtgg | SEQ ID NO: 661 |
| RPL28_int_16 | aggctgaaagcaagaatcca | SEQ ID NO: 662 |
| RPS28_int_2 | aggaaagaagctgggttcag | SEQ ID NO: 663 |
| RPS28_int_4 | agaggtcacatcagggttta | SEQ ID NO: 664 |
| RPS28_int_5 | gaaatgagaatcggctcccg | SEQ ID NO: 665 |
| RPS28_int_6 | aaagggaaccatcagaaccc | SEQ ID NO: 666 |
| RPS28_int_7 | cggggccagaatacagatcg | SEQ ID NO: 667 |
| RPS28_int_8 | agcagatatgaattcagaga | SEQ ID NO: 668 |
| RPS28_int_10 | tggaggaagaagtaagggcg | SEQ ID NO: 669 |
| RPS28_int_12 | caccaaccaaaggtctatca | SEQ ID NO: 670 |
| RPS28_int_13 | tcaccctgggcttaacgaag | SEQ ID NO: 671 |
| RPS28_int_14 | cagcaattggcaaactcccg | SEQ ID NO: 672 |
| RPS28_int_15 | aacatgagatgttgacaggc | SEQ ID NO: 673 |
| TPM4-tv2_int_1 | gaagccgggaagaaaggagg | SEQ ID NO: 674 |
| TPM4-tv2_int_2 | gtcaaaccctagacaatgga | SEQ ID NO: 675 |
| TPM4-tv2_int_3 | gccgcgaaagaggcgagaaa | SEQ ID NO: 676 |
| TPM4-tv2_int_4 | aggaatcagctggagaaagg | SEQ ID NO: 677 |
| TPM4-tv2_int_5 | ctcccataactgcacagaaa | SEQ ID NO: 678 |
| TPM4-tv2_int_6 | tttattctataagacccagc | SEQ ID NO: 679 |
| TPM4-tv2_int_7 | tcatcatacaactttcttgc | SEQ ID NO: 680 |
| TPM4-tv2_int_8 | taagtgtgagaaagaggcca | SEQ ID NO: 681 |
| TPM4-tv2_int_9 | ccattttgaagccgagttaa | SEQ ID NO: 682 |
| TPM4-tv2_int_10 | tccaaaaacatcttctctcc | SEQ ID NO: 683 |
| TPM4-tv2_int_11 | atcctttgcttttcaagaa | SEQ ID NO: 684 |
| TPM4-tv2_int_12 | gaaaccagctgtcgggaaac | SEQ ID NO: 685 |
| TPM4-tv2_int_13 | agatgtcagttaatcacaca | SEQ ID NO: 686 |
| TPM4-tv2_int_14 | gctagatacatgtggcaaag | SEQ ID NO: 687 |
| TPM4-tv2_int_15 | ggatttcccttataagtaa | SEQ ID NO: 688 |
| TPM4-tv2_int_16 | caatcaaagccttccacacg | SEQ ID NO: 689 |

Example 3

SNV-Detection Probes and Masks

SNP FISH Oligonucleotide Sequences

| Probe | Sequence | Identifier |
|---|---|---|
| BRAF-T1799A-WT | tttcactgtagctagaccaaaatcacct | SEQ ID NO: 690 |
| BRAF-T1799A-MUT | tttctctgtagctagaccaaaatcacct | SEQ ID NO: 691 |
| BRAF-1799-Mask | aggtgattttggtctag | SEQ ID NO: 692 |
| BRAF-Common-Match | ggcgtgtaagtaatccatgccctgtg | SEQ ID NO: 693 |
| BRAF-Common-Mismatch | ggcgagtaagtaatccatgccctgtg | SEQ ID NO: 694 |
| BRAF-Common-Mask | cacagggcatggattac | SEQ ID NO: 695 |
| DNMT1-Common-Match | cttggttcccgttttctagacgtc | SEQ ID NO: 696 |
| DNMT1-Common-MisMatch | cttcgttcccgttttctagacgtc | SEQ ID NO: 697 |
| DNMT1-Common-Mask | gacgtctagaaaacg | SEQ ID NO: 698 |
| SKA3-GM-SNP-Mat | cattttgttcagtttctgtgttgga | SEQ ID NO: 699 |
| SKA3-GM-SNP-PAT | cattctgttcagtttctgtgttgga | SEQ ID NO: 700 |
| SKA3-GM-SNP-Mask | tccaacacagaaactgaac | SEQ ID NO: 701 |
| DNMT1-GM-SNP-Mat | gagacgggtcatcatcatagattgg | SEQ ID NO: 702 |
| DNMT1-GM-SNP-Pat | gagatgggtcatcatcatagattgg | SEQ ID NO: 703 |
| DNMT1-GM-SNP-Mask | ccaatctatgatgatgacc | SEQ ID NO: 704 |

-continued

| Probe | Sequence | Identifier |
|---|---|---|
| SUZ12-GM-SNP-Mat | atctctattggatattctattcatgaaacac | SEQ ID NO: 705 |
| SUZ12-GM-SNP-Pat | atctgtattggatattctattcatgaaacac | SEQ ID NO: 706 |
| SUZ12-GM-SNP-Mask | gtgtttcatgaatagaatatccaat | SEQ ID NO: 707 |
| EBF1-GM-SNP-Mat | ctgtataaatgaatctgcctggtgt | SEQ ID NO: 708 |
| EBF1-GM-SNP-Pat | ctgtgtaaatgaatctgcctggtgt | SEQ ID NO: 709 |
| EBF1-GM-SNP-Mask | acaccaggcagattcattt | SEQ ID NO: 710 |

SNP Chr19 GM Paint Probes

| Probe | Sequence | Identifier |
|---|---|---|
| PTBP1-1-m | ggagggcaggaggcggccg | SEQ ID NO: 711 |
| PTBP1-2-m | tccccggggccaggagagc | SEQ ID NO: 712 |
| PTBP1-3-m | aggaaacaacgttagcctggtggc | SEQ ID NO: 713 |
| PTBP1-4-m | ccaccgaacggcacgattccagc | SEQ ID NO: 714 |
| EEF2-5-m | cacccaccccaggaaataacggg | SEQ ID NO: 715 |
| P2RY11-6-m | cccatgttggccaagaggtct | SEQ ID NO: 716 |
| IER2-7-m | gacactcccgtgaacacgtgg | SEQ ID NO: 717 |
| TOMM40-14-m | acctcgctgacaccttgctgaca | SEQ ID NO: 718 |
| TOMM40-15-m | ccactactactactctaattgctc | SEQ ID NO: 719 |
| SLC1A5-16-m | cagccgaccgaccctccaacc | SEQ ID NO: 720 |
| RPL18-17-m | aaaagaatctttatccctttccccc | SEQ ID NO: 721 |
| PPP1R15A-18-m | ctcctaaggctgcttctgaatca | SEQ ID NO: 722 |
| LINC00085-19-m | tgaccccacccagaacttcatagcca | SEQ ID NO: 723 |
| RPS9-20-m | gaaggcgaaccacttcccggaag | SEQ ID NO: 724 |
| ICAM1-21-m | tgggacctcagcatacccaatag | SEQ ID NO: 725 |
| SUPT5H-22-m | ccccctcaatggcctgcttc | SEQ ID NO: 726 |
| PVR-23-m | accagcctgggcagcatagcgaaa | SEQ ID NO: 727 |
| PPP1R15A-24-m | tcctctctaagactcaagaatctgg | SEQ ID NO: 728 |
| EGLN2-25-m | tcgatccgagcccgacggg | SEQ ID NO: 729 |
| PTBP1-1-p | ggagagcaggaggcggccg | SEQ ID NO: 730 |
| PTBP1-2-p | tccccggggccaggagagc | SEQ ID NO: 731 |
| PTBP1-3-p | aggagacaacgttagcctggtggc | SEQ ID NO: 732 |
| PTBP1-4-p | ccactgaacggcacgattccagc | SEQ ID NO: 733 |
| EEF2-5-p | caccgaccccaggaaataacggg | SEQ ID NO: 734 |
| P2RY11-6-p | cccacgttggccaagaggtct | SEQ ID NO: 735 |
| IER2-7-p | gacagtcccgtgaacacgtgg | SEQ ID NO: 736 |
| TOMM40-14-p | acctcgctgacaccttgctgaca | SEQ ID NO: 737 |
| TOMM40-15-p | ccaccactactactctaattgctc | SEQ ID NO: 738 |
| SLC1A5-16-p | cagcagaccgaccctccaacc | SEQ ID NO: 739 |
| RPL18-17-p | aaaataatctttatccctttccccc | SEQ ID NO: 740 |
| PPP1R15A-18-p | ctcccaaggctgcttctgaatca | SEQ ID NO: 741 |
| LINC00085-19-p | tgacacacccagaacttcatagcca | SEQ ID NO: 742 |
| RPS9-20-p | gaagccgaaccacttcccggaag | SEQ ID NO: 743 |
| ICAM1-21-p | tggggcctcagcatacccaatag | SEQ ID NO: 744 |
| SUPT5H-22-p | ccccttcaatggcctgcttc | SEQ ID NO: 745 |
| PVR-23-p | accaacctgggcagcatagcgaaa | SEQ ID NO: 746 |
| PPP1R15A-24-p | ttctttctaagactcaagaatctgg | SEQ ID NO: 747 |
| EGLN2-25-p | tcgaccccgagcccgacggg | SEQ ID NO: 748 |
| PTBP1-1-t6 | cggccgcctcctg | SEQ ID NO: 749 |
| PTBP1-2-t6 | gctctcctggcc | SEQ ID NO: 750 |
| PTBP1-3-t6 | gccaccaggctaacgttg | SEQ ID NO: 751 |
| PTBP1-4-t6 | gctggaatcgtgccgtt | SEQ ID NO: 752 |
| EEF2-5-t6 | cccgttatttcctgggg | SEQ ID NO: 753 |
| P2RY11-6-t6 | agacctcttggccaa | SEQ ID NO: 754 |
| IER2-7-t6 | ccacgtgttcacgggg | SEQ ID NO: 755 |
| TOMM40-14-t6 | tgtcagcaaggtgtcag | SEQ ID NO: 756 |
| TOMM40-15-t6 | gagcaattagagtagtag | SEQ ID NO: 757 |
| SLC1A5-16-t6 | ggttggagggtcggt | SEQ ID NO: 758 |
| RPL18-17-t6 | gggggaaagggataaagat | SEQ ID NO: 759 |
| PPP1R15A-18-t6 | tgattcagaagcagcct | SEQ ID NO: 760 |
| LINC00085-19-t6 | tggctatgaagttctgggt | SEQ ID NO: 761 |
| RPS9-20-t6 | cttccgggaagtggttc | SEQ ID NO: 762 |
| ICAM1-21-t6 | ctattgggtatgctgag | SEQ ID NO: 763 |

-continued

| Probe | Sequence | Identifier |
|---|---|---|
| SUPT5H-22-t6 | gaagcaggccattg | SEQ ID NO: 764 |
| PVR-23-t6 | tttcgctatgctgcccag | SEQ ID NO: 765 |
| PPP1R15A-24-t6 | ccagattcttgagtcttag | SEQ ID NO: 766 |
| EGLN2-25-t6 | cccgtcgggctcg | SEQ ID NO: 767 |

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for detecting a mutation in a target nucleic acid, comprising:
   (a) hybridizing at least one labeled detection probe to a first region of the target nucleic acid having at least one mutation; wherein the detection probe comprises (i) an oligonucleotide mask, (ii) a hybridization region with an unmasked nucleotide sequence and (ii) a masked region with a nucleotide sequence complementary to the target nucleic acid hybridized to the oligonucleotide mask;
   wherein the hybridization region of the detection probe and target nucleic acid includes the mutation, which is positioned within one third of the length of the detection probe from the 5' end of the detection probe; wherein the detection probe is labeled with a first fluorophore;
   (b) hybridizing at least one labeled guide probe to a second region of the target nucleic acid having at least one mutation; wherein the hybridization region of the at least one guide probe and target nucleic acid does not include the mutation; wherein the guide probe is labeled with a second fluorophore; and wherein the first and second fluorophores are distinct and are distinguishable from one another when visualized;
   (c) detecting the at least one guide probe fluorophore in a first image; and
   (d) detecting the detection probe fluorophore in a second image;
   wherein, if colocation of the at least one guide probe fluorophore and the detection probe fluorophore is detected, the mutation in the nucleotide sequence of the target nucleic acid is detected.

2. The method of claim 1, wherein the mutation is a small-scale mutation selected from the group consisting of a single nucleotide variant (SNV), insertion, and deletion.

3. The method of claim 1, wherein the detection probe hybridizes to the target nucleic acid on the unmasked region of the detection probe.

4. The method of claim 3, wherein the oligonucleotide masking a portion of the nucleotide sequence of the detection probe denatures from the detection probe when the detection probe hybridizes to the target nucleic acid.

5. The method of claim 4, wherein the previously masked portion of the detection probe hybridizes to the target nucleic acid subsequent to the oligonucleotide denaturing from the detection probe.

6. The method of claim 1, wherein the target nucleic acid is a ribonucleic acid (RNA).

7. The method of claim 6, wherein the RNA is selected from the group consisting of messenger RNA, intronic RNA, exonic DNA, and non-coding RNA.

8. The method of claim 1, wherein the detection probe comprises a nucleotide sequence of at least 10 bases.

9. The method of claim 1, wherein the at least one guide probe comprises a nucleotide sequence of at least 10 bases.

10. The method of claim 1, wherein the oligonucleotide masking the detection probe has a nucleotide sequence of at least 5 bases.

11. The method of claim 1, wherein the unmasked nucleotide sequence comprises at least 2 bases.

12. The method of claim 1, wherein the mutation is positioned at the fifth base from the 5' end of the detection probe and wherein the detection probe is about 25-bases long.

13. The method of claim 1, wherein the target nucleic acid is from a single molecule in a single cell.

\* \* \* \* \*